(12) United States Patent
Johnson

(10) Patent No.: US 10,167,266 B2
(45) Date of Patent: Jan. 1, 2019

(54) SODIUM CHANNEL BLOCKERS

(71) Applicant: Parion Sciences, Inc., Durham, NC (US)

(72) Inventor: Michael R. Johnson, Chapel Hill, NC (US)

(73) Assignee: Parion Sciences, Inc., Durham, NC (US)

( * ) Notice: Subject to any disclaimer, the term of this patent is extended or adjusted under 35 U.S.C. 154(b) by 0 days.

(21) Appl. No.: 15/336,574

(22) Filed: Oct. 27, 2016

(65) Prior Publication Data
US 2017/0267650 A1 Sep. 21, 2017

Related U.S. Application Data

(63) Continuation of application No. 14/727,189, filed on Jun. 1, 2015, now abandoned, which is a continuation of application No. 14/158,441, filed on Jan. 17, 2014, now abandoned, which is a continuation of application No. 13/492,711, filed on Jun. 8, 2012, now Pat. No. 8,846,688, which is a continuation of application No. 12/179,353, filed on Jul. 24, 2008, now Pat. No. 8,198,286, which is a continuation of application No. 10/532,110, filed as application No. PCT/US03/04817 on Feb. 19, 2003, now abandoned, which is a continuation-in-part of application No. 10/076,571, filed on Feb. 19, 2002, now Pat. No. 6,858,615.

(51) Int. Cl.
| | |
|---|---|
| A61K 31/496 | (2006.01) |
| C07D 241/28 | (2006.01) |
| C07D 241/26 | (2006.01) |
| A61K 31/4965 | (2006.01) |
| A61K 31/497 | (2006.01) |
| A61K 31/706 | (2006.01) |
| A61K 45/06 | (2006.01) |
| C07D 241/32 | (2006.01) |
| C07D 405/12 | (2006.01) |
| C07H 15/26 | (2006.01) |

(52) U.S. Cl.
CPC .......... *C07D 241/28* (2013.01); *A61K 31/497* (2013.01); *A61K 31/4965* (2013.01); *A61K 31/706* (2013.01); *A61K 45/06* (2013.01); *C07D 241/26* (2013.01); *C07D 241/32* (2013.01); *C07D 405/12* (2013.01); *C07H 15/26* (2013.01)

(58) Field of Classification Search
CPC .................................................. A61K 31/496
USPC .................................................. 514/255.05
See application file for complete search history.

(56) References Cited

U.S. PATENT DOCUMENTS

| | | |
|---|---|---|
| 3,240,780 A | 3/1966 | Cragoe, Jr. et al. |
| 3,249,610 A | 5/1966 | Cragoe, Jr. et al. |
| 3,268,406 A | 8/1966 | Cragoe, Jr. et al. |
| 3,274,191 A | 9/1966 | Cragoe, Jr. et al. |
| 3,274,192 A | 9/1966 | Cragoe, Jr. et al. |
| 3,290,311 A | 12/1966 | Cragoe, Jr. et al. |
| 3,299,063 A | 1/1967 | Cragoe, Jr. et al. |
| 3,300,494 A | 1/1967 | Cragoe, Jr. et al. |
| 3,305,552 A | 2/1967 | Cragoe, Jr. et al. |
| 3,313,813 A | 4/1967 | Cragoe |
| 3,316,266 A | 4/1967 | Tull et al. |
| 3,325,494 A | 6/1967 | Weinstock et al. |
| 3,341,540 A | 9/1967 | Cragoe, Jr. et al. |
| 3,359,269 A | 12/1967 | Cragoe, Jr. et al. |
| 3,360,517 A | 12/1967 | Cragoe, Jr. et al. |
| 3,361,748 A | 1/1968 | Cragoe, Jr. et al. |
| 3,461,123 A | 8/1969 | Jones et al. |
| 3,472,848 A | 10/1969 | Cragoe, Jr. et al. |
| 3,487,082 A | 12/1969 | Cragoe, Jr. et al. |
| 3,491,094 A | 1/1970 | Cragoe, Jr. et al. |
| 3,503,973 A | 3/1970 | Cragoe, Jr. et al. |
| 3,506,662 A | 4/1970 | Cragoe, Jr. et al. |
| 3,507,865 A | 4/1970 | Jones et al. |
| 3,507,866 A | 4/1970 | Jones et al. |
| 3,515,723 A | 6/1970 | Cragoe, Jr. et al. |
| 3,527,758 A | 9/1970 | Cragoe, Jr. et al. |
| 3,531,484 A | 9/1970 | Flicking et al. |
| 3,539,569 A | 11/1970 | Tull et al. |
| 3,544,568 A | 12/1970 | Cragoe, Jr. et al. |
| 3,544,571 A | 12/1970 | Cragoe, Jr. et al. |

(Continued)

FOREIGN PATENT DOCUMENTS

| | | |
|---|---|---|
| CN | 101534813 A | 9/2009 |
| EA | 005975 B1 | 8/2005 |

(Continued)

OTHER PUBLICATIONS

U.S. Appl. No. 10/920,418, filed Aug. 18, 2004, Johnson.

(Continued)

*Primary Examiner* — Jeffrey H Murray
(74) *Attorney, Agent, or Firm* — Wolf, Greenfield & Sacks, P.C.

(57) ABSTRACT

The present invention relates to compounds of Formula (I) and pharmaceutical compositions thereof. Compounds of Formula (I) are epithelial sodium channel (ENaC) blockers useful in the hydration of mucosal surfaces, enhancement of mucociliary clearance, or restoration of mucosal defense in a subject. The compounds and compositions can therefore be used to treat diseases which rely on the hydration of mucosal surfaces.

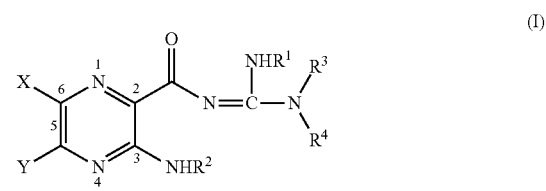

17 Claims, 8 Drawing Sheets

(56) References Cited

U.S. PATENT DOCUMENTS

| | | |
|---|---|---|
| 3,555,023 A | 1/1971 | Cragoe, Jr. et al. |
| 3,555,024 A | 1/1971 | Cragoe, Jr. et al. |
| 3,573,305 A | 3/1971 | Cragoe, Jr. et al. |
| 3,573,306 A | 3/1971 | Shepard et al. |
| 3,575,975 A | 4/1971 | Cragoe, Jr. et al. |
| 3,577,418 A | 5/1971 | Cragoe, Jr. et al. |
| 3,586,688 A | 6/1971 | Cragoe, Jr. et al. |
| 3,625,950 A | 12/1971 | Cragoe, Jr. et al. |
| 3,660,397 A | 5/1972 | Jones et al. |
| 3,660,400 A | 5/1972 | Cragoe, Jr. et al. |
| 3,668,241 A | 6/1972 | Cragoe, Jr. et al. |
| 3,794,734 A | 2/1974 | Cragoe, Jr. et al. |
| 3,864,401 A | 2/1975 | Schultz et al. |
| 3,894,065 A | 7/1975 | Cragoe, Jr. et al. |
| 3,894,085 A | 7/1975 | Eschenmoser |
| 3,914,253 A | 10/1975 | Cragoe, Jr. et al. |
| 3,928,624 A | 12/1975 | Cragoe, Jr. et al. |
| 3,929,872 A | 12/1975 | Cragoe, Jr. et al. |
| 3,931,239 A | 1/1976 | Cragoe, Jr. et al. |
| 3,935,313 A | 1/1976 | Aron-Samuel et al. |
| 3,948,895 A | 4/1976 | Donald |
| 3,953,476 A | 4/1976 | Cragoe, Jr. et al. |
| 3,956,374 A | 5/1976 | Shepard et al. |
| 3,958,004 A | 5/1976 | Cragoe, Jr. et al. |
| 3,966,966 A | 6/1976 | Cragoe, Jr. et al. |
| 3,974,212 A | 8/1976 | Cragoe, Jr. et al. |
| 3,976,681 A | 8/1976 | Cragoe, Jr. et al. |
| 3,976,686 A | 8/1976 | Cragoe, Jr. et al. |
| 3,979,361 A | 9/1976 | Schultz et al. |
| 3,984,465 A | 10/1976 | Cragoe, Jr. et al. |
| 3,984,552 A | 10/1976 | Cragoe, Jr. et al. |
| 3,987,091 A | 10/1976 | Cragoe, Jr. et al. |
| 3,989,749 A | 11/1976 | Cragoe, Jr. et al. |
| 3,991,087 A | 11/1976 | Cragoe, Jr. et al. |
| 3,991,106 A | 11/1976 | Cragoe, Jr. et al. |
| 4,003,927 A | 1/1977 | Woltersdorf, Jr. et al. |
| 4,006,180 A | 2/1977 | Cragoe, Jr. et al. |
| 4,012,524 A | 3/1977 | Cragoe, Jr. et al. |
| 4,018,802 A | 4/1977 | Cragoe, Jr. et al. |
| 4,020,177 A | 4/1977 | Cragoe, Jr. et al. |
| 4,022,794 A | 5/1977 | Smith et al. |
| 4,025,625 A | 5/1977 | Rooney et al. |
| 4,029,803 A | 6/1977 | Hunter et al. |
| 4,029,816 A | 6/1977 | Cragoe, Jr. et al. |
| 4,033,996 A | 7/1977 | Cragoe, Jr. et al. |
| 4,044,153 A | 8/1977 | Schultz et al. |
| 4,054,652 A | 10/1977 | Rooney et al. |
| 4,055,596 A | 10/1977 | Cragoe, Jr. et al. |
| 4,055,597 A | 10/1977 | Cragoe, Jr. et al. |
| 4,059,087 A | 11/1977 | Tanigami et al. |
| 4,059,601 A | 11/1977 | Cragoe, Jr. et al. |
| 4,059,602 A | 11/1977 | Cragoe, Jr. et al. |
| 4,061,643 A | 12/1977 | Cragoe, Jr. et al. |
| 4,066,675 A | 1/1978 | Cragoe, Jr. et al. |
| 4,066,692 A | 1/1978 | Cragoe, Jr. et al. |
| 4,067,980 A | 1/1978 | Cragoe, Jr. et al. |
| 4,070,464 A | 1/1978 | Cragoe, Jr. et al. |
| 4,070,539 A | 1/1978 | Cragoe, Jr. et al. |
| 4,081,554 A | 3/1978 | Cragoe, Jr. et al. |
| 4,085,117 A | 4/1978 | Cragoe, Jr. et al. |
| 4,085,125 A | 4/1978 | Cragoe, Jr. et al. |
| 4,085,211 A | 4/1978 | Cragoe, Jr. et al. |
| 4,085,219 A | 4/1978 | Cragoe, Jr. et al. |
| 4,087,435 A | 5/1978 | Cragoe, Jr. et al. |
| 4,087,526 A | 5/1978 | Cragoe, Jr. et al. |
| 4,087,542 A | 5/1978 | Cragoe, Jr. et al. |
| 4,091,015 A | 5/1978 | Strike |
| 4,091,105 A | 5/1978 | Rokach et al. |
| 4,091,107 A | 5/1978 | Cragoe, Jr. et al. |
| 4,092,356 A | 5/1978 | Cragoe, Jr. et al. |
| 4,092,414 A | 5/1978 | Cragoe, Jr. et al. |
| 4,096,267 A | 6/1978 | Cragoe, Jr. et al. |
| 4,097,504 A | 6/1978 | Cragoe, Jr. et al. |
| 4,100,294 A | 7/1978 | Cragoe, Jr. et al. |
| 4,102,888 A | 7/1978 | Smith et al. |
| 4,105,769 A | 8/1978 | Rooney et al. |
| 4,108,859 A | 8/1978 | Tong |
| 4,111,877 A | 9/1978 | Dixon et al. |
| 4,112,236 A | 9/1978 | Bicking et al. |
| 4,115,402 A | 9/1978 | Cragoe, Jr. et al. |
| 4,115,573 A | 9/1978 | Cragoe, Jr. et al. |
| 4,126,629 A | 11/1978 | Cragoe, Jr. et al. |
| 4,127,584 A | 11/1978 | Rokach et al. |
| 4,127,587 A | 11/1978 | Wade et al. |
| 4,128,564 A | 12/1978 | Cragoe, Jr. et al. |
| 4,133,885 A | 1/1979 | Bolhofer et al. |
| 4,140,776 A | 2/1979 | Cragoe, Jr. et al. |
| 4,140,861 A | 2/1979 | Cragoe, Jr. et al. |
| 4,145,551 A | 3/1979 | Cragoe, Jr. et al. |
| 4,150,235 A | 4/1979 | Cragoe, Jr. et al. |
| 4,154,742 A | 5/1979 | Cragoe, Jr. et al. |
| 4,155,908 A | 5/1979 | Cragoe, Jr. et al. |
| 4,156,005 A | 5/1979 | Stokker et al. |
| 4,159,279 A | 6/1979 | Smith et al. |
| 4,163,781 A | 8/1979 | Cragoe, Jr. et al. |
| 4,163,794 A | 8/1979 | Cragoe, Jr. et al. |
| 4,166,177 A | 8/1979 | Cragoe, Jr. et al. |
| 4,175,203 A | 11/1979 | Cragoe, Jr. et al. |
| 4,177,285 A | 12/1979 | Cragoe, Jr. et al. |
| 4,178,386 A | 12/1979 | Williams et al. |
| 4,181,661 A | 1/1980 | Rooney et al. |
| 4,181,727 A | 1/1980 | Cragoe, Jr. et al. |
| 4,182,764 A | 1/1980 | Cragoe, Jr. et al. |
| 4,187,315 A | 2/1980 | Cragoe, Jr. et al. |
| 4,189,496 A | 2/1980 | Cragoe, Jr. et al. |
| 4,190,655 A | 2/1980 | DeMarco et al. |
| 4,196,292 A | 4/1980 | Woltersdorf, Jr. et al. |
| 4,203,988 A | 5/1980 | Bolhofer et al. |
| 4,207,329 A | 6/1980 | Williams et al. |
| 4,208,413 A | 6/1980 | Cragoe, Jr. et al. |
| 4,220,654 A | 9/1980 | Bolhofer et al. |
| 4,221,790 A | 9/1980 | Cragoe, Jr. et al. |
| 4,224,447 A | 9/1980 | Woltersdorf, Jr. et al. |
| 4,225,609 A | 9/1980 | Cragoe, Jr. et al. |
| 4,226,867 A | 10/1980 | Cragoe, Jr. et al. |
| 4,229,456 A | 10/1980 | Bolhofer et al. |
| 4,233,452 A | 11/1980 | Williams et al. |
| 4,237,130 A | 12/1980 | Cragoe, Jr. et al. |
| 4,237,144 A | 12/1980 | Cragoe, Jr. et al. |
| 4,246,406 A | 1/1981 | Cragoe, Jr. et al. |
| 4,249,021 A | 2/1981 | Cragoe, Jr. et al. |
| 4,256,758 A | 3/1981 | Cragoe, Jr. et al. |
| 4,260,771 A | 4/1981 | Cragoe, Jr. et al. |
| 4,263,207 A | 4/1981 | Rokach et al. |
| 4,267,341 A | 5/1981 | Rokach et al. |
| 4,272,537 A | 6/1981 | Woltersdorf, Jr. et al. |
| 4,277,602 A | 7/1981 | Woltersdorf et al. |
| 4,282,365 A | 8/1981 | Rokach et al. |
| 4,291,050 A | 9/1981 | Woltersdorf, Jr. et al. |
| 4,292,430 A | 9/1981 | Rokach et al. |
| 4,294,829 A | 10/1981 | Suzuki et al. |
| 4,296,122 A | 10/1981 | Cragoe, Jr. et al. |
| 4,296,237 A | 10/1981 | Cragoe, Jr. et al. |
| 4,298,743 A | 11/1981 | Cragoe, Jr. et al. |
| 4,309,540 A | 1/1982 | Bock et al. |
| 4,316,043 A | 2/1982 | Cragoe, Jr. et al. |
| 4,317,822 A | 3/1982 | Woltersdorf, Jr. et al. |
| 4,317,922 A | 3/1982 | Cragoe, Jr. et al. |
| 4,336,397 A | 6/1982 | Cragoe, Jr. et al. |
| 4,337,258 A | 6/1982 | Rooney et al. |
| 4,337,354 A | 6/1982 | Cragoe, Jr. et al. |
| 4,342,776 A | 8/1982 | Cragoe, Jr. et al |
| 4,342,782 A | 8/1982 | Cragoe, Jr. |
| 4,349,561 A | 9/1982 | Cragoe, Jr. et al. |
| 4,356,313 A | 10/1982 | Cragoe, Jr. et al. |
| 4,356,314 A | 10/1982 | Cragoe, Jr. et al. |
| 4,362,724 A | 12/1982 | Bock et al. |
| 4,375,475 A | 3/1983 | Willard et al. |
| 4,377,588 A | 3/1983 | Cragoe, Jr. et al. |
| 4,379,791 A | 4/1983 | Cragoe, Jr. et al. |
| 4,389,393 A | 6/1983 | Schor et al. |
| 4,389,417 A | 6/1983 | Bourke et al. |
| 4,390,537 A | 6/1983 | Cragoe, Jr. |
| 4,394,385 A | 7/1983 | Cragoe, Jr. |

(56) References Cited

U.S. PATENT DOCUMENTS

| | | |
|---|---|---|
| 4,394,515 A | 7/1983 | Rokach et al. |
| 4,401,669 A | 8/1983 | Cragoe, Jr. et al. |
| 4,420,615 A | 12/1983 | Bolhofer et al. |
| 4,425,337 A | 1/1984 | Alexander et al. |
| 4,428,956 A | 1/1984 | Cragoe, Jr. et al. |
| 4,428,959 A | 1/1984 | Cragoe, Jr. et al. |
| 4,431,652 A | 2/1984 | Cragoe, Jr. et al. |
| 4,431,660 A | 2/1984 | Cragoe, Jr. et al. |
| 4,432,992 A | 2/1984 | Cragoe, Jr. et al. |
| 4,440,740 A | 4/1984 | Fix et al. |
| 4,448,786 A | 5/1984 | Cragoe, Jr. et al. |
| 4,454,132 A | 6/1984 | Bock et al. |
| 4,459,422 A | 7/1984 | Willard et al. |
| 4,463,208 A | 7/1984 | Cragoe, Jr. et al. |
| 4,464,363 A | 8/1984 | Higuchi et al. |
| 4,465,850 A | 8/1984 | Cragoe, Jr. et al. |
| 4,501,729 A | 2/1985 | Boucher et al. |
| 4,510,322 A | 4/1985 | Blaine et al. |
| 4,536,507 A | 8/1985 | Rokach et al. |
| 4,537,902 A | 8/1985 | Cragoe, Jr. et al. |
| 4,567,289 A | 1/1986 | Willard et al. |
| 4,579,869 A | 4/1986 | Cragoe, Jr. et al. |
| 4,582,842 A | 4/1986 | Cragoe, Jr. et al. |
| 4,594,349 A | 6/1986 | Beyer, Jr. |
| 4,596,821 A | 6/1986 | Cragoe, Jr. et al. |
| 4,604,394 A | 8/1986 | Kaczorowski et al. |
| 4,604,396 A | 8/1986 | Cragoe, Jr. et al. |
| 4,604,403 A | 8/1986 | Cragoe, Jr. et al. |
| 4,605,663 A | 8/1986 | Cragoe, Jr. et al. |
| 4,605,664 A | 8/1986 | Cragoe, Jr. et al. |
| 4,625,047 A | 11/1986 | Cragoe, Jr. et al. |
| 4,634,717 A | 1/1987 | Cragoe, Jr. et al. |
| 4,654,365 A | 3/1987 | Cragoe, Jr. et al. |
| 4,663,322 A | 5/1987 | Beyer, Jr. |
| 4,675,341 A | 6/1987 | Cragoe, Jr. |
| 4,680,414 A | 7/1987 | Cragoe, Jr. et al. |
| 4,699,917 A | 10/1987 | Cragoe, Jr. et al. |
| 4,699,926 A | 10/1987 | Abraham et al. |
| 4,710,513 A | 12/1987 | Willard et al. |
| 4,719,310 A | 1/1988 | Pietruszkiewicz et al. |
| 4,731,381 A | 3/1988 | Abraham et al. |
| 4,731,470 A | 3/1988 | Pietruszkiewicz et al. |
| 4,731,471 A | 3/1988 | Cragoe, Jr. et al. |
| 4,731,472 A | 3/1988 | Pietruszkiewicz et al. |
| 4,731,473 A | 3/1988 | Abraham et al. |
| 4,751,244 A | 6/1988 | Abraham et al. |
| 4,754,061 A | 6/1988 | Cragoe, Jr. et al. |
| 4,769,370 A | 9/1988 | Woltersdorf, Jr. et al. |
| 4,771,076 A | 9/1988 | Cragoe, Jr. et al. |
| 4,775,695 A | 10/1988 | Cragoe, Jr. et al. |
| 4,777,281 A | 10/1988 | Woltersdorf, Jr. et al. |
| 4,778,897 A | 10/1988 | Cragoe, Jr. et al. |
| 4,782,073 A | 11/1988 | Cragoe, Jr. |
| 4,797,391 A | 1/1989 | Woltersdorf, Jr. et al. |
| 4,835,142 A | 5/1989 | Suzuki et al. |
| 4,835,313 A | 5/1989 | Pietruszkiewicz et al. |
| 4,894,376 A | 1/1990 | Morad et al. |
| 4,923,874 A | 5/1990 | McMahon et al. |
| 4,937,232 A | 6/1990 | Bell et al. |
| 4,952,582 A | 8/1990 | Beyer, Jr. |
| 5,132,296 A | 7/1992 | Cherksey |
| 5,182,299 A | 1/1993 | Gullans et al. |
| 5,215,991 A | 6/1993 | Burke |
| 5,242,947 A | 9/1993 | Cherksey et al. |
| 5,292,498 A | 3/1994 | Boucher, Jr. |
| 5,312,820 A | 5/1994 | Ashton et al. |
| 5,384,128 A | 1/1995 | Meezan et al. |
| 5,420,116 A | 5/1995 | Puchelle et al. |
| 5,449,682 A | 9/1995 | Greenlee et al. |
| 5,512,269 A | 4/1996 | Molina y Vedia et al. |
| 5,538,991 A | 7/1996 | Ashton et al. |
| 5,618,557 A | 4/1997 | Wille et al. |
| 5,628,984 A | 5/1997 | Boucher, Jr. |
| 5,635,160 A | 6/1997 | Stutts, III et al. |
| 5,651,957 A | 7/1997 | Molina y Vedia et al. |
| 5,656,256 A | 8/1997 | Boucher et al. |
| 5,683,675 A | 11/1997 | Molina y Vedia et al. |
| 5,707,644 A | 1/1998 | Illum |
| 5,716,931 A | 2/1998 | Molina y Vedia et al. |
| 5,725,842 A | 3/1998 | Boucher, Jr. et al. |
| 5,750,697 A | 5/1998 | Cherksey |
| 5,817,028 A | 10/1998 | Anderson |
| 5,849,706 A | 12/1998 | Molina y Vedia et al. |
| 5,866,610 A | 2/1999 | Lang et al. |
| 5,876,700 A | 3/1999 | Boucher, Jr. et al. |
| 5,902,567 A | 5/1999 | Boucher, Jr. |
| 5,908,611 A | 6/1999 | Gottlieb et al. |
| 5,935,555 A | 8/1999 | Stutts, III et al. |
| 5,955,100 A | 9/1999 | Bosslet et al. |
| 5,962,477 A | 10/1999 | Mak |
| 5,994,336 A | 11/1999 | Zasloff et al. |
| 6,015,828 A | 1/2000 | Cuppoletti |
| 6,022,527 A | 2/2000 | Boucher, Jr. et al. |
| 6,033,688 A | 3/2000 | Mrsny et al. |
| 6,051,576 A | 4/2000 | Ashton et al. |
| 6,071,910 A | 6/2000 | Gleich et al. |
| 6,133,247 A | 10/2000 | Boucher, Jr. |
| 6,136,294 A | 10/2000 | Adjei et al. |
| 6,143,279 A | 11/2000 | Boucher, Jr. et al. |
| 6,153,187 A | 11/2000 | Yacoby-Zeevi |
| 6,159,968 A | 12/2000 | Cuppoletti |
| 6,190,691 B1 | 2/2001 | Mak |
| 6,204,270 B1 | 3/2001 | Ron et al. |
| 6,214,536 B1 | 4/2001 | Boucher, Jr. |
| 6,235,266 B1 | 5/2001 | Stutts, III et al. |
| 6,264,975 B1 | 7/2001 | Boucher, Jr. |
| 6,294,188 B1 | 9/2001 | Ragavan et al. |
| 6,297,226 B1 | 10/2001 | Glasky |
| 6,300,350 B1 | 10/2001 | Belloni et al. |
| 6,323,187 B1 | 11/2001 | Yerxa et al. |
| 6,331,529 B1 | 12/2001 | Yerxa et al. |
| 6,344,475 B1 | 2/2002 | Caplan et al. |
| 6,399,585 B1 | 6/2002 | Larson et al. |
| 6,403,633 B2 | 6/2002 | Illig et al. |
| 6,451,288 B1 | 9/2002 | Boucher, Jr. et al. |
| 6,458,338 B1 | 10/2002 | Adjei et al. |
| 6,475,467 B1 | 11/2002 | Keller et al. |
| 6,475,509 B1 | 11/2002 | Boucher, Jr. |
| 6,476,048 B1 | 11/2002 | Szabo et al. |
| 6,607,741 B2 | 8/2003 | Boucher, Jr. |
| 6,613,345 B2 | 9/2003 | Boucher, Jr. |
| 6,739,172 B2 | 5/2004 | Wagner |
| 6,753,164 B2 | 6/2004 | Ni et al. |
| 6,858,614 B2 * | 2/2005 | Johnson ............... C07D 401/12 514/255.06 |
| 6,858,615 B2 * | 2/2005 | Johnson ............... C07D 241/26 514/255.06 |
| 6,903,105 B2 * | 6/2005 | Johnson ............. A61K 31/4965 514/255.06 |
| 6,926,911 B1 | 8/2005 | Boucher, Jr. |
| 6,995,160 B2 * | 2/2006 | Johnson ............. A61K 31/4965 514/255.05 |
| 7,026,325 B2 * | 4/2006 | Johnson ............. A61K 31/4965 514/255.05 |
| 7,030,117 B2 * | 4/2006 | Johnson ............. A61K 31/4965 514/241 |
| 7,056,524 B2 | 6/2006 | Boucher, Jr. |
| 7,064,129 B2 * | 6/2006 | Johnson ............... C07D 241/26 514/245 |
| 7,186,833 B2 * | 3/2007 | Johnson ............... C07D 241/26 544/405 |
| 7,189,719 B2 * | 3/2007 | Johnson ............... C07D 241/26 514/241 |
| 7,192,958 B2 * | 3/2007 | Johnson ............... C07D 241/26 514/241 |
| 7,192,959 B2 * | 3/2007 | Johnson ............... C07D 241/26 514/241 |
| 7,192,960 B2 * | 3/2007 | Johnson ............... C07D 241/26 514/252.02 |
| 7,241,766 B2 | 7/2007 | Johnson |
| 7,247,636 B2 * | 7/2007 | Johnson ............... C07D 241/26 514/255.06 |

(56) References Cited

U.S. PATENT DOCUMENTS

| | | | |
|---|---|---|---|
| 7,247,637 B2 * | 7/2007 | Johnson | C07D 241/26 514/255.06 |
| 7,317,013 B2 * | 1/2008 | Johnson | C04B 35/632 514/252.11 |
| 7,332,496 B2 | 2/2008 | Johnson | |
| 7,345,044 B2 * | 3/2008 | Johnson | A61K 31/4965 514/255.06 |
| 7,368,447 B2 * | 5/2008 | Johnson | C07D 241/26 514/252.01 |
| 7,368,450 B2 * | 5/2008 | Johnson | C07D 241/26 514/255.05 |
| 7,368,451 B2 * | 5/2008 | Johnson | C07D 241/26 514/255.05 |
| 7,375,102 B2 | 5/2008 | Fu et al. | |
| 7,375,107 B2 * | 5/2008 | Johnson | C07D 241/34 514/255.06 |
| 7,388,013 B2 * | 6/2008 | Johnson | C07D 241/26 514/255.06 |
| 7,399,766 B2 | 7/2008 | Johnson | |
| 7,410,968 B2 * | 8/2008 | Johnson | C07D 241/26 514/241 |
| 7,553,855 B2 | 6/2009 | Young et al. | |
| 7,745,442 B2 | 6/2010 | Johnson et al. | |
| 7,807,834 B2 | 10/2010 | Johnson et al. | |
| 7,820,678 B2 * | 10/2010 | Johnson | A61K 31/4965 514/255.05 |
| 7,842,697 B2 | 11/2010 | Johnson | |
| 7,868,010 B2 | 1/2011 | Johnson et al. | |
| 7,875,619 B2 | 1/2011 | Johnson | |
| 7,956,059 B2 | 6/2011 | Johnson | |
| 7,981,898 B2 | 7/2011 | Johnson et al. | |
| 8,008,494 B2 | 8/2011 | Johnson | |
| 8,022,210 B2 | 9/2011 | Johnson | |
| 8,058,278 B2 | 11/2011 | Johnson et al. | |
| 8,124,607 B2 * | 2/2012 | Johnson | C07D 241/26 514/255.06 |
| 8,143,256 B2 | 3/2012 | Johnson | |
| 8,163,758 B2 * | 4/2012 | Johnson | A61K 31/4965 514/255.06 |
| 8,198,286 B2 * | 6/2012 | Johnson | C07D 241/26 514/255.06 |
| 8,211,895 B2 | 7/2012 | Johnson et al. | |
| 8,227,474 B2 | 7/2012 | Johnson | |
| 8,261,047 B2 | 9/2012 | Moyer | |
| 8,288,391 B2 | 10/2012 | Johnson et al. | |
| 8,314,105 B2 | 11/2012 | Johnson | |
| 8,324,218 B2 | 12/2012 | Johnson | |
| 8,431,579 B2 | 4/2013 | Johnson et al. | |
| 8,507,497 B2 | 8/2013 | Johnson et al. | |
| 8,551,534 B2 | 10/2013 | Boucher et al. | |
| 8,575,176 B2 | 11/2013 | Johnson | |
| 8,669,262 B2 | 3/2014 | Johnson | |
| 8,846,688 B2 | 9/2014 | Johnson | |
| 8,980,898 B2 | 3/2015 | Johnson et al. | |
| 9,029,382 B2 | 5/2015 | Johnson | |
| 9,072,738 B2 | 7/2015 | Johnson | |
| 9,102,633 B2 | 8/2015 | Johnson | |
| 9,260,398 B2 | 2/2016 | Johnson et al. | |
| 9,586,910 B2 | 3/2017 | Johnson | |
| 9,586,911 B2 | 3/2017 | Johnson | |
| 9,593,084 B2 | 3/2017 | Johnson | |
| 9,695,134 B2 | 7/2017 | Johnson | |
| 2003/0135716 A1 | 7/2003 | Vinitzky | |
| 2003/0195160 A1 | 10/2003 | Johnson | |
| 2003/0199456 A1 | 10/2003 | Johnson | |
| 2004/0116415 A1 | 6/2004 | Sun et al. | |
| 2004/0162296 A1 | 8/2004 | Johnson | |
| 2004/0195160 A1 | 10/2004 | Max et al. | |
| 2004/0198744 A1 | 10/2004 | Johnson | |
| 2004/0198745 A1 | 10/2004 | Johnson | |
| 2004/0198746 A1 | 10/2004 | Johnson | |
| 2004/0198747 A1 | 10/2004 | Johnson | |
| 2004/0198748 A1 | 10/2004 | Johnson | |
| 2004/0198749 A1 | 10/2004 | Johnson | |
| 2004/0199456 A1 | 10/2004 | Flint et al. | |
| 2004/0204424 A1 | 10/2004 | Johnson | |
| 2004/0204425 A1 | 10/2004 | Johnson | |
| 2004/0229884 A1 | 11/2004 | Johnson | |
| 2005/0059676 A1 | 3/2005 | Johnson | |
| 2005/0080091 A1 | 4/2005 | Johnson et al. | |
| 2005/0080092 A1 | 4/2005 | Johnson | |
| 2005/0080093 A1 | 4/2005 | Johnson et al. | |
| 2005/0090505 A1 | 4/2005 | Johnson et al. | |
| 2005/0113388 A1 | 5/2005 | Johnson | |
| 2005/0113389 A1 | 5/2005 | Johnson | |
| 2005/0113390 A1 | 5/2005 | Johnson | |
| 2005/0228182 A1 | 10/2005 | Johnson et al. | |
| 2005/0234072 A1 | 10/2005 | Johnson et al. | |
| 2006/0040954 A1 | 2/2006 | Johnson | |
| 2006/0052394 A1 | 3/2006 | Johnson et al. | |
| 2006/0052395 A1 | 3/2006 | Johnson et al. | |
| 2006/0063780 A1 | 3/2006 | Johnson | |
| 2006/0142306 A1 | 6/2006 | Johnson | |
| 2006/0142581 A1 | 6/2006 | Johnson | |
| 2006/0205738 A1 | 9/2006 | Johnson et al. | |
| 2007/0018640 A1 | 1/2007 | Guzik et al. | |
| 2007/0021439 A1 | 1/2007 | Johnson | |
| 2007/0032509 A1 | 2/2007 | Johnson et al. | |
| 2007/0265280 A1 | 11/2007 | Johnson | |
| 2008/0076782 A1 | 3/2008 | Johnson | |
| 2008/0090841 A1 | 4/2008 | Johnson et al. | |
| 2008/0096896 A1 | 4/2008 | Johnson | |
| 2008/0103148 A1 | 5/2008 | Johnson | |
| 2008/0167466 A1 | 7/2008 | Johnson et al. | |
| 2008/0171879 A1 | 7/2008 | Johnson | |
| 2008/0171880 A1 | 7/2008 | Johnson et al. | |
| 2008/0176863 A1 | 7/2008 | Johnson et al. | |
| 2008/0177072 A1 | 7/2008 | Johnson | |
| 2008/0200476 A1 | 8/2008 | Johnson | |
| 2008/0249109 A1 | 10/2008 | Johnson et al. | |
| 2008/0293740 A1 | 11/2008 | Johnson et al. | |
| 2009/0018144 A1 | 1/2009 | Johnson et al. | |
| 2009/0062308 A1 | 3/2009 | Johnson | |
| 2009/0076273 A1 | 3/2009 | Johnson | |
| 2009/0082287 A1 | 3/2009 | Johnson et al. | |
| 2009/0104272 A1 | 4/2009 | Boucher et al. | |
| 2009/0214444 A1 | 8/2009 | Johnson | |
| 2009/0227530 A1 | 9/2009 | Johnson | |
| 2009/0227594 A1 | 9/2009 | Johnson | |
| 2009/0253714 A1 | 10/2009 | Johnson et al. | |
| 2009/0324724 A1 | 12/2009 | Johnson | |
| 2010/0074881 A1 | 3/2010 | Boucher et al. | |
| 2010/0130547 A1 | 5/2010 | Zhang et al. | |
| 2010/0144661 A1 | 6/2010 | Johnson | |
| 2010/0267746 A1 | 10/2010 | Johnson | |
| 2011/0003832 A1 | 1/2011 | Johnson et al. | |
| 2011/0008268 A1 | 1/2011 | Johnson et al. | |
| 2011/0046158 A1 | 2/2011 | Johnson et al. | |
| 2011/0144338 A1 | 2/2011 | Johnson et al. | |
| 2011/0195973 A1 | 8/2011 | Johnson | |
| 2011/0230483 A1 | 9/2011 | Baettig et al. | |
| 2012/0044272 A1 | 2/2012 | Han et al. | |
| 2012/0116083 A1 | 5/2012 | Johnson | |
| 2012/0220606 A1 | 8/2012 | Johnson et al. | |
| 2013/0012692 A1 | 1/2013 | Johnson | |
| 2013/0060034 A1 | 3/2013 | Johnson | |
| 2013/0178482 A1 | 7/2013 | Johnson | |
| 2013/0324559 A1 | 12/2013 | Johnson et al. | |
| 2014/0031371 A1 | 1/2014 | Johnson | |
| 2014/0096765 A1 | 4/2014 | Boucher et al. | |
| 2014/0107133 A1 | 4/2014 | Johnson | |
| 2014/0142118 A1 | 5/2014 | Johnson | |
| 2014/0170244 A1 | 6/2014 | Johnson | |
| 2014/0171447 A1 | 6/2014 | Johnson | |
| 2014/0179625 A1 | 6/2014 | Johnson | |
| 2015/0056305 A1 | 2/2015 | Johnson et al. | |
| 2015/0166487 A1 | 6/2015 | Johnson | |
| 2015/0166488 A1 | 6/2015 | Johnson | |
| 2015/0290189 A1 | 10/2015 | Johnson | |
| 2015/0299142 A1 | 10/2015 | Johnson | |
| 2015/0307530 A1 | 10/2015 | Johnson et al. | |
| 2015/0376145 A1 | 12/2015 | Johnson et al. | |
| 2015/0376146 A1 | 12/2015 | Johnson et al. | |

(56) References Cited

U.S. PATENT DOCUMENTS

| | | |
|---|---|---|
| 2017/0305868 A1 | 10/2017 | Johnson |
| 2017/0327472 A1 | 11/2017 | Johnson |
| 2017/0334864 A1 | 11/2017 | Johnson |
| 2017/0362187 A1 | 12/2017 | Johnson |

FOREIGN PATENT DOCUMENTS

| | | |
|---|---|---|
| FR | 1 525 670 A | 5/1968 |
| FR | 1 525 671 A | 5/1968 |
| GB | 1145934 A1 | 6/1967 |
| GB | 1158399 A1 | 6/1967 |
| JP | 2005-530692 A | 10/2005 |
| JP | 2006-518389 A | 8/2006 |
| JP | 2007-517764 A | 7/2007 |
| JP | 2010-502738 A | 1/2010 |
| JP | 4557550 B2 | 6/2010 |
| WO | WO 00/23023 A1 | 4/2000 |
| WO | WO 01/05773 A1 | 1/2001 |
| WO | WO 01/28584 A1 | 4/2001 |
| WO | WO 02/40457 A1 | 5/2002 |
| WO | WO 03/070182 A2 | 8/2003 |
| WO | WO 03/070184 A2 | 8/2003 |
| WO | WO 2004/073629 A2 | 9/2004 |
| WO | WO 2005/016879 A2 | 2/2005 |
| WO | WO 2005/018560 A2 | 3/2005 |
| WO | WO 2005/018644 A1 | 3/2005 |
| WO | WO 2005/025496 A2 | 3/2005 |
| WO | WO 2005/034847 A2 | 4/2005 |
| WO | WO 2005/044180 A2 | 5/2005 |
| WO | WO 2006/022935 A1 | 3/2006 |
| WO | WO 2006/023573 A2 | 3/2006 |
| WO | WO 2006/023617 A2 | 3/2006 |
| WO | WO 2007/018640 A1 | 2/2007 |
| WO | WO 2007/071396 A2 | 6/2007 |
| WO | WO 2007/071400 A1 | 6/2007 |
| WO | WO 2007/146867 A2 | 12/2007 |
| WO | WO 2007/146869 A1 | 12/2007 |
| WO | WO 2007/146870 A1 | 12/2007 |
| WO | WO 2008/030217 A2 | 3/2008 |
| WO | WO 2008/031028 A2 | 3/2008 |
| WO | WO 2008/031048 A2 | 3/2008 |
| WO | WO 2008/124491 A1 | 10/2008 |
| WO | WO 2008/124496 A1 | 10/2008 |
| WO | WO 2008/135557 A1 | 11/2008 |
| WO | WO 2009/049159 A1 | 4/2009 |
| WO | WO 2009/074575 A2 | 6/2009 |
| WO | WO 2009/138378 A1 | 11/2009 |
| WO | WO 2009/139948 A1 | 11/2009 |
| WO | WO 2009/150137 A2 | 12/2009 |
| WO | WO 2011/156355 A1 | 12/2011 |
| WO | WO 2013/003386 A1 | 1/2013 |
| WO | WO 2013/003444 A1 | 1/2013 |
| WO | WO 2014/076091 A1 | 5/2014 |

OTHER PUBLICATIONS

U.S. Appl. No. 12/098,581, filed Apr. 7, 2008, Johnson.
U.S. Appl. No. 10/920,391, filed Aug. 18, 2004, Johnson.
U.S. Appl. No. 11/573,421, filed Jun. 10, 2009, Johnson.
U.S. Appl. No. 12/049,993, filed Mar. 17, 2008, Johnson.
U.S. Appl. No. 12/050,010, filed Mar. 17, 2008, Johnson.
U.S. Appl. No. 12/050,019, filed Mar. 17, 2008, Johnson.
U.S. Appl. No. 11/852,003, filed Sep. 7, 2007, Johnson et al.
U.S. Appl. No. 11/851,803, filed Sep. 7, 2007, Johnson et al.
U.S. Appl. No. 12/304,040, filed Jun. 23, 2010, Johnson.
U.S. Appl. No. 13/669,822, filed Nov. 6, 2012, Johnson.
U.S. Appl. No. 12/304,006, filed Dec. 9, 2008, Johnson et al.
U.S. Appl. No. 14/106,156, filed Dec. 13, 2013, Johnson.
U.S. Appl. No. 14/577,098, filed Dec. 19, 2014, Johnson.
U.S. Appl. No. 15/446,852, filed Mar. 1, 2017, Johnson.
U.S. Appl. No. 14/106,098, filed Dec. 13, 2013, Johnson.
U.S. Appl. No. 14/592,480, filed Jan. 8, 2015, Johnson.
U.S. Appl. No. 10/076,551, filed Feb. 19, 2002, Johnson.
U.S. Appl. No. 10/828,235, filed Apr. 21, 2004, Johnson.
U.S. Appl. No. 10/828,278, filed Apr. 21, 2004, Johnson.
U.S. Appl. No. 10/828,329, filed Apr. 21, 2004, Johnson.
U.S. Appl. No. 10/828,353, filed Apr. 21, 2004, Johnson.
U.S. Appl. No. 10/828,354, filed Apr. 21, 2004, Johnson.
U.S. Appl. No. 11/696,003, filed Apr. 3, 2007, Johnson.
U.S. Appl. No. 10/367,947, filed Feb. 19, 2003, Johnson.
U.S. Appl. No. 10/545,083, filed Aug. 9, 2005, Johnson.
U.S. Appl. No. 10/973,474, filed Oct. 27, 2004, Johnson.
U.S. Appl. No. 11/261,734, filed Oct. 31, 2005, Johnson.
U.S. Appl. No. 11/950,674, filed Dec. 5, 2007, Johnson.
U.S. Appl. No. 10/973,447, filed Oct. 27, 2004, Johnson.
U.S. Appl. No. 10/973,473, filed Oct. 27, 2004, Johnson.
U.S. Appl. No. 10/920,353, filed Aug. 18, 2004, Johnson.
U.S. Appl. No. 11/960,989, filed Dec. 20, 2007, Johnson.
U.S. Appl. No. 12/393,252, filed Feb. 26, 2009, Johnson.
U.S. Appl. No. 13/353,018, filed Jan. 18, 2012, Johnson.
U.S. Appl. No. 14/043,223, filed Oct. 1, 2013, Johnson.
U.S. Appl. No. 10/920,410, filed Aug. 18, 2004, Johnson et al.
U.S. Appl. No. 11/131,262, filed May 18, 2005, Johnson et al.
U.S. Appl. No. 11/138,280, filed May 27, 2005, Johnson et al.
U.S. Appl. No. 11/211,422, filed Aug. 26, 2005, Johnson et al.
U.S. Appl. No. 11/211,660, filed Aug. 26, 2005, Johnson et al.
U.S. Appl. No. 11/211,707, filed Aug. 26, 2005, Johnson et al.
U.S. Appl. No. 12/049,894, filed Mar. 17, 2008, Johnson et al.
U.S. Appl. No. 12/049,946, filed Mar. 17, 2008, Johnson et al.
U.S. Appl. No. 12/049,968, filed Mar. 17, 2008, Johnson et al.
U.S. Appl. No. 12/171,814, filed Jul. 11, 2008, Johnson et al.
U.S. Appl. No. 12/171,867, filed Jul. 11, 2008, Johnson et al.
U.S. Appl. No. 12/171,897, filed Jul. 11, 2008, Johnson et al.
U.S. Appl. No. 12/939,579, filed Nov. 4, 2010, Johnson et al.
U.S. Appl. No. 11/195,758, filed Aug. 3, 2005, Johnson et al.
U.S. Appl. No. 12/876,615, filed Sep. 7, 2010, Johnson et al.
U.S. Appl. No. 13/467,618, filed May 9, 2012, Johnson et al.
U.S. Appl. No. 11/573,693, filed Feb. 14, 2007, Johnson.
U.S. Appl. No. 14/106,125, filed Dec. 13, 2013, Johnson.
U.S. Appl. No. 15/452,387, filed Mar. 7, 2017, Johnson.
U.S. Appl. No. 13/533,911, filed Jun. 26, 2012, Johnson.
U.S. Appl. No. 14/132,194, filed Dec. 18, 2013, Johnson.
U.S. Appl. No. 15/446,877, filed Mar. 1, 2017, Johnson.
U.S. Appl. No. 10/076,571, filed Feb. 19, 2002, Johnson.
U.S. Appl. No. 10/532,110, filed Apr. 21, 2005, Johnson.
U.S. Appl. No. 12/179,353, filed Jul. 24, 2008, Johnson.
U.S. Appl. No. 13/492,711, filed Jun. 8, 2012, Johnson.
U.S. Appl. No. 14/158,441, filed Jan. 17, 2014, Johnson.
U.S. Appl. No. 14/727,189, filed Jun. 1, 2015, Johnson.
U.S. Appl. No. 10/828,171, filed Apr. 21, 2004, Johnson.
U.S. Appl. No. 10/828,352, filed Apr. 21, 2004, Johnson.
U.S. Appl. No. 10/828,466, filed Apr. 21, 2004, Johnson.
U.S. Appl. No. 10/828,479, filed Apr. 21, 2004, Johnson.
U.S. Appl. No. 11/695,936, filed Apr. 3, 2007, Johnson.
U.S. Appl. No. 12/190,022, filed Aug. 12, 2008, Johnson.
U.S. Appl. No. 12/703,441, filed Feb. 10, 2010, Johnson.
PCT/US2004/026808, Apr. 15, 2005, International Search Report and Written Opinion.
PCT/US2005/017740, Aug. 31, 2005, International Search Report and Written Opinion.
PCT/US2007/077907, Mar. 27, 2008, International Search Report and Written Opinion.
PCT/US2007/077880, Sep. 15, 2008, International Search Report and Written Opinion.
PCT/US2007/070857, Dec. 6, 2007, International Search Report and Written Opinion.
PCT/US/2007/070861, Nov. 21, 2007, International Search Report and Written Opinion.
PCT/US2013/075244, Feb. 17, 2014, International Search Report and Written Opinion.
PCT/US2013/075093, Mar. 3, 2014, International Search Report and Written Opinion.
PCT/US2003/004823, May 10, 2004, International Search Report.
PCT/US2004/004451, Aug. 27, 2004, International Search Report and Written Opinion.

(56) References Cited

OTHER PUBLICATIONS

PCT/US2004/026880, Apr. 15, 2005, International Search Report and Written Opinion.
PCT/US2009/035286, Oct. 21, 2009, International Search Report and Written Opinion.
PCT/US2004/026885, Jan. 31, 2005, International Search Report and Written Opinion.
PCT/US2006/015957, Oct. 5, 2006, International Search Report and Written Opinion.
PCT/US2005/029345, Mar. 21, 2006, International Search Report and Written Opinion.
PCT/US2013/075108, Feb. 6, 2014, International Search Report and Written Opinion.
PCT/US2012/044272, Sep. 20, 2012, International Search Report and Written Opinion.
PCT/US2003/004817, Aug. 21, 2003, International Search Report.
International Search Report and Written Opinion, dated Apr. 15, 2005, in connection with Application No. PCT/US2004/026808.
International Search Report and Written Opinion, dated Aug. 31, 2005, in connection with Application No. PCT/US2005/017740.
International Search Report and Written Opinion, dated Mar. 27, 2008, in connection with Application No. PCT/US2007/077907.
International Search Report and Written Opinion, dated Sep. 15, 2008, in connection with Application No. PCT/US2007/077880.
International Search Report and Written Opinion, dated Dec. 6, 2007, in connection with Application No. PCT/US2007/070857.
International Search Report and Written Opinion, dated Nov. 21, 2007, in connection with Application No. PCT/US/2007/070861.
International Search Report and Written Opinion, dated Feb. 17, 2014, in connection with Application No. PCT/US2013/075244.
International Search Report and Written Opinion, dated Mar. 3, 2014, in connection with Application No. PCT/US2013/075093.
International Search Report, dated May 10, 2004, in connection with Application No. PCT/US2003/004823.
International Search Report and Written Opinion, dated Aug. 27, 2004, in connection with Application No. PCT/US2004/004451.
International Search Report and Written Opinion, dated Apr. 15, 2005, in connection with Application No. PCT/US2004/026880.
International Search Report and Written Opinion, dated Oct. 21, 2009, in connection with Application No. PCT/US2009/035286.
International Search Report and Written Opinion, dated Jan. 31, 2005, in connection with Application No. PCT/US2004/026885.
International Search Report and Written Opinion, dated Oct. 5, 2006, in connection with Application No. PCT/US2006/015957.
International Search Report and Written Opinion, dated Mar. 21, 2006, in connection with Application No. PCT/US2005/029345.
International Search Report and Written Opinion, dated Feb. 6, 2014, in connection with Application No. PCT/US2013/075108.
International Search Report and Written Opinion, dated Sep. 20, 2012, in connection with Application No. PCT/US2012/044272.
International Search Report, dated Aug. 21, 2003, in connection with Application No. PCT/US2003/004817.
[No Author Listed] Deterministic effects and stochastic effects. Hong Kong Observatory. Last accessed on Mar. 21, 2016 and http://www.hko.gov.hk/education/dbcp/rad_health/eng/r4_1.htm. 2 pages.
[No Author Listed] http://www.biology-online.org/dictionary/Oligosaccharide. Last accessed on Mar. 20, 2008.
[No Author Listed] http://www.faqs.org/health/topics/96/Bronchodilators.html.Llast accessed on Nov. 22, 2009.
Barbry et al., [3H]phenamil binding protein of the renal epithelium Na+ channel. Purification, affinity labeling, and functional reconstitution. Biochemistry. Jan. 30, 1990;29(4):1039-45.
Barbry et al., Biochemical identification of two types of phenamil binding sites associated with amiloride-sensitive Na+ channels. Biochemistry. May 2, 1989;28(9):3744-9.
Barrett et al., Chloride secretion by the intestinal epithelium: molecular basis and regulatory aspects. Annu Rev Physiol. 2000;62:535-72.

Bennett et al., Effect of uridine 5'-triphosphate plus amiloride on mucociliary clearance in adult cystic fibrosis. Am J Respir Crit Care Med. Jun. 1996;153(6 Pt 1):1796-801.
Bicking et al., Pyrazine Diuretics. I. N-Amidino-3-amino-6-halopyrazinecarboxamides. J. Med. Chem. 1965; 8(5):638-42.
Borisy et al., Systematic discovery of multicomponent therapeutics. Proc Natl Acad Sci U S A. Jun. 24, 2003;100(13):7977-82. Epub Jun. 10, 2003.
Boucher, Airway surface dehydration in cystic fibrosis: pathogenesis and therapy. Annu Rev Med. 2007;58:157-70.
Boucher, Cystic fibrosis: a disease of vulnerability to airway surface dehydration. Trends Mol Med. Jun. 2007;13(6):231-40. Epub May 23, 2007.
Boucher, Evidence of airway surface dehydration as the initiating event in CF airway disease. J Intern Med. Jan. 2007;261(1):5-16.
Cantiello et al., Journal of Biological Chemistry. 1989;264(27):16000-7.
Chawla et al., Curr. Res. & Info. Pharm. Sci. CRIPS. 2004; 5(1): 9-12.
Cline et al., Predicting the quality of powders for inhalation from surface energy and area. Pharm Res. Sep. 2002;19(9):1274-7.
Clunes et al., Front-runners for pharmacotherapeutic correction of the airway ion transport defect in cystic fibrosis. Curr Opin Pharmacol. Jun. 2008;8(3):292-9. doi: 10.1016/j.coph.2008.04.006. Epub May 28, 2008. Author Manuscript.
Cocks et al., Amiloride analogues cause endothelium-dependent relaxation in the canine coronary artery in vitro: possible role of Na+/Ca2+ exchange. Br J Pharmacol. Sep. 1988; 95(1): 67-76.
Cohn et al., In vitro activity of amiloride combined with tobramycin against Pseudomonas isolates from patients with cystic fibrosis. Antimicrob Agents Chemother. Mar. 1988;32(3):395-6.
Cohn et al., In vitro antimicrobial activity of amiloride analogs against Pseudomonas. Chemotherapy. 1992;38(4):232-7.
Collard et al., Prevention of ventilator-associated pneumonia: an evidence-based systematic review. Ann Intern Med. Mar. 18, 2003;138(6):494-e506.
Cragoe et al., Chapter 2: An Overview of the Structure-Activity Relations in the Amiloride Series. Amiloride and its Analogs. 1992; 9-24.
Cragoe et al., Chapter 3. The Synthesis of Amiloride and its Analogs. 1992; 24-38.
Cragoe et al., Chapter 7: Diuretic Agents. Annual Reports in Medicinal Chemistry. 1965; 67-77.
Cragoe et al., Chapter 7: Diuretic Agents. Annual Reports in Medicinal Chemistry. 1966; 59-68.
Cragoe et al., Pyrazine diuretics. II. N-amidino-3-amino-5-substituted 6-halopyrazinecarboxamides. J Med Chem. Jan. 1967;10(1):66-75.
Cragoe et al., Structure-Activity Relationships in the Amiloride Series. Merck Sharp and Dohme Research Laboratories. 1979; 1-20.
Donaldson et al., Mucociliary clearance as an outcome measure for cystic fibrosis clinical research. Proc Am Thorac Soc. Aug. 1, 2007;4(4):399-405.
Donaldson et al., Mucus clearance and lung function in cystic fibrosis with hypertonic saline. N Engl J Med. Jan. 19, 2006;354(3):241-50.
Dorwald, Side Reactions in Organic Synthesis: a Guide to Successful Synthesis Design. Weinheim: Wiley-VCH Verlag GmbH & Co. KGaA, 2005, Preface.
Elkins et al., A controlled trial of long-term inhaled hypertonic saline in patients with cystic fibrosis. N Engl J Med. Jan. 19, 2006;354(3):229-40.
Epand et al., Reversal of intrinsic multidrug resistance in Chinese hamster ovary cells by amiloride analogs. Br J Cancer. Feb. 1991;63(2):247-51.
Giannakou et al., Characterization of the *Drosophila melanogaster* alkali-metal/proton exchanger (NHE) gene family. J Exp Biol. Nov. 2001;204(Pt 21):3703-16.
Giunta et al., Amiloride, a diuretic with in vitro antimicrobial activity. Pharmacol Res Commun. Aug. 1984;16(8):821-9.

(56) References Cited

OTHER PUBLICATIONS

Goralski et al., Osmolytes and ion transport modulators: new strategies for airway surface rehydration. Curr Opin Pharmacol. Jun. 2010;10(3):294-9. doi: 10.1016/j.coph.2010.04.003. Epub May 1, 2010.
Gowen et al., Increased nasal potential difference and amiloride sensitivity in neonates with cystic fibrosis. J Pediatr. Apr. 1986;108(4):517-21.
Hackam et al., Translation of research evidence from animals to humans. JAMA. Oct. 11, 2006;296(14):1731-2.
Hirsh et al., Design, synthesis, and structure-activity relationships of novel 2-substituted pyrazinoylguanidine epithelial sodium channel blockers: drugs for cystic fibrosis and chronic bronchitis. J Med Chem. Jul. 13, 2006;49(14):4098-115.
Hirsh et al., Evaluation of second generation amiloride analogs as therapy for cystic fibrosis lung disease. J Pharmacol Exp Ther. Dec. 2004;311(3):929-38. Epub Jul. 23, 2004.
Hirsh et al., Pharmacological properties of N-(3,5-diamino-6-chloropyrazine-2-carbonyl) N'-4-[4-(2,3-dihydroxypropoxy)phenyl]butyl-guanidine methanesulfonate (552-02), a novel epithelial sodium channel blacker with potential clinical efficacy for cystic fibrosis lung disease. J Pharmacol Exp Ther. Apr. 2008;325(1):77-88. doi: 10.1124/jpet.107.130443. Epub Jan. 24, 2008.
Hoffman et al., Effects of Topically Delivered Benzamil and Amiloride on Nasal Potential Difference in Cystic Fibrosis. Am, J, Resp. Crit. Care Med. 1998; 157:1844-9.
Jones et al., Pharmacokinetics of amiloride after inhalation and oral administration in adolescents and adults with cystic fibrosis. Pharmacotherapy. Mar.-Apr. 1997;17(2):263-70.
Jordan, Nature Reviews: Drug Discovery. 2003; 2:205-13.
Kellerman, P2Y(2) receptor agonists: a new class of medication targeted at improved mucociliary clearance. Chest. May 2002;121(5 Suppl):201S-205S.
Kleyman et al., Amiloride and its analogs as tools in the study of ion transport. J Membr Biol. Oct. 1988;105(1):1-21.
Kleyman et al., Distinct epitopes on amiloride. II. Variably restricted epitopes defined by monoclonal anti-amiloride antibodies. Am J Physiol. Feb. 1991;260(2 Pt 1):C271-6.
Kleyman et al., New amiloride analogue as hapten to raise anti-amiloride antibodies. Am J Physiol. Jan. 1986;250(1 Pt 1):C165-70. Abstract only.
Kleyman et al., The cellular pool of Na+ channels in the amphibian cell line A6 is not altered by mineralocorticoids. Analysis using a new photoactive amiloride analog in combination with anti-amiloride antibodies. J Biol Chem. Jul. 15, 1989;264(20):11995-2000.
Knowles et al., A pilot study of aerosolized amiloride for the treatment of lung disease in cystic fibrosis. N Engl J Med. Apr. 26, 1990;322(17):1189-94.
Knowles et al., Aerosolized amiloride as treatment of cystic fibrosis lung disease: a pilot study. Adv Exp Med Biol. 1991;290:119-28; discussion 129-32.
Knowles et al., Chapter 20. Amiloride in Cystic Fibrosis: Safety, Pharmacokinetics, and Efficacy in the Treatment of Pulmonary Disease. 1992; 301-16.
Kyle et al., Sodium channel blockers. J Med Chem. May 31, 2007;50(11):2583-8. Epub May 10, 2007.
Lammas et al., ATP-induced killing of mycobacteria by human macrophages is mediated by purinergic P2Z(P2X7) receptors. Immunity. Sep. 1997;7(3):433-44.
Li et al., Stereoselective blockade of amphibian epithelial sodium channels by amiloride analogs. J Pharmacol Exp Ther. Dec. 1993;267(3):1081-4.
Mastronarde et al., Amiloride inhibits cytokine production in epithelium infected with respiratory syncytial virus. Am J Physiol. Aug. 1996;271(2 Pt 1):L201-7.
Mentz et al., Deposition, clearance, and effects of aerosolized amiloride in sheep airways. Am Rev Respir Dis. Nov. 1986;134(5):938-43.

Olivier et al., Acute safety and effects on mucociliary clearance of aerosolized uridine 5'-triphosphate +/- amiloride in normal human adults. Am J Respir Crit Care Med. Jul. 1996;154(1):217-23.
O'Neil et al., The Merck Index. An Encyclopedia of Chemicals, Drugs, and Biologicals. 2006; 69-70.
Padmanabhan et al., Solution-phase, parallel synthesis and pharmacological evaluation of acylguanidine derivatives as potential sodium channel blockers. Bioorg Med Chem Lett. Dec. 17, 2001;11(24):3151-5.
Paisley et al., Regulation of airway mucosal hydration. Expert Rev Clin Pharmacol. May 2010;3(3):361-9. doi: 10.1586/ecp.10.19.
Rogister et al., Novel inhibitors of the sodium-calcium exchanger: benzene ring analogues of N-guanidino substituted amiloride derivatives. Eur J Med Chem. Jul.-Aug. 2001;36(7-8):597-614.
Sabater et al., Aerosolization of P2Y(2)-receptor agonists enhances mucociliary clearance in sheep. J Appl Physiol (1985). Dec. 1999;87(6):2191-6.
Shah, Chapter 7, Progress in the Treatment of Pulmonary Disease in Cystic Fibrosis. Annual Reports in Medicinal Chemistry. 2001; 36:67-78.
Shryock et al., Adenosine and adenosine receptors in the cardiovascular system: biochemistry, physiology, and pharmacology. Am J Cardiol. Jun. 19, 1997;79(12A):2-10. Abstract only.
Simchowitz et al., Chapter 2. An Overview of the Structure Activity Relations in the Amiloride Series. 1992; 9-25.
Smith et al., Chapter 7. Diuretics, Annual Reports in Medicinal Chemistry. 1978; 13:61-70.
Smith et al., Chapter 8. Diuretics, Annual Reports in Medicinal Chemistry. 1976; 11:71-9.
Sood et al., Increasing concentration of inhaled saline with or without amiloride: effect on mucociliary clearance in normal subjects. Am J Respir Crit Care Med. Jan. 15, 2003;167(2):158-63. Epub Oct. 31, 2002.
Strader et al., Structural basis of beta-adrenergic receptor function. FASEB J. May 1989;3(7):1825-32.
Strosberg et al., Structure and function of the beta 3-adrenergic receptor. Annu Rev Pharmacol Toxicol. 1997;37:421-50.
Tarran et al., Rationale for hypertonic saline therapy for cystic fibrosis lung disease. Semin Respir Crit Care Med. Jun. 2007;28(3):295-302.
Tarran et al., The CF salt controversy: in vivo observations and therapeutic approaches. Mol Cell. Jul. 2001;8(1):149-58.
Taylor et al., A Facile Route to "Open Chain" Analogues of DDATHF. Heterocycles. 1989; 28(2). 1169-78.
Thelin et al., The epithelium as a target for therapy in cystic fibrosis. Curr Opin Pharmacol. Jun. 2007;7(3):290-5. Epub May 1, 2007.
Tomkiewicz et al., Amiloride inhalation therapy in cystic fibrosis. Influence on ion content, hydration, and rheology of sputum. Am Rev Respir Dis. Oct. 1993;148(4 Pt 1):1002-7.
Velly et al., Effects of amiloride and its analogues on [3H]batrachotoxinin-A 20-alpha benzoate binding, [3H]tetracaine binding and 22Na influx. Eur J Pharmacol. Apr. 27, 1988;149(1-2):97-105.
Wark et al., Nebulised hypertonic saline for cystic fibrosis. The Cochrane Collaboration, The Cochrane Library. 2008; 4:1-35.
Windscheif et al., Substituted Dipyridlethenes and -ethynes and Key Pyridine Building Blocks. Synthesis. 1994; 87-92.
Wolff, Über Diazoanhydride (1,2,3-Oxydiazole oder Diazoxyde) and Diazoketone. Justus Liebigs Annalen der Chemie. 1913; 394: 23-59.
Worlitzsch et al., Effects of reduced mucus oxygen concentration in airway Pseudomonas infections of cystic fibrosis patients. J Clin Invest. Feb. 2002;109(3):317-36.
Yin et al., Conversion of the 2,2,6,6-tetramethylpiperidine moiety to a 2,2-dimethylpyrrolidine by cytochrome P450: evidence for a mechanism involving nitroxide radicals and heme iron. Biochemistry. May 11, 2004;43(18):5455-66.
Zhou et al., Preventive but not late amiloride therapy reduces morbidity and mortality of lung disease in betaENaC-overexpressing mice. Am J Respir Crit Care Med. Dec. 15, 2008;178(12):1245-56. doi: 10.1164/rccm.200803-442OC. Epub Oct. 10, 2008.

(56) References Cited

OTHER PUBLICATIONS

Van Goor et al., Correction of the F508del-CFTR protein processing defect in vitro by the investigational drug VX-809. Proc Natl Acad Sci U S A. Nov. 15, 2011;108(46):18843-8. doi: 10.1073/pnas.1105787108. Epub Oct. 5, 2011.

* cited by examiner

SODIUM CHANNEL BLOCKERS

RELATED APPLICATIONS

This application is a continuation of and claims priority under 35 U.S.C. § 120 to U.S. application Ser. No. 14/727,189, filed Jun. 1, 2015, which a continuation of and claims priority under 35 U.S.C. § 120 to U.S. application Ser. No. 14/158,441, filed Jan. 17, 2014, which is a continuation of and claims priority under 35 U.S.C. § 120 to U.S. application Ser. No. 13/492,711, filed Jun. 8, 2012, now granted as U.S. Pat. No. 8,846,688, which is a continuation of and claims priority under 35 U.S.C. § 120 to U.S. application Ser. No. 12/179,353, filed Jul. 24, 2008, now granted as U.S. Pat. No. 8,198,286, which is a continuation of and claims priority under 35 U.S.C. § 120 to U.S. application Ser. No. 10/532,110, filed Apr. 21, 2005, which is a national stage filing of International PCT Application No. PCT/US03/04817, filed Feb. 19, 2003, now granted as U.S. Pat. No. 6,858,615, which is a continuation-in-part of U.S. application Ser. No. 10/076,571, filed on Feb. 19, 2002, each of which is incorporated herein by reference in its entirety.

BACKGROUND OF THE INVENTION

Field of the Invention

The present invention relates to sodium channel blockers. The present invention also includes a variety of methods of treatment using these inventive sodium channel blockers.

Description of the Background

The mucosal surfaces at the interface between the environment and the body have evolved a number of "innate defense", i.e., protective mechanisms. A principal form of such innate defense is to cleanse these surfaces with liquid. Typically, the quantity of the liquid layer on a mucosal surface reflects the balance between epithelial liquid secretion, often reflecting anion ($Cl^-$ and/or $HCO_3^-$) secretion coupled with water (and a cation counter-ion), and epithelial liquid absorption, often reflecting $Na^+$ absorption, coupled with water and counter anion ($Cl^-$ and/or $HCO_3^-$). Many diseases of mucosal surfaces are caused by too little protective liquid on those mucosal surfaces created by an imbalance between secretion (too little) and absorption (relatively too much). The defective salt transport processes that characterize these mucosal dysfunctions reside in the epithelial layer of the mucosal surface.

One approach to replenish the protective liquid layer on mucosal surfaces is to "re-balance" the system by blocking $Na^+$ channel and liquid absorption. The epithelial protein that mediates the rate-limiting step of $Na^+$ and liquid absorption is the epithelial $Na^+$ channel (ENaC). ENaC is positioned on the apical surface of the epithelium, i.e. the mucosal surface-environmental interface. Therefore, to inhibit ENaC mediated $Na^+$ and liquid absorption, an ENaC blocker of the amiloride class (which blocks from the extracellular domain of ENaC) must be delivered to the mucosal surface and, importantly, be maintained at this site, to achieve therapeutic utility. The present invention describes diseases characterized by too little liquid on mucosal surfaces and "topical" sodium channel blockers designed to exhibit the increased potency, reduced mucosal absorption, and slow dissociation ("unbinding" or detachment) from ENaC required for therapy of these diseases.

Chronic bronchitis (CB), including the most common lethal genetic form of chronic bronchitis, cystic fibrosis (CF), are diseases that reflect the body's failure to clear mucus normally from the lungs, which ultimately produces chronic airways infection. In the normal lung, the primary defense against chronic intrapulmonary airways infection (chronic bronchitis) is mediated by the continuous clearance of mucus from bronchial airway surfaces. This function in health effectively removes from the lung potentially noxious toxins and pathogens. Recent data indicate that the initiating problem, i.e., the "basic defect," in both CB and CF is the failure to clear mucus from airway surfaces. The failure to clear mucus reflects an imbalance between the amount of liquid and mucin on airway surfaces. This "airway surface liquid" (ASL) is primarily composed of salt and water in proportions similar to plasma (i.e., isotonic). Mucin macromolecules organize into a well defined "mucus layer" which normally traps inhaled bacteria and is transported out of the lung via the actions of cilia which beat in a watery, low viscosity solution termed the "periciliary liquid" (PCL). In the disease state, there is an imbalance in the quantities of mucus as ASL on airway surfaces. This results in a relative reduction in ASL which leads to mucus concentration, reduction in the lubricant activity of the PCL, and a failure to clear mucus via ciliary activity to the mouth. The reduction in mechanical clearance of mucus from the lung leads to chronic bacterial colonization of mucus adherent to airway surfaces. It is the chronic retention of bacteria, the failure of local antimicrobial substances to kill mucus-entrapped bacteria on a chronic basis, and the consequent chronic inflammatory responses of the body to this type of surface infection, that lead to the syndromes of CB and CF.

The current afflicted population in the U.S. is 12,000,000 patients with the acquired (primarily from cigarette smoke exposure) form of chronic bronchitis and approximately 30,000 patients with the genetic form, cystic fibrosis. Approximately equal numbers of both populations are present in Europe. In Asia, there is little CF but the incidence of CB is high and, like the rest of the world, is increasing.

There is currently a large, unmet medical need for products that specifically treat CB and CF at the level of the basic defect that cause these diseases. The current therapies for chronic bronchitis and cystic fibrosis focus on treating the symptoms and/or the late effects of these diseases. Thus, for chronic bronchitis, β-agonists, inhaled steroids, anti-cholinergic agents, and oral theophyllines and phosphodiesterase inhibitors are all in development. However, none of these drugs treat effectively the fundamental problem of the failure to clear mucus from the lung. Similarly, in cystic fibrosis, the same spectrum of pharmacologic agents is used. These strategies have been complemented by more recent strategies designed to clear the CF lung of the DNA ("Pulmozyme"; Genentech) that has been deposited in the lung by neutrophils that have futilely attempted to kill the bacteria that grow in adherent mucus masses and through the use of inhaled antibiotics ("TOBI") designed to augment the lungs' own killing mechanisms to rid the adherent mucus plaques of bacteria. A general principle of the body is that if the initiating lesion is not treated, in this case mucus retention/obstruction, bacterial infections became chronic and increasingly refractory to antimicrobial therapy. Thus, a major unmet therapeutic need for both CB and CF lung diseases is an effective means of re-hydrating airway mucus (i.e., restoring/expanding the volume of the ASL) and promoting its clearance, with bacteria, from the lung.

R. C. Boucher, in U.S. Pat. No. 6,264,975, describes the use of pyrazinoylguanidine sodium channel blockers for hydrating mucosal surfaces. These compounds, typified by the well-known diuretics amiloride, benzamil, and phenamil, are effective. However, these compounds suffer from the significant disadvantage that they are (1) relatively impotent, which is important because the mass of drug that can be inhaled by the lung is limited; (2) rapidly absorbed, which limits the half-life of the drug on the mucosal surface; and (3) are freely dissociable from ENaC. The sum of these disadvantages embodied in these well known diuretics produces compounds with insufficient potency and/or effective half-life on mucosal surfaces to have therapeutic benefit for hydrating mucosal surfaces.

Clearly, what is needed are drugs that are more effective at restoring the clearance of mucus from the lungs of patients with CB/CF. The value of these new therapies will be reflected in improvements in the quality and duration of life for both the CF and the CB populations.

Other mucosal surfaces in and on the body exhibit subtle differences in the normal physiology of the protective surface liquids on their surfaces but the pathophysiology of disease reflects a common theme, i.e., too little protective surface liquid. For example, in xerostomia (dry mouth) the oral cavity is depleted of liquid due to a failure of the parotid sublingual and submandibular glands to secrete liquid despite continued $Na^+$ (ENaC) transport mediated liquid absorption from the oral cavity. Similarly, keratoconjunctivitis sira (dry eye) is caused by failure of lacrimal glands to secrete liquid in the face of continued $Na^+$ dependent liquid absorption on conjunctional surfaces. In rhinosinusitis, there is an imbalance, as in CB, between mucin secretion and relative ASL depletion. Finally, in the gastrointestinal tract, failure to secrete Cl— (and liquid) in the proximal small intestine, combined with increased $Na^+$ (and liquid) absorption in the terminal ileum leads to the distal intestinal obstruction syndrome (DIOS). In older patients excessive $Na^+$ (and volume) absorption in the descending colon produces constipation and diverticulitis.

Fifty million Americans and hundreds of millions of others around the world suffer from high blood pressure and the subsequent sequale leading to congestive heart failure and increasing mortality. It is the Western World's leading killer and there is a need there for new medicines to treat these diseases. Thus, in addition, some of the novel sodium channel blockers of this invention can be designed to target the kidney and as such they may be used as diuretics for the treatment of hypertension, congestive heart failure (CHF) and other cardiovascular diseases. These new agents may be used alone or in combination with beta-blockers, ACE inhibitors, HMGCoA reductase inhibitors, calcium channel blockers and other cardiovascular agents.

SUMMARY OF THE INVENTION

It is an object of the present invention to provide compounds that are more potent and/or absorbed less rapidly from mucosal surfaces, and/or are less reversible as compared to known compounds.

It is another aspect of the present invention to provide compounds that are more potent and/or absorbed less rapidly and/or exhibit less reversibility, as compared to compounds such as amilorde, benzamil, and phenamil. Therefore, the compounds will give a prolonged pharmacodynamic half-life on mucosal surfaces as compared to known compounds.

It is another object of the present invention to provide compounds which are (1) absorbed less rapidly from mucosal surfaces, especially airway surfaces, as compared to known compounds and; (2) when absorbed from musosal surfaces after administration to the mucosal surfaces, are converted in vivo into metabolic derivitives thereof which have reduced efficacy in blocking sodium channels as compared to the administered parent compound. It is another object of the present invention to provide compounds that are more potent and/or absorbed less rapidly and/or exhibit less reversibility, as compared to compounds such as amiloride, benzamil, and phenamil. Therefore, such compounds will give a prolonged pharmacodynamic half-life on mucosal surfaces as compared to previous compounds.

It is another object of the present invention to provide compounds that target the kidney for use in the treatment of cardiovascular disease.

It is another object of the present invention to provide methods of treatment that take advantage of the pharmacological properties of the compounds described above.

In particular, it is an object of the present invention to provide methods of treatment which rely on rehydration of mucosal surfaces.

In particular, it is an object of the present invention to provide methods of treating cardiovascular disease.

The objects of the present invention may be accomplished with a class of pyrazinoylguanidine compounds represented by formula (I):

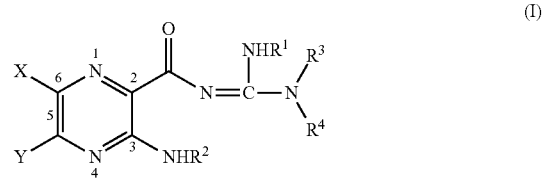

where

X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;

Y is hydrogen, hydroxyl, mercapto, lower alkoxy, lower alkyl-thio, halogen, lower alkyl, unsubstituted or substituted mononuclear aryl, or —$N(R^2)_2$;

$R^1$ is hydrogen or lower alkyl;

each $R^2$ is, independently, —$R^7$, —$(CH_2)_m$—$OR^8$, —$(CH_2)_m$—$NR^7R^{10}$, —$(CH_2)_n(CHOR^8)(CHOR^8)_n$—$CH_2OR^8$, —$(CH_2CH_2O)_m$—$R^8$, —$(CH_2CH_2O)_m$—$CH_2CH_2NR^7R^{10}$, —$(CH_2)$—$C(=O)NR^7R^{10}$, —$(CH_2)_n$—$Z_g$—$R^7$, —$(CH_2)_m$—$NR^{10}$—$CH_2(CHOR^8)(CHOR^8)$, —$CH_2OR^8$, —$(CH_2)_n$—$CO_2R^7$, or

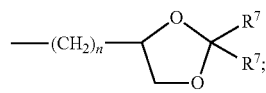

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

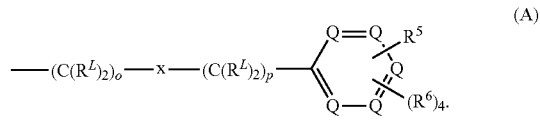

where
each $R^L$ is, independently, $-R^7$, $-(CH_2)_n-OR^8$, $-O-(CH_2)_m-OR$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_mR^8$, $-(CH_2CH_2O)_n-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

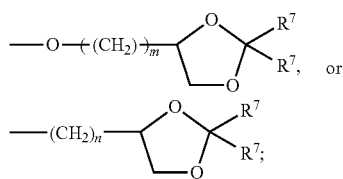

each o is, independently, an integer from 0 to 10;
each p is an integer from 0 to 10;
with the proviso that the sum of o and p in each contiguous chain is from 1 to 10;
each x is, independently, O, $NR^{10}$, C(=O), CHOH, C(=N-$R^{10}$),
$CHNR^7R^{10}$, or represents a single bond;
each $R^5$ is, independently, $-(CH_2)_m$, $-OR^8$, $-O-(CH_2)_m-OR^8$, $-(CH_2)_n-NR^7R^{10}$, $-O-(CH_2)-NR^7R^{10}$, $-(CH_2(CHOR^8)(CHOR^8)_m-CH_2OR^8$, $-O(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-(CH_2)_m-CO_2R^7$, $-O-(CH_2)_m-CO_2R^7$, $-OSO_3H$, $-O$-glucuronide, $-O$-glucose,

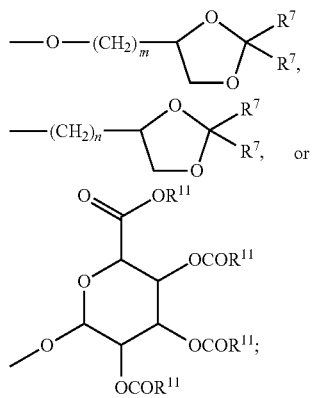

each $R^6$ is, independently, $-R^7$, $-OR^{11}$, $-N(R^7)_2$, $-(CH_2)_m-OR^8$, $-O(CH_2)_m-OR^8$, $-(CH_2)_n-NR^7R^{10}$, $-O(CH_2)_m-NR^7R^{10}$, $-(CH_2)_n(CHOR^8)(CHOR^8)_n-CH_2OR^8$, $-O-(CH_2)^m(CHOR^8)CHOR^8)_n-CH_2OR^8$, $(CH_2CH_2O)_m-R^8$, $-O(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O(CH_2)_m-CO_2R^7$, $-OSO_3H$, $-O$-glucuronide, $-O$-glucose,

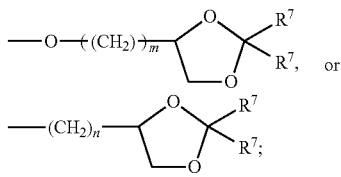

where when two $R^6$ are $-OR^{11}$ and are located adjacent to each other on a phenyl ring, the alkyl moieties of the two $R^6$ may be bonded together to form a methylenedioxy group;
each $R^7$ is, independently, hydrogen or lower alkyl;
each $R^8$ is, independently, hydrogen, lower alkyl, $-C(=O)-R^{11}$, glucuronide, 2-tetrahydropyranyl, or

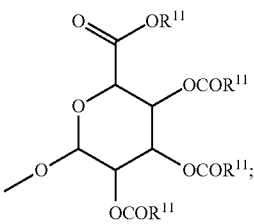

each $R^9$ is, independently, $-CO_2R^7$, $-CON(R^7)_2$, $-SO_2CH_3$, or $-C(=O)R^7$;
each $R^{10}$ is, independently, $-H$, $-SO_2CH_3$, $-CO_2R^7$, $-C(=O)NR^7R^9$, $-C(=O)R^7$, or $-CH_2-(CHOH)$, $-CH_2OH$;
each Z is, independently, CHOH, C(=O), $CHNR^7R^{10}$, C=$NR^{10}$, or $NR^{10}$;
each $R^{11}$ is, independently, lower alkyl;
each g is, independently, an integer from 1 to 6;
each m is, independently, an integer from 1 to 7;
each n is, independently, an integer from 0 to 7;
each Q is, independently, C-$R^5$, C-$R^6$, or a nitrogen atom, wherein at
most three Q in a ring are nitrogen atoms;
or a pharmaceutically acceptable salt thereof, and
inclusive of all enantiomers, diastereomers, and racemic mixtures thereof.

The present also provides pharmaceutical compositions which contain a compound described above.

The present invention also provides a method of promoting hydration of mucosal surfaces, comprising:
administering an effective amount of a compound represented by formula (I) to a mucosal surface of a subject.

The present invention also provides a method of restoring mucosal defense, comprising:
topically administering an effective amount of compound represented by formula (I) to a mucosal surface of a subject in need thereof.

The present invention also provides a method of blocking ENaC, comprising:
contacting sodium channels with an effective amount of a compound represented by formula (I).

The present invention also provides a method of promoting mucus clearance in mucosal surfaces, comprising:

administering an effective amount of a compound represented by formula (I) to a mucosal surface of a subject.

The present invention also provides a method of treating chronic bronchitis, comprising:

administering an effective amount of a compound represented by formula (I) to a subject in need thereof.

The present invention also provides a method of treating cystic fibrosis, comprising:

administering an effective amount of compound represented by formula (I) to a subject in need thereof.

The present invention also provides a method of treating rhinosinusitis, comprising:

administering an effective amount of a compound represented by a formula (I) to a subject in need thereof.

The present invention also provides a method of treating nasal dehydration, comprising:

administering an effective amount of a compound represented by formula (I) to the nasal passages of a subject in need thereof.

In a specific embodiment, the nasal dehydration is brought on by administering dry oxygen to the subject.

The present invention also provides a method of treating sinusitis, comprising:

administering an effective amount of a compound represented by formula (I) to a subject in need thereof.

The present invention also provides a method of treating pneumonia, comprising:

administering an effective amount of a compound represented by formula (I) to a subject in need thereof.

The present invention also provides a method of preventing ventilator-induced pneumonia, comprising:

administering an effective compound represented by formula (I) to a subject by means of a ventilator.

The present invention also provides a method of treating asthma, comprising:

administering an effective amount of a compound represented by formula (I) to a subject in need thereof.

The present invention also provides a method of treating primary ciliary dyskinesia, comprising:

administering an effective amount of a compound represented by formula (I) to a subject in need thereof.

The present invention also provides a method of treating otitis media, comprising:

administering an effective amount of a compound represented by formula (I) to a subject in need thereof.

The present invention also provides a method of inducing sputum for diagnostic purposes, comprising:

administering an effective amount of compound represented by formula (I) to a subject in need thereof.

The present invention also provides a method of treating chronic obstructive pulmonary disease, comprising:

administering an effective amount of a compound represented by formula (I) to a subject in need thereof.

The present invention also provides a method of treating emphysema, comprising:

administering an effective amount of a compound represented by formula (I) to a subject in need thereof.

The present invention also provides a method of treating dry eye, comprising:

administering an effective amount of a compound represented by formula (I) to the eye of the subject in need thereof.

The present invention also provides a method of promoting ocular hydration, comprising:

administering an effective amount of a compound represented by formula (I) to the eye of the subject.

The present invention also provides a method of promoting corneal hydration, comprising:

administering an effective amount of a compound represented by formula (I) to the eye of the subject.

The present invention also provides a method of treating Sjögren's disease, comprising:

administering an effective amount of compound represented by formula (I) to a subject in need thereof.

The present invention also provides a method of treating vaginal dryness, comprising:

administering an effective amount of a compound represented by formula (I) to the vaginal tract of a subject in need thereof.

The present invention also provides a method of treating dry skin, comprising:

administering an effective amount of a compound represented by formula (I) to the skin of a subject in need thereof.

The present invention also provides a method of treating dry mouth (xerostomia), comprising:

administering an effective amount of compound represented by formula (I) to the mouth of the subject in need thereof.

The present invention also provides a method of treating distal intestinal obstruction syndrome, comprising:

administering an effective amount of compound represented by formula (I) to a subject in need thereof.

The present invention also provides a method of treating esophagitis, comprising:

administering an effective amount of a compound represented by formula (I) to a subject in need thereof.

The present invention also provides a method of treating constipation, comprising:

administering an effective amount of a compound represented by formula (I) to a subject in need thereof. In one embodiment of this method, the compound is administered either orally or via a suppository or enema.

The present invention also provides a method of treating chronic diverticulitis comprising:

administering an effective amount of a compound represented by formula (I) to a subject in need thereof.

The present invention also provides a method of treating hypertension, comprising administering the compound represented by formula (I) to a subject in need thereof.

The present invention also provides a method of reducing blood pressure, comprising administering the compound represented by formula (I) to a subject in need thereof.

The present invention also provides a method of treating edema, comprising administering the compound represented by formula (I) to a subject in need thereof.

The present invention also provides a method of promoting diuresis, comprising administering the compound represented by formula (I) to a subject in need thereof.

The present invention also provides a method of promoting natriuresis, comprising administering the compound represented by formula (I) to a subject in need thereof.

The present invention also provides a method of promoting saluresis, comprising administering the compound represented by formula (I) to a subject in need thereof.

BRIEF DESCRIPTION OF THE FIGURES

A more complete appreciation of the invention and many of the attendant advantages thereof will be readily obtained as the same becomes better understood by reference to the following detailed description considered in conjunction with the following figures.

DETAILED DESCRIPTION OF THE INVENTION

Figure 1:
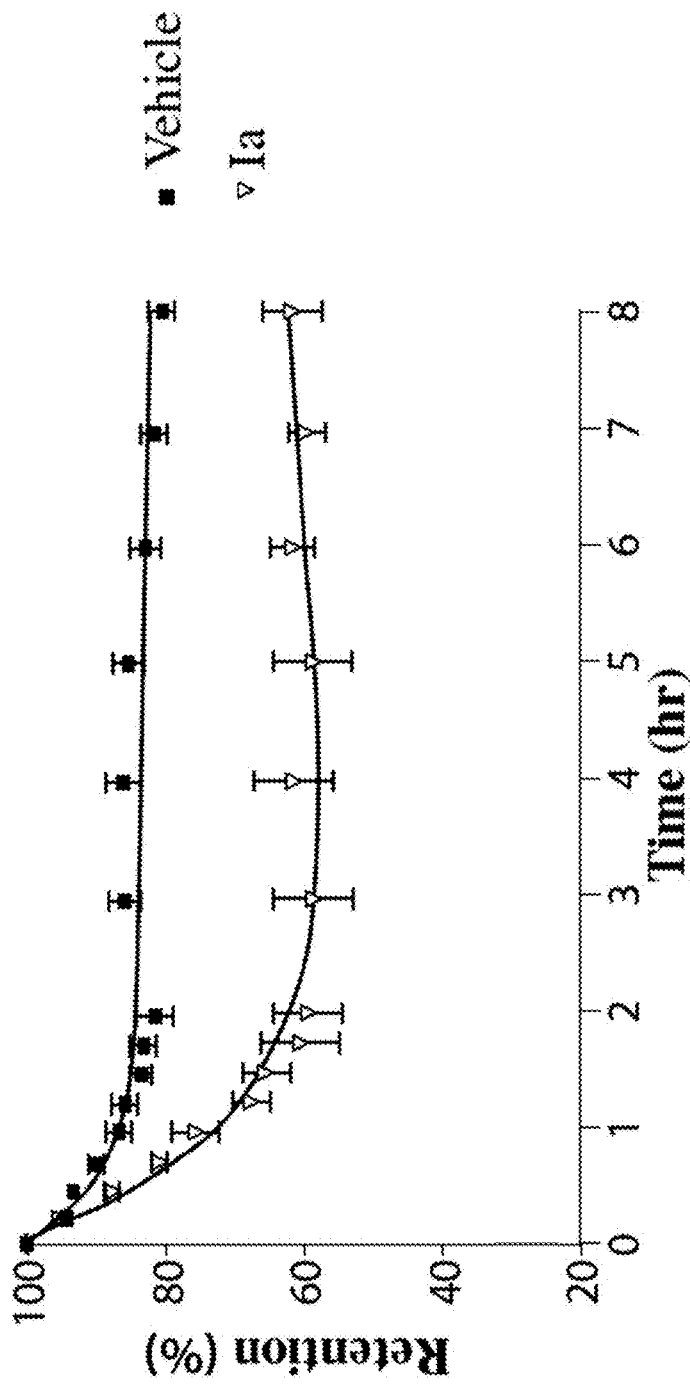
FIG. 1: Effect of a compound of the present invention on MCC at t=0 hrs as described in Example 32 herein.
Figure 2:
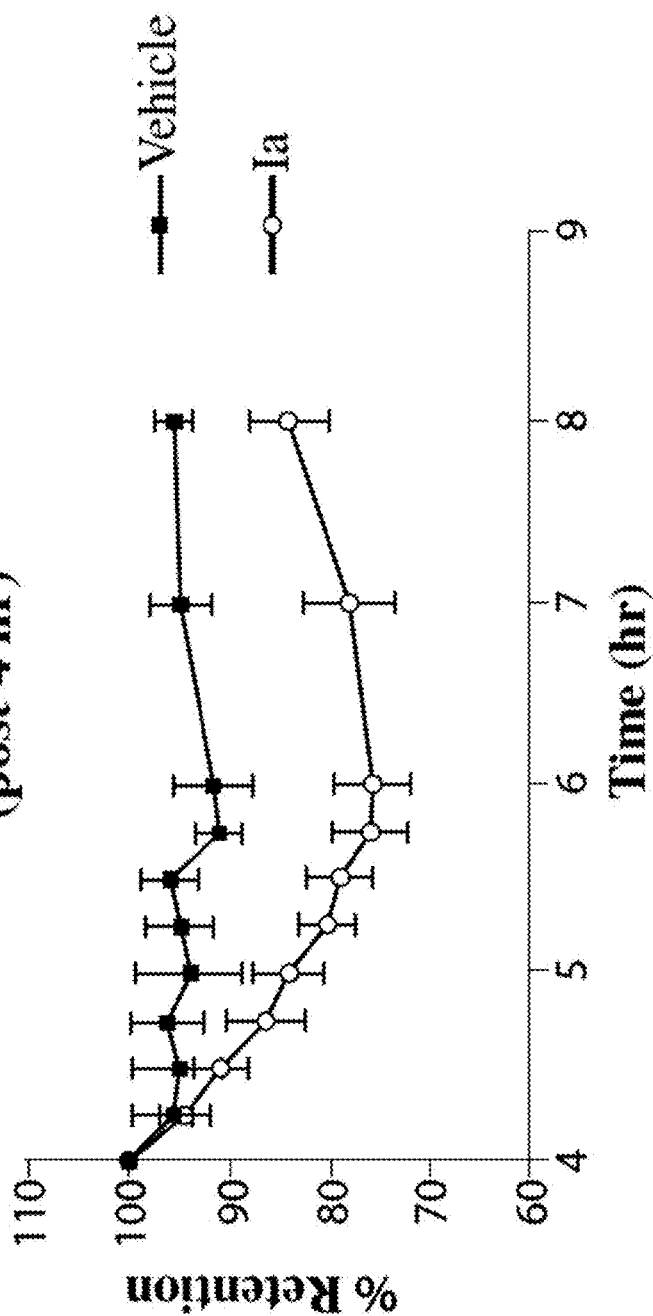
FIG. 2: Effect of a compound of the present invention on MCC at t=4 hrs as described in Example 32 herein.

The present invention is based on the discovery that the compounds of formula (I) are more potent and/or, absorbed less rapidly from mucosal surfaces, especially airway surfaces, and/or less reversible from interactions with ENaC as compared to compounds such as amiloride, benzamil, and phenamil. Therefore, the compounds of formula (I) have a longer half-life on mucosal surfaces as compared to these compounds.

The present invention is also based on the discovery that certain compounds embraced by formula (I) are converted in vivo into metabolic derivatives thereof that have reduced efficacy in blocking sodium channels as compared to the parent administered compound, after they are absorbed from mucosal surfaces after administration. This important property means that the compounds will have a lower tendency to cause undesired side-effects by blocking sodium channels located at untargeted locations in the body of the recipient, e.g., in the kidneys.

The present invention is also based on the discovery that certain compounds embraced by formula (I) target the kidney and thus may be used as cardiovascular agents.

In the compounds represented by formula (I), X may be hydrogen, halogen, trifluoromethyl, lower alkyl, lower cycloalkyl, unsubstituted or substituted phenyl, lower alkyl-thio, phenyl-lower alkyl-thio, lower alkyl-sulfonyl, or phenyl-lower alkyl-sulfonyl. Halogen is preferred.

Examples of halogen include fluorine, chlorine, bromine, and iodine. Chlorine and bromine are the preferred halogens. Chlorine is particularly preferred. This description is applicable to the term "halogen" as used throughout the present disclosure.

As used herein, the term "lower alkyl" means an alkyl group having less than 8 carbon atoms. This range includes all specific values of carbon atoms and subranges there between, such as 1, 2, 3, 4, 5, 6, and 7 carbon atoms. The term "alkyl" embraces all types of such groups, e.g., linear, branched, and cyclic alkyl groups. This description is applicable to the term "lower alkyl" as used throughout the present disclosure. Examples of suitable lower alkyl groups include methyl, ethyl, propyl, cyclopropyl, butyl, isobutyl, etc.

Substituents for the phenyl group include halogens. Particularly preferred halogen substituents are chlorine and bromine.

Y may be hydrogen, hydroxyl, mercapto, lower alkoxy, lower alkyl-thio, halogen, lower alkyl, lower cycloalkyl, mononuclear aryl, or —$N(R^2)_2$. The alkyl moiety of the lower alkoxy groups is the same as described above. Examples of mononuclear aryl include phenyl groups. The phenyl group may be unsubstituted or substituted as described above. The preferred identity of Y is —$N(R^2)_2$. Particularly preferred are such compounds where each $R^2$ is hydrogen.

$R^1$ may be hydrogen or lower alkyl. Hydrogen is preferred for $R^1$.

Each $R^2$ may be, independently, —$R^7$, —$(CH_2)_m$—$OR^8$, —$(CH_2)_m$—$NR^7R^{10}$, —$(CH_2)_n(CHOR^8)(CHOR^8)_n$—$CH_2OR^8$, —$(CH_2CH_2O)_m$—$R^8$, —$(CH_2CH_2O)_m$—$CH_2CH_2NR^7R^{10}$, —$(CH_2)_n$—$C(O)NR^7R^{10}$, —$(CH_2)_n$—$Z_g$—$R^7$, —$(CH_2)_m$—$NR^{10}$—$CH_2(CHOR^8)(CHOR^8)_n$—$CH_2OR^8$, —$(CH_2)_n$—$CO_2R^7$, or

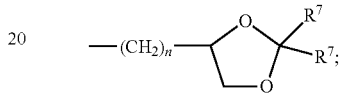

Hydrogen and lower alkyl, particularly $C_1$-$C_3$ alkyl are preferred for $R^2$. Hydrogen is particularly preferred.

$R^3$ and $R^4$ may be, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, provided that at least one of $R^3$ and $R^4$ is a group represented by formula (A).

Preferred compounds are those where one of $R^3$ and $R^4$ is hydrogen and the other is represented by formula (A).

In formula (A), the moiety —$(C(R^L)_2)_o$-x-$(C(R^L)_2)_p$— defines an alkylene group bonded to the aromatic ring. The variables o and p may each be an integer from 0 to 10, subject to the proviso that the sum of o and p in the chain is from 1 to 10. Thus, o and p may each be 0, 1, 2, 3, 4, 5, 6, 7, 8, 9, or 10. Preferably, the sum of o and p is from 2 to 6. In a particularly preferred embodiment, the sum of o and p is 4.

The linking group in the alkylene chain, x, may be, independently, O, $NR^{10}$, C(=O), CHOH, C(=N—$R^{10}$), $CHNR^7R^{10}$, or represents a single bond;

Therefore, when x represents a single bond, the alkylene chain bonded to the ring is represented by the formula —$(C(R^L)_2)_{o+p}$—, in which the sum o+p is from 1 to 10.

Each $R^L$ may be, independently, —$R^7$, —$(CH_2)_n$—$OR^8$, —O—$(CH_2)_m$—$OR^8$, —$(CH_2)_n$—$NR^7R^{10}$, —O—$(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—C(=O)$NR^7R^{10}$, —O—$(CH_2)_m$—C(=O)$NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose,

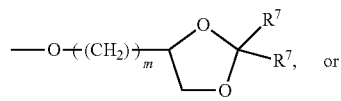

-continued

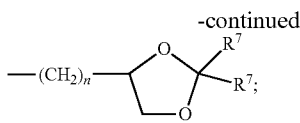

The preferred $R^L$ groups include —H, —OH, —N($R^7$)$_2$, especially where each $R^7$ is hydrogen.

In the alkylene chain in formula (A), it is preferred that when one $R^L$ group bonded to a carbon atoms is other than hydrogen, then the other $R^L$ bonded to that carbon atom is hydrogen, i.e., the formula —CHR$^L$—. It is also preferred that at most two $R^L$ groups in an alkylene chain are other than hydrogen, where in the other $R^L$ groups in the chain are hydrogens. Even more preferably, only one $R^L$ group in an alkylene chain is other than hydrogen, where in the other $R^L$ groups in the chain are hydrogens. In these embodiments, it is preferable that x represents a single bond.

In another particular embodiment of the invention, all of the $R^L$ groups in the alkylene chain are hydrogen. In these embodiments, the alkylene chain is represented by the formula

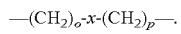

Each $R^5$ may be, independently, —(CH$_2$)$_m$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_n$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_m$—C(=O)NR$^7$R$^{10}$, —O—(CH$_2$)$_m$—C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

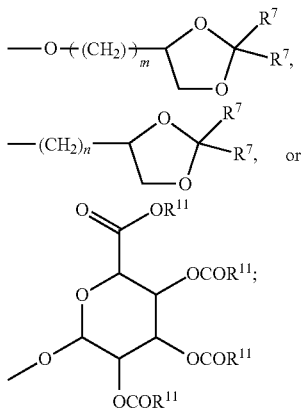

Thus, $R^5$ may be one of the following:
—(CH$_2$)$_m$—OR$^8$,
para-(CH$_2$)$_4$—OH,
—O—(CH$_2$)$_m$—OR$^8$,
para-O—(CH$_2$)$_4$—OH,
—(CH$_2$)$_n$—NR$^7$R$^{10}$,
para-NHSO$_2$CH$_3$,
para-CH$_2$NH(C=O)—(OCH$_3$)$_3$,
Para-NH(C=O)CH$_3$,
para-CH$_2$NH$_2$,
para-NH—CO$_2$C$_2$H$_5$,
para-CH$_2$NH(C=O)CH$_3$,
para-CH$_2$NHCO$_2$CH$_3$,
para-CH$_2$NHSO$_2$CH$_3$,
para-(CH$_2$)$_4$—NH(C=O)O(CH$_3$)$_3$,
para-(CH$_2$)$_4$—NH$_2$,
para-(CH$_2$)$_3$—NH(C=O)O(CH$_3$)$_3$,
para-(CH$_2$)$_3$—NH$_2$,
—O—(CH$_2$)$_m$—NR$^7$R$^{10}$,
para-OCH$_2$CH$_2$NHCO$_2$(CH$_3$)$_3$,
para-OCH$_2$CH$_2$NHCO$_2$C$_2$H$_5$,
para-O—(CH$_2$)$_3$—NH—CO$_2$—(CH$_3$)$_3$,
para-O(CH$_2$)$_3$—NH$_2$,
para-OCH$_2$CH$_2$NHSO$_2$CH$_3$,
—(CH$_2$)$_n$(CHOR$^8$)(CHOR$^8$)$_n$—CH$_2$OR$^8$,
—O—(CH$_2$)$_m$(CHOR$^8$)(CHOR$^8$)$_n$—CH$_2$OR$^8$,
para-OCH$_2$CHOHCH$_2$O-glucuronide,
para-OCH$_2$CH$_2$CHOHCH$_2$OH,
para-OCH$_2$—(α-CHOH)$_2$CH$_2$OH,
para-OCH$_2$—(CHOH)$_2$CH$_2$OH,
—(CH$_2$CH$_2$O)$_m$—R$^8$,
—O—(CH$_2$CH$_2$O)$_m$—R$^8$,
—(CH$_2$CH$_2$O)$_m$—CH$_2$CH$_2$NR$^7$R$^{10}$,
—O—(CH$_2$CH$_2$O)$_m$—CH$_2$CH$_2$NR$^7$R$^{10}$,
—(CH$_2$)$_n$—C(=O)NR$^7$R$^{10}$,
para-C(=O)NH$_2$,
—O—(CH$_2$)$_m$—C(=O)NR$^7$R$^{10}$,
—O—CH$_2$—(C=O)NHCH$_2$CHOH,
—O—CH$_2$—(C=O)NHCH$_2$CHOHCH$_2$OH,
—O—CH$_2$(C=O)NHCH$_2$(CHOH)$_2$CH$_2$OH,
—O—CH$_2$C(C=O)NHSO$_2$CH$_3$,
—O—CH$_2$(C=O)NHCO$_2$CH$_3$,
—O—CH$_2$—C(C=O)NH—C(C=O)NH$_2$,
—O—CH$_2$—(C=O)NH—(C=O)CH$_3$,
—(CH$_2$)$_n$—(Z)$_8$—R$^7$,
—(CH$_2$)$_n$—(C=N)—NH$_2$,
para-(C=NH)NH$_2$,
—(CH$_2$)$_n$—NH—C(=NH)—NH$_2$,
para-(CH$_2$)$_3$—NH—C(=NH)—NH$_2$,
para-CH$_2$NH—C(=NH)—NH$_2$,
—(CH$_2$)$_n$—CONHCH$_2$(CHOH)$_n$—CH$_2$OH,
—NH—C(=O)—CH$_2$—(CHO) CH$_2$OH,
—NH—(C=O)—NH—CH$_2$(CHOH)$_2$CHOH,
para-NHC(C=O)NHCH$_2$CH$_2$OH,
O—(CH$_2$)$_m$—(Z)$_8$—R$^7$,
—O—(CH$_2$)$_m$—NH—C(=NH)—N(R$^7$)$_2$,
para-O(CH$_2$)$_3$—NH—C(=NH)—NH$_2$,
—O—(CH$_2$)$_m$—CHNH$_2$—CO$_2$NR$^7$R$^{10}$,
para-OCH$_2$—CHNH$_2$—CO$_2$NH$_2$,
—O—(CH$_2$)$_m$—CHNH$_2$—CO$_2$NR$^7$R$^{10}$, where the compound is the (R) enantiomer,
—O—(CH$_2$)$_m$—CHNH$_2$—CO$_2$NR$^7$R$^{10}$, where the compound is the (S) enantiomer,
para-OCH$_2$CHOH—CH$_2$NHCO$_2$(CH$_3$)$_3$,
—(CH$_2$)$_n$—NR$^{10}$—CH$_2$(CHOR$^8$)(CHOR$^8$)$_n$—CH$_2$OR$^8$,
para-NHCH$_2$(CHOH)$_2$CH$_2$OH,
—O—(CH$_2$)$_m$—NR$^{10}$—CH$_2$(CHOR$^8$)(CHOR$^8$)$_n$—CH$_2$OR$^8$,
—O—(CH$_2$)$_n$—CO$_2$R$^7$,
para-OCH$_2$CH$_2$CO$_2$(CH$_3$)$_3$,
para-OCH$_2$CO$_2$H,
para-OCH$_2$CO$_2$C$_2$H$_5$,
—O—(CH$_2$)$_m$-Boc,
—(CH$_2$)$_m$—Boc,
—O—(CH$_2$)$_m$—NH—C(=NH)—N(R$^7$)$_2$,
—(CH$_2$)$_n$—NH—C(=NH)—N(R$^7$)$_2$,
—(CH$_2$)$_m$—NH—C(=O)—OR$^7$,
—O—(CH$_2$)$_m$—NH—C(=O)—OR$^7$,
—(CH$_2$)$_n$—NH—C(=O)—R$^{11}$, —O—(CH$_2$)$_m$—NH—C(=O)—R$^{11}$,
—O—(CH$_2$)$_m$—C(=O)N(R$^7$)$_2$,
—(CH$_2$)$_m$—CHOH—CH$_2$—NHBoc,
—O—(CH$_2$)—CHOH—CH$_2$—NHBoc,
—(CH$_2$)$_m$—NHC(O)OR$^7$,
—O—(CH$_2$)—NHC(O)OR$^7$,
—O—(CH$_2$)$_m$—C(=NH)—N(R$^7$)$_2$,
—(CH$_2$)$_n$—C(=NH)—N(R$^7$)$_2$.

In another embodiment, R$^5$ is selected from the group consisting of —O—(CH$_2$)$_3$—OH. —NH$_2$, —O—CH$_2$—(CHOH)$_2$—CH$_2$OH—O—CH$_2$—CHOH—CH$_2$OH, —O—CH$_2$CH$_2$—O-tetrahydropyran-2-yl, —O—CH$_2$CHOH—CH$_2$—O-glucuronide, —O—CH$_2$CH$_2$OH, —O—(CH$_2$CH$_2$O)$_4$—CH$_3$, —O—CH$_2$CH$_2$OCH$_3$, —O—CH$_2$—(CHOC(=O)CH$_3$)—CH$_2$—OC(=O)CH$_3$, —O—(CH$_2$CH$_2$O)$_2$—CH$_3$, —OCH$_2$—CHOH—CHOH—CH$_2$OH, —CH$_2$OH, —CO$_2$CH$_3$,

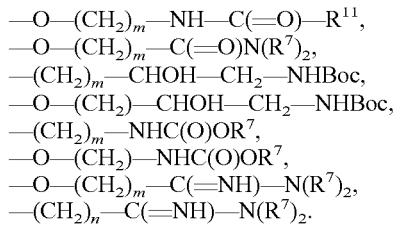

In another embodiment, R$^5$ is selected from the group consisting of para —O—(CH$_2$)$_3$—OH, para —NH$_2$, para —O—CH$_2$—(CHOH)$_2$—CH$_2$OH, ortho —O—CH$_2$—CHOH—CH$_2$OH, meta —O—CH$_2$—CHOH—CH$_2$OH, para —O—CH$_2$CH$_2$—O-tetrahydropyran-2-yl, para —O—CH$_2$CHOH—CH$_2$—O-glucuronide, para —O—CH$_2$CH$_2$OH, para —O—(CH$_2$CH$_2$O)$_4$—CH$_3$, para —O—CH$_2$CH$_2$OCH$_3$, para —O—CH$_2$—(CHOC(=O)CH$_3$)—CH$_2$—OC(=O)CH$_3$, para. —O—(CH$_2$CH$_2$O)$_2$—CH$_3$, —OCH$_2$—CHOH—CHOH—CH$_2$OH, para —CH$_2$OH, para —CO$_2$CH$_3$, para —SO$_3$H, para —O-glucuronide, para

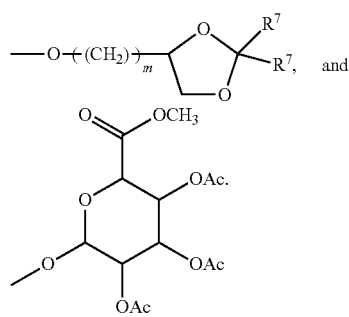

In a preferred embodiment, each —(CH$_2$)$_n$—(Z)$_g$—R$^7$ falls within the scope of the structures described above and is, independently,
—(CH$_2$)$_n$—(C=N)—NH$_2$.
—(CH$_2$)$_n$—NH—C(=NH)NH$_2$,
—(CH$_2$)$_n$—CONHCH$_2$(CHOH)$_n$—CH$_2$OH, or
—NH—C(=O)—CH$_2$—(CHOH)$_n$CH$_2$OH.

In another a preferred embodiment, each —O—(CH$_2$)$_m$—(Z)$_g$—R$^7$ falls within the scope of the structures described above and is, independently,
—O—(CH$_2$)$_m$—NH—C(=NH)—N(R$^7$)$_2$, or
—O—(CH$_2$)$_m$—CHNH$_2$—CO$_2$NR$^7$R$^{10}$.

In another preferred embodiment, R$^5$ may be one of the following:
—O—CH$_2$CHOHCH$_2$O-glucuronide,
—OCH$_2$CHOHCH$_3$,
—OCH$_2$CH$_2$NH$_2$,
—OCH$_2$CH$_2$NHCO(CH$_3$)$_3$,
—CH$_2$CH$_2$OH,
—OCH$_2$CH$_2$OH,
—O—(CH$_2$)$_m$-Boc,
—(CH$_2$)$_m$-Boc,
—OCH$_2$CH$_2$OH,
—OCH$_2$CO$_2$H,
—O—(CH$_2$) m-NH—C(=NH)—N(R$^7$)$_2$,
—(CH$_2$)$_n$—NH—C(=NH)—N(R$^7$)$_2$,
—NHCH$_2$(CHOH)$_2$—CH$_2$OH,
—OCH$_2$CO$_2$Et,
—NHSO$_2$CH$_3$,
—(CH$_2$)$_m$—NH—C(=O)—OR$^7$,
—O—(CH$_2$)$_m$—NH—C(=O)—OR$^7$,
—(CH$_2$)$_n$—NH—C(=O)—R$^{11}$,
—O—(CH$_2$)$_m$—NH—C(=O)—R$^{11}$,
—O—CH$_2$C(=O)NH$_2$,
—CH$_2$NH$_2$,
—NHCO$_2$Et,
—OCH$_2$CH$_2$CH$_2$OH,
—CH$_2$NHSO$_2$CH$_3$,
—OCH$_2$CH$_2$CHOHCH$_2$OH,
—OCH$_2$CH$_2$NHCO$_2$Et,
—NH—C(=NH$_2$)—NH$_2$,
—OCH$_2$—(α-CHOH)$_2$—CH$_2$OH
—OCH$_2$CHOHCH$_2$NH$_2$,
—(CH$_2$)$_m$—CHOH—CH$_2$—NHBoc,
—O—(CH$_2$)$_m$—CHOH—CH$_2$—NHBoc,
—(CH$_2$)$_m$—NHC(O)OR$^7$,
—O—(CH$_2$)$_m$—NHC(O)OR$^7$.
—OCH$_2$CH$_2$CH$_2$NH$_2$,
—OCH$_2$CH$_2$NHCH$_2$(CHOH)$_2$CH$_2$OH,
—OCH$_2$CH$_2$NH(CH$_2$[(CHOH)$_2$CH$_2$OH)]$_2$,
—(CH$_2$)$_4$—NHBoc,
—(CH$_2$)$_4$—NH$_2$,
—(CH$_2$)$_4$—OH,
—OCH$_2$CH$_2$NHSO$_2$CH$_3$,
—O—(CH$_2$)$_m$—C(=NH)—N(R$^7$)$_2$,
—(CH$_2$)$_n$—C(=NH)—N(R$^7$)$_2$,
—(CH$_2$)$_3$—NHBoc,
—(CH$_2$)$_3$NH$_2$,
—O—(CH$_2$)$_m$—NH—NH—C(=NH)—N(R$^7$)$_2$,
—(CH$_2$)$_n$—NH—NH—C(=NH)—N(?R$^7$)$_2$, or
—O—CH$_2$—CHOH—CH$_2$—NH—C(=NH)—N(R$^7$)$_2$;

There are four R$^6$ groups present on the ring in formula (A). Each R$^6$ may be each, independently, —R$^7$, —OR$^{11}$, —N(R$^7$)$_2$, —(CH$_2$)$_m$—OR$^8$,
—O—(CH$_2$)$_m$—OR$^8$, —(CH$_2$)$_n$—NR$^7$R$^{10}$, —O—(CH$_2$)$_m$—NR$^7$R$^{10}$,
—(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$,
—(CH$_2$CH$_2$O)$_m$—R$^8$, —O—(CH$_2$CH$_2$O)$_m$—R$^8$,
—(CH$_2$CH$_2$O)$_m$—CH$_2$CH$_2$NR$^7$R$^{10}$,
—O(CH$_2$CH$_2$O)$_m$—CH$_2$CH$_2$NR$^7$R$^{10}$, —(CH$_2$)$_n$—C(=O)NR$^7$R$^{10}$,
—O(CH$_2$)$_m$—C(=O)NR$^7$R$^{10}$, —(CH$_2$)$_n$—(Z)$_g$—R$^7$,
—O—(CH$_2$)$_m$—(Z)$^g$—R$^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose, or

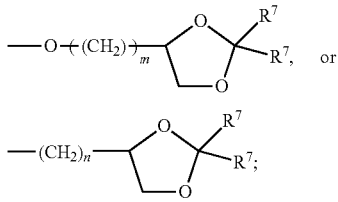

In addition, one of more of the $R^6$ groups can be one of the $R^5$ groups which fall within the broad definition of $R^6$ set forth above.

When two $R^6$ are —$OR^{11}$ and are located adjacent to each other on a phenyl ring, the alkyl moieties of the two $R^6$ groups may be bonded together to form a methylenedioxy group, i.e., a group of the formula —O—$CH_2$—O—.

As discussed above, $R^6$ may be hydrogen. Therefore, 1, 2, 3, or 4 $R^6$ groups may be other than hydrogen. Preferably at most 3 of the $R^6$ groups are other than hydrogen.

Each g is, independently, an integer from 1 to 6. Therefore, each g may be 1, 2, 3, 4, 5, or 6.

Each m is an integer from 1 to 7. Therefore, each m may be 1, 2, 3, 4, 5, 6, or 7.

Each n is an integer from 0 to 7. Therefore, each n may be 0, 1, 2, 3, 4, 5, 6, or 7.

Each Q in formula (A) is C—$R^5$, C—$R^6$, or a nitrogen atom, where at most three Q in a ring are nitrogen atoms. Thus, there may be 1, 2, or 3 nitrogen atoms in a ring. Preferably, at most two Q are nitrogen atoms. More preferably, at most one Q is a nitrogen atom. In one particular embodiment, the nitrogen atom is at the 3-position of the ring. In another embodiment of the invention, each Q is either C—$R^5$ or C—$R^6$, i.e., there are no nitrogen atoms in the ring.

More specific examples of suitable groups represented by formula (A) are shown in formulas (B)-(E) below:

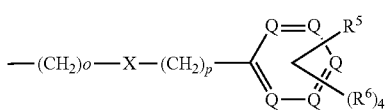
(B)

where o, x, p, $R^5$, and $R^6$, are as defined above;

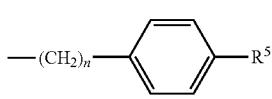
(C)

where n is an integer from 1 to 10 and $R^5$ is as defined above;

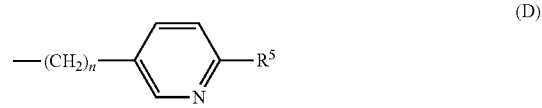
(D)

where n is an integer from 1 from 10 and $R^5$ is as defined above;

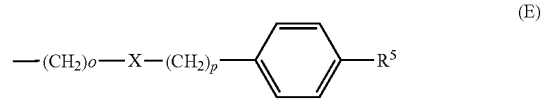
(E)

where o, x, p, and $R^5$ are as defined above.

In a preferred embodiment of the invention, Y is —$NH_2$.
In another preferred embodiment, $R^2$ is hydrogen.
In another preferred embodiment, $R^1$ is hydrogen.
In another preferred embodiment, X is chlorine.
In another preferred embodiment, $R^3$ is hydrogen.
In another preferred embodiment, $R^L$ is hydrogen.
In another preferred embodiment, o is 4.
In another preferred embodiment, p is 0.
In another preferred embodiment, the sum of o and p is 4.
In another preferred embodiment, x represents a single bond.
In another preferred embodiment, $R^6$ is hydrogen.
In another preferred embodiment, at most one Q is a nitrogen atom.
In another preferred embodiment, no Q is a nitrogen atom.
In a preferred embodiment of the present invention:
X is halogen;
Y is —$N(R^7)_2$;
$R^1$ is hydrogen or $C_1$-$C_3$ alkyl;
$R^2$ is —$R^7$, —$OR^7$, $CH_2OR^7$, or —$CO_2R^7$;
$R^3$ is a group represented by formula (A); and
$R^4$ is hydrogen, a group represented by formula (A), or lower alkyl;
In another preferred embodiment of the present invention:
X is chloro or bromo;
Y is —$N(R^7)_2$;
$R^2$ is hydrogen or $C_1$-$C_3$ alkyl;
at most three $R^6$ are other than hydrogen as described above;
at most three $R^L$ are other than hydrogen as described above; and
at most 2 Q are nitrogen atoms.
In another preferred embodiment of the present invention:
Y is —$NH_2$;
In another preferred embodiment of the present invention:
$R^4$ is hydrogen;
at most one $R^L$ is other than hydrogen as described above;
at most two $R^6$ are other than hydrogen as described above; and
at most 1 Q is a nitrogen atom.

The compounds of formula (I) may be prepared and used as the free base. Alternatively, the compounds may be prepared and used as a pharmaceutically acceptable salt. Pharmaceutically acceptable salts are salts that retain or enhance the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid and the like; and (c) salts formed from elemental anions for example, chlorine, bromine, and iodine.

It is to be noted that all enantiomers, diastereomers, and racemic mixtures of compounds within the scope of formula (I) are embraced by the present invention. All mixtures of such enantiomers and diastereomers are within the scope of the present invention.

Without being limited to any particular theory, it is believed that the compounds of formula (I) function in vivo as sodium channel blockers. By blocking epithelial sodium channels present in mucosal surfaces the compounds of formula (I) reduce the absorption of water by the mucosal surfaces. This effect increases the volume of protective liquids on mucosal surfaces, rebalances the system, and thus treats disease.

The present invention also provides methods of treatment that take advantage of the properties of the compounds of formula (I) discussed above. Thus, subjects that may be treated by the methods of the present invention include, but are not limited to, patients afflicted with cystic fibrosis, primary ciliary dyskinesia, chronic bronchitis, chronic obstructive airway disease, artificially ventilated patients, patients with acute pneumonia, etc. The present invention may be used to obtain a sputum sample from a patient by administering the active compounds to at least one lung of a patient, and then inducing or collecting a sputum sample from that patient. Typically, the invention will be administered to respiratory mucosal surfaces via aerosol (liquid or dry powders) or lavage.

Subjects that may be treated by the method of the present invention also include patients being administered supplemental oxygen nasally (a regimen that tends to dry the airway surfaces); patients afflicted with an allergic disease or response (e.g., an allergic response to pollen, dust, animal hair or particles, insects or insect particles, etc.) that affects nasal airway surfaces; patients afflicted with a bacterial infection e.g., staphylococcus infections such as Staphylococcus aureus infections, Hemophilus influenza infections, Streptococcus pneumoniae infections, Pseudomonas aeuriginosa infections, etc.) of the nasal airway surfaces; patients afflicted with an inflammatory disease that affects nasal airway surfaces; or patients afflicted with sinusitis (wherein the active agent or agents are administered to promote drainage of congested mucous secretions in the sinuses by administering an amount effective to promote drainage of congested fluid in the sinuses), or combined, Rhinosinusitis. The invention may be administered to rhinosinal surfaces by topical delivery, including aerosols and drops.

The present invention may be used to hydrate mucosal surfaces other than airway surfaces. Such other mucosal surfaces include gastrointestinal surfaces, oral surfaces, genito-urethral surfaces, ocular surfaces or surfaces of the eye, the inner ear and the middle ear. For example, the active compounds of the present invention may be administered by any suitable means, including locally/topically, orally, or rectally, in an effective amount.

The compounds of the present invention are also useful for treating a variety of functions relating to the cardiovascular system. Thus, the compounds of the present invention are useful for use as antihypertensive agents. The compounds may also be used to reduce blood pressure and to treat edema. In addition, the compounds of the present invention are also useful for promoting diuresis, natriuresis, and saluresis. The compounds may be used alone or in combination with beta blockers, ACE inhibitors, HMGCoA reductase inhibitors, calcium channel blockers and other cardiovascular agents to treat hypertension, congestive heart failure and reduce cardiovascular mortality.

The present invention is concerned primarily with the treatment of human subjects, but may also be employed for the treatment of other mammalian subjects, such as dogs and cats, for veterinary purposes.

As discussed above, the compounds used to prepare the compositions of the present invention may be in the form of a pharmaceutically acceptable free base. Because the free base of the compound is generally less soluble in aqueous solutions than the salt, free base compositions are employed to provide more sustained release of active agent to the lungs. An active agent present in the lungs in particulate form which has not dissolved into solution is not available to induce a physiological response, but serves as a depot of bioavailable drug which gradually dissolves into solution.

Another aspect of the present invention is a pharmaceutical composition, comprising a compound of formula (I) in a pharmaceutically acceptable carrier (e.g., an aqueous carrier solution). In general, the compound of formula (I) is included in the composition in an amount effective to inhibit the reabsorption of water by mucosal surfaces.

The compounds of the present invention may also be used in conjunction with a P2Y2 receptor agonist or a pharmaceutically acceptable salt thereof (also sometimes referred to as an "active agent" herein). The composition may further comprise a P2Y2 receptor agonist or a pharmaceutically acceptable salt thereof (also sometimes referred to as an "active agent" herein). The P2Y2 receptor agonist is typically included in an amount effective to stimulate chloride and water secretion by airway surfaces, particularly nasal airway surfaces. Suitable P2Y2 receptor agonists are described in columns 9-10 of U.S. Pat. Nos. 6,264,975, 5,656,256, and 5,292,498, each of which is incorporated herein by reference.

Bronchodiloators can also be used in combination with compounds of the present invention. These bronchodilators include, but are not limited to, β-adrenergic agonists including but not limited to epinephrine, isoproterenol, fenoterol, albutereol, terbutalin, pirbuterol, bitolterol, metaproterenol, iosetharine, salmeterol xinafoate, as well as anticholinergic agents including but not limited to ipratropium bromide, as well as compounds such as theophylline and aminophylline. These compounds may be administered in accordance with known techniques, either prior to or concurrently with the active compounds described herein.

Another aspect of the present invention is a pharmaceutical formulation, comprising an active compound as described above in a pharmaceutically acceptable carrier (e.g., an aqueous carrier solution). In general, the active compound is included in the composition in an amount effective to treat mucosal surfaces, such as inhibiting the reabsorption of water by mucosal surfaces, including airway and other surfaces.

The active compounds disclosed herein may be administered to mucosal surfaces by any suitable means, including topically, orally, rectally, vaginally, ocularly and dermally, etc. For example, for the treatment of constipation, the active compounds may be administered orally or rectally to the gastrointestinal mucosal surface. The active compound may be combined with a pharmaceutically acceptable carrier in any suitable form, such as sterile physiological or dilute saline or topical solution, as a droplet, tablet or the like for oral administration, as a suppository for rectal or genitourethral administration, etc. Excipients may be included in the formulation to enhance the solubility of the active compounds, as desired.

The active compounds disclosed herein may be administered to the airway surfaces of a patient by any suitable means, including as a spray, mist, or droplets of the active compounds in a pharmaceutically acceptable carrier such as physiological or dilute saline solutions or distilled water. For example, the active compounds may be prepared as formulations and administered as described in U.S. Pat. No. 5,789,391 to Jacobus, the disclosure of which is incorporated by reference herein in its entirety.

Solid or liquid particulate active agents prepared for practicing the present invention could, as noted above, include particles of respirable or non-respirable size; that is, for respirable particles, particles of a size sufficiently small to pass through the mouth and larynx upon inhalation and into the bronchi and alveoli of the lungs, and for non-respirable particles, particles sufficiently large to be retained in the nasal airway passages rather than pass through the larynx and into the bronchi and alveoli of the lungs. In general, particles ranging from about 1 to 5 microns in size (more particularly, less than about 4.7 microns in size) are respirable. Particles of non-respirable size are greater than about 5 microns in size, up to the size of visible droplets. Thus, for nasal administration, a particle size in the range of 10-500 µm may be used to ensure retention in the nasal cavity.

In the manufacture of a formulation according to the invention, active agents or the physiologically acceptable salts or free bases thereof are typically admixed with, inter alia, an acceptable carrier. Of course, the carrier must be compatible with any other ingredients in the formulation and must not be deleterious to the patient. The carrier must be solid or liquid, or both, and is preferably formulated with the compound as a unit-dose formulation, for example, a capsule, that may contain 0.5% to 99% by weight of the active compound. One or more active compounds may be incorporated in the formulations of the invention, which formulations may be prepared by any of the well-known techniques of pharmacy consisting essentially of admixing the components.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate active agent composition may optionally contain a dispersant which serves to facilitate the formulation of an aerosol. A suitable dispersant is lactose, which may be blended with the active agent in any suitable ratio (e.g., a 1 to 1 ratio by weight).

Active compounds disclosed herein may be administered to airway surfaces including the nasal passages, sinuses and lungs of a subject by a suitable means know in the art, such as by nose drops, mists, etc. In one embodiment of the invention, the active compounds of the present invention and administered by transbronchoscopic lavage. In a preferred embodiment of the invention, the active compounds of the present invention are deposited on lung airway surfaces by administering an aerosol suspension of respirable particles comprised of the active compound, which the subject inhales. The respirable particles may be liquid or solid. Numerous inhalers for administering aerosol particles to the lungs of a subject are known.

Inhalers such as those developed by Inhale Therapeutic Systems, Palo Alto, Calif., USA, may be employed, including but not limited to those disclosed in U.S. Pat. Nos. 5,740,794; 5,654,007; 5,458,135; 5,775,320; and 5,785,049, each of which is incorporated herein by reference. The Applicant specifically intends that the disclosures of all patent references cited herein be incorporated by reference herein in their entirety. Inhalers such as those developed by Dura Pharmaceuticals, Inc., San Diego, Calif., USA, may also be employed, including but not limited to those disclosed in U.S. Pat. Nos. 5,622,166; 5,577,497; 5,645,051; and 5,492,112, each of which is incorporated herein by reference. Additionally, inhalers such as those developed by Aradigm Corp., Hayward, Calif., USA, may be employed, including but not limited to those disclosed in U.S. Pat. Nos. 5,826,570; 5,813,397; 5,819,726; and 5,655,516, each of which is incorporated herein by reference. These apparatuses are particularly suitable as dry particle inhalers.

Aerosols of liquid particles comprising the active compound may be produced by any suitable means, such as with a pressure-driven aerosol nebulizer or an ultrasonic nebulizer. See, e.g., U.S. Pat. No. 4,501,729, which is incorporated herein by reference. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or dilute aqueous alcoholic solution. Perfluorocarbon carriers may also be used. Optional additives include preservatives if the formulation is not made sterile, for example, methyl hydroxybenzoate, antioxidants, flavoring agents; volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing predetermined metered dose of medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of powder blend comprising the active ingredient, a suitable powder diluent, such as lactose, and an optional surfactant. The active ingredient typically comprises of 0.1 to 100% w/w of the formulation. A second type of illustrative aerosol generator comprises a metered dose inhaler. Metered dose inhalers are pressurized aerosol dispensers, typically containing a suspension or solution formulation of active ingredient in a liquified propellant. During use, these devices discharge the formulation through a valve adapted to deliver a metered volume, typically from 10 to 150 μl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one of more co-solvents, for example, ethanol, surfactants, such as oleic acid or sorbitan trioleate, antioxidants and suitable flavoring agents.

The aerosol, whether formed from solid or liquid particles, may be produced by the aerosol generator at a rate of from about 10 to 150 liters per minute, more preferable from 30 to 150 liters per minute, and most preferably about 60 liters per minute. Aerosols containing greater amounts of medicament may be administered more rapidly.

The dosage of the active compounds disclosed herein will vary depending on the condition being treated and the state of the subject, but generally may be from about 0.01, 0.03, 0.05, 0.1 to 1, 5, 10 or 20 mg of the pharmaceutic agent, deposited on the airway surfaces. The daily dose may be divided among one or multiple unit dose administrations. The goal is to achieve a concentration of the pharmaceutic agents on lung airway surfaces of between $10^{-9}$-$10^{4}$ M.

In another embodiment, they are administered by administering an aerosol suspension of respirable or non-respirable particles (preferably non-respirable particles) comprised of active compound, which the subject inhales through the nose. The respirable or non-respirable particles may be liquid or solid. The quantity of active agent included may be an amount of sufficient to achieve dissolved concentrations of active agent on the airway surfaces of the subject of from about $10^{-9}$, $10^{-8}$, or $10^{-7}$ to about $10^{-3}$, $10^{-2}$, $10^{-1}$ moles/liter, and more preferably from about $10^{-9}$ to about $10^{-4}$ moles/liter.

The dosage of active compound will vary depending on the condition being treated and the state of the subject, but generally may be an amount sufficient to achieve dissolved concentrations of active compound on the nasal airway surfaces of the subject from about $10^{-9}$, $10^{-8}$, $10^{-7}$ to about $10^{-3}$, $10^{-2}$, or $10^{-1}$ moles/liter, and more preferably from about $10^{-7}$ to about $10^{-4}$ moles/liter. Depending upon the solubility of the particular formulation of active compound administered, the daily dose may be divided among one or several unit dose administrations. The daily dose by weight may range from about 0.01, 0.03, 0.1, 0.5 or 1.0 to 10 or 20 milligrams of active agent particles for a human subject, depending upon the age and condition of the subject. A currently preferred unit dose is about 0.5 milligrams of active agent given at a regimen of 2-10 administrations per day. The dosage may be provided as a prepackaged unit by any suitable means (e.g., encapsulating a gelatin capsule).

In one embodiment of the invention, the particulate active agent composition may contain both a free base of active agent and a pharmaceutically acceptable salt to provide both early release and sustained release of active agent for dissolution into the mucus secretions of the nose. Such a composition serves to provide both early relief to the patient, and sustained relief over time. Sustained relief, by decreasing the number of daily administrations required, is expected to increase patient compliance with the course of active agent treatments.

Pharmaceutical formulations suitable for airway administration include formulations of solutions, emulsions, suspensions and extracts. See generally, J. Nairn, Solutions, Emulsions, Suspensions and Extracts, in Remington: The Science and Practice of Pharmacy, chap. 86 ($19^{th}$ ed. 1995), incorporated herein by reference. Pharmaceutical formulations suitable for nasal administration may be prepared as described in U.S. Pat. No. 4,389,393 to Schor; U.S. Pat. No. 5,707,644 to Illum; U.S. Pat. No. 4,294,829 to Suzuki; and U.S. Pat. No. 4,835,142 to Suzuki, the disclosures of which are incorporated by reference herein in their entirety.

Mists or aerosols of liquid particles comprising the active compound may be produced by any suitable means, such as by a simple nasal spray with the active agent in an aqueous pharmaceutically acceptable carrier, such as a sterile saline solution or sterile water. Administration may be with a pressure-driven aerosol nebulizer or an ultrasonic nebulizer. See e.g. U.S. Pat. Nos. 4,501,729 and 5,656,256, both of which are incorporated herein by reference. Suitable formulations for use in a nasal droplet or spray bottle or in nebulizers consist of the active ingredient in a liquid carrier, the active ingredient comprising up to 40% w/w of the formulation, but preferably less than 20% w/w. Typically the carrier is water (and most preferably sterile, pyrogen-free water) or dilute aqueous alcoholic solution, preferably made in a 0.12% to 0.8% solution of sodium chloride. Optional additives include preservatives if the formulation is not made sterile, for example, methyl hydroxybenzoate, antioxidants, flavoring agents, volatile oils, buffering agents, osmotically active agents (e.g. mannitol, xylitol, erythritol) and surfactants.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate composition may optionally contain a dispersant which serves to facilitate the formation of an aerosol. A suitable dispersant is lactose, which may be blended with the active agent in any suitable ratio (e.g., a 1 to 1 ratio by weight).

The compounds of formula (I) may be synthesized according to procedures known in the art. A representative synthetic procedure is shown in the scheme below:

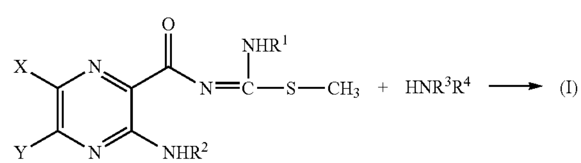

These procedures are described in, for example, E. J. Cragoe, "The Synthesis of Amiloride and Its Analogs" (Chapter 3) in *Amiloride and Its Analogs*, pp. 25-36, incorporated herein by reference. Other methods of preparing the compounds are described in, for example, U.S. Pat. No. 3,313,813, incorporated herein by reference. See in particular Methods A, B, C, and D described in U.S. Pat. No. 3,313,813. Several assays may be used to characterize the compounds of the present invention. Representative assays are discussed below.

In Vitro Measure of Sodium Channel Blocking Activity and Reversibility

One assay used to assess mechanism of action and/or potency of the compounds of the present invention involves the determination of lumenal drug inhibition of airway epithelial sodium currents measured under short circuit current ($I_{SC}$) using airway epithelial monolayers mounted in Ussing chambers. Cells obtained from freshly excised human, dog, sheep or rodent airways are seeded onto porous 0.4 micron Snapwell™ Inserts (CoStar), cultured at air-liquid interface (ALI) conditions in hormonally defined media, and assayed for sodium transport activity ($I_{SC}$) while bathed in Krebs Bicarbonate Ringer (KBR) in Using chambers. All test drug additions are to the lumenal bath with half-log dose addition protocols (from $1 \times 10^{-11}$ M to $3 \times 10^{-5}$ M), and the cumulative change in $I_{SC}$ (inhibition) recorded. All drugs are prepared in dimethyl sulfoxide as stock solutions at a concentration of $1 \times 10^{-2}$ M and stored at $-20°$ C. Eight preparations are typically run in parallel; two preparations per run incorporate amiloride and/or benzamil as positive controls. After the maximal concentration ($5 \times 10^{-5}$ M) is administered, the lumenal bath is exchanged three times with fresh drug-free KBR solution, and the resultant $I_{SC}$ measured after each wash for approximately 5 minutes in duration. Reversibility is defined as the percent return to the baseline value for sodium current after the third wash. All data from the voltage clamps are collected via a computer interface and analyzed off-line.

Dose-effect relationships for all compounds are considered and analyzed by the Prism 3.0 program. $IC_{50}$ values, maximal effective concentrations, and reversibility are calculated and compared to amiloride and benzamil as positive controls.

Pharmacological Assays of Absorption (1) Apical Disappearance Assay

Bronchial cells (dog, human, sheep, or rodent cells) are seeded at a density of $0.25 \times 10^6/cm^2$ on a porous Transwell-Col collagen-coated membrane with a growth area of 1.13 $cm^2$ grown at an air-liquid interface in hormonally defined media that promotes a polarized epithelium. From 12 to 20 days after development of an air-liquid interface (ALI) the cultures are expected to be >90% ciliated, and mucins will accumulate on the cells. To ensure the integrity of primary airway epithelial cell preparations, the transepithelial resistance ($R_t$) and transepithelial potential differences (PD), which are indicators of the integrity of polarized nature of the culture, are measured. Human cell systems are preferred for studies of rates of absorption from apical surfaces. The disappearance assay is conducted under conditions that mimic the "thin" films in vivo (~25 μl) and is initiated by adding experimental sodium channel blockers or positive controls (amiloride, benzamil, phenamil) to the apical surface at an initial concentration of 10 μM. A series of samples (5 μl volume per sample) is collected at various time points, including 0, 5, 20, 40, 90 and 240 minutes. Concentrations are determined by measuring intrinsic fluorescence of each sodium channel blocker using a Fluorocount Microplate Flourometer or HPLC. Quantitative analysis employs a standard curve generated from authentic reference standard materials of known concentration and purity. Data analysis of the rate of disappearance is performed using nonlinear regression, one phase exponential decay (Prism V 3.0).

2. Confocal Microscopy Assay of Amiloride Congener Uptake

Virtually all amiloride-like molecules fluoresce in the ultraviolet range. This property of these molecules may be used to directly measure cellular update using x-z confocal microscopy. Equimolar concentrations of experimental compounds and positive controls including amiloride and compounds that demonstrate rapid uptake into the cellular compartment (benzamil and phenamil) are placed on the apical surface of airway cultures on the stage of the confocal microscope. Serial x-z images are obtained with time and the magnitude of fluorescence accumulating in the cellular compartment is quantitated and plotted as a change in fluorescence versus time.

3. In Vitro Assays of Compound Metabolism

Airway epithelial cells have the capacity to metabolize drugs during the process of transepithelial absorption. Further, although less likely, it is possible that drugs can be metabolized on airway epithelial surfaces by specific ectoenzyme activities. Perhaps more likely as an ecto-surface event, compounds may be metabolized by the infected secretions that occupy the airway lumens of patients with lung disease, e.g. cystic fibrosis. Thus, a series of assays is performed to characterize the compound metabolism that results from the interaction of test compounds with human airway epithelia and/or human airway epithelial lumenal products.

In the first series of assays, the interaction of test compounds in KBR as an "ASL" stimulant are applied to the apical surface of human airway epithelial cells grown in the T-Col insert system. For most compounds, metabolism (generation of new species) is tested for using high performance liquid chromatography (HPLC) to resolve chemical species and the endogenous fluorescence properties of these compounds to estimate the relative quantities of test compound and novel metabolites. For a typical assay, a test solution (25 μl KBR, containing 10 μM test compound) is placed on the epithelial lumenal surface. Sequential 5 to 10 μl samples are obtained from the lumenal and serosal compartments for HPLC analysis of (1) the mass of test compound permeating from the lumenal to serosal bath and (2) the potential formation of metabolites from the parent compound. In instances where the fluorescence properties of the test molecule are not adequate for such characterizations, radiolabeled compounds are used for these assays. From the HPLC data, the rate of disappearance and/or formation of novel metabolite compounds on the lumenal surface and the appearance of test compound and/or novel metabolite in the basolateral solution is quantitated. The data relating the chromatographic mobility of potential novel metabolites with reference to the parent compound are also quantitated.

To analyze the potential metabolism of test compounds by CF sputum, a "representative" mixture of expectorated CF sputum obtained from 10 CF patients (under IRB approval) has been collected. The sputum has been be solubilized in a 1:5 mixture of KBR solution with vigorous vortexing, following which the mixture was split into a "neat" sputum aliquot and an aliquot subjected to ultracentrifugation so that a "supernatant" aliquot was obtained (neat=cellular; supernatant=liquid phase). Typical studies of compound metabolism by CF sputum involve the addition of known masses of test compound to "neat" CF sputum and aliquots of CF sputum "supernatant" incubated at 37° C., followed by sequential sampling of aliquots from each sputum type for characterization of compound stability/metabolism by HPLC analysis as described above. As above, analysis of compound disappearance, rates of formation of novel metabolities, and HPLC mobilities of novel metabolites are then performed.

4. Pharmacological Effects and Mechanism of Action of the Drug in Animals

The effect of compounds for enhancing mucociliary clearance (MCC) can be measured using an in vive model described by Sabater et al., Journal of Applied Physiology, 1999, pp. 2191-2196, incorporated herein by reference.

EXAMPLES

Having generally described this invention, a further understanding can be obtained by reference to certain specific examples which are provided herein for purposes of illustration only and are not intended to be limiting unless otherwise specified.

Preparation of Sodium Channel Blockers

Materials and methods. All reagents and solvents were purchased from Aldrich Chemical Corp. and used without further purification. NMR spectra were obtained on either a Bruker WM 360 ($^1$H NMR at 360 MHz and $^{13}$C NMR at 90 MHz) or a Bruker AC 300 ($^1$H NMR at 300 MHz and $^{13}$C NMR at 75 MHz). Flash chromatography was performed on a Flash Elute™ system from Elution Solution (PO Box 5147, Charlottesville, Va. 22905) charged with a 90 g silica gel cartridge (40M FSO-0110-040155, 32-63 µm) at 20 psi ($N_2$). GC-analysis was performed on a Shimadzu GC-17 equipped with a Heliflex Capillary Column (Alltech); Phase: AT-1, Length: 10 meters, ID: 0.53 mm, Film: 0.25 micrometers. GC Parameters: Injector at 320° C., Detector at 320° C., FID gas flow: $H_2$ at 40 ml/min., Air at 400 ml/min. Carrier gas: Split Ratio 16:1, $N_2$ flow at 15 ml/min., $N_2$ velocity at 18 cm/sec. The temperature program is 70° C. for 0-3 min, 70-300° C. from 3-10 min, 300° C. from 10-15 mm.

HPLC analysis was performed on a Gilson 322 Pump, detector UV/Vis-156 at 360 nm, equipped with a Microsorb MV C8 column, 100 A, 25 cm. Mobile phase: A=acetonitrile with 0.1% TFA, B=water with 0.1% TFA. Gradient program: 95:5 B:A for 1 min, then to 20:80 B:A over 7 min, then to 100% A over 1 min, followed by washout with 100% A for 11 min, flow rate: 1 ml/min.

Example 1

4-(4-Carboxymethylphenyl)butylamidino-3,5-diamino-6-chloropyrazinecarboxamide hydrochloride (9)

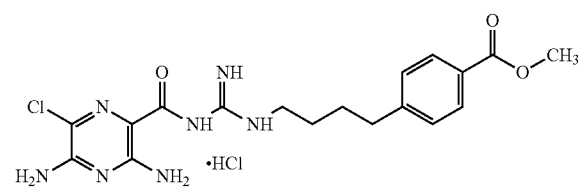

9

Methanesulfonic acid 4-(4-carboxymethylphenyl)butyl ester (6)

Compound 6 was prepared according to the published procedure[1]. $^1$H NMR (300 MHz, CDCl$_3$) δ 1.75 (m, 4H), 2.78 (m, 2H), 3.12 (s, 3H), 3.88 (s, 3H), 4.22 (m, 2H), 7.28 (d, 2H), 7.98 (d, 2H)

4-(4-Carboxymethylphenyl)butylazide (7). Typical procedure C

Compound 6 (6 g, 0.02 mol) was dissolved in 80 ml of dry DMF then sodium azide (1.8 g, 0.027 mol) was added. The suspension was stirred at 80° C. (oil bath) for 3 h. The solvent was then removed at reduced pressure and the residual oil was treated with CH$_2$Cl$_2$ (100 mL). The resulting solution was washed with water (2×100 mL), brine and dried over magnesium sulfate. The solvent was removed under reduced pressure then the residue was redissolved in a 1:1 mixture of ethyl acetate/hexanes (200 mL) and passed through a pad of silica gel. The solvent was removed under reduced pressure to give 4.1 g (85%) of 7 as clear oil. $^1$H NMR (300 MHz, CDCl$_3$) δ 1.68 (m, 4H), 2.22 (t, 2H), 3.29 (t, 3H), 3.92 (s, 3H), 7.28 (d, 2H), 7.98 (d, 2H).

4-(4-Carboxymethylphenyl)butylamine (8)

Azide 7 (1.7 g, 7.2 mmol) and triphenylphosphine (1.9 g, 7.2 mmol) were dissolved in a 10% solution of water in THF (66 mL) and stirred overnight at 25° C. Then more triphenylphosphine (0.8 g, 3 mmol) was added and the heating was continued at 60° C. (oil bath) for 6 h. The solvent was removed under reduced pressure and the residue was treated with 2M HCl (100 mL) and extracted with ethyl acetate (2×50 mL). The water fraction was collected and ammonium hydroxide was added until the pH reached approximately 13. The mixture was extracted with ethyl acetate (2×100 mL) then the organic fraction was washed with brine, water and dried with sodium sulfate. Ethyl acetate was removed under reduced pressure to give 0.8 g (53%) of amine 8.

4-(4-Carboxymethylphenyl)butylamidino-3,5-diamino-6-chloropyrazinecarboxamide hydrochloride (9). Typical procedure D 1-(3,5-Diamino-6-chloropyrazinoyl-2-methyl-pseudothiourea hydroiodide (0.2 g, 0.5 mmol) was added to a solution of 8 (0.7 g, 3.4 mmol) in THF (20 mL). The reaction mixture was stirred at reflux for 6 h, then the solvent was evaporated and the resultant oil was treated with 10% HCl (15 mL). The precipitate was isolated and crystallized twice from ethanol to give 9 (53 mg, 25%) as a yellow solid. $^1$H NMR (300 MHz, DMSO-d$_6$) δ 1.59 (br s, 4H), 2.71 (m, 2H), 3.83 (s, 3H), 7.40 (d, 2H), 7.48 (br s, 2H), 7.80 (d, 2H), 8.92 (br s, 2H), 9.00 (br s, 1H), 9.48 (br s, 2H), 10.55 (s, 1H). APCI MS m/z=420 [C$_{18}$H$_{22}$ClN$_7$O$_3$+H]$^+$.

Example 2

4-(4-Sulfatephenyl)butylamidino-3,5-diamino-6-chloropyrazinecarboxamide (10)

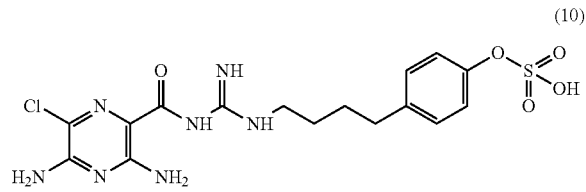 [SMILES: N=C(NCCCCc1ccc(OS(=O)(=O)O)cc1)NC(=O)c1nc(Cl)c(N)nc1N]

(10)

4-(4-Sulfatephenyl)butylamidino-3,5-diamino-6-chloropyrazinecarboxamide (10)

4-(4-Hydroxyphenyl)butylamidino-3,5-diamino-6-chloropyrazinecarboxamide hydrochloride 5 (0.2 g, 0.5 mmol) was dissolved in 5 mL of dry pyridine and pyridine sulfurtrioxide (450 mg, 2.5 mmol) was added. The reaction mixture was stirred overnight at room temperature and the precipitate that formed was isolated by filtration and washed with ethyl acetate (2×25 mL) to give crude 10 (180 mg, 39%, purity 87% by HPLC). An aliquot of the crude 10 (67 mg) was purified by flash chromatography (silica gel, 6:3:0.1 methylene chloride/methanol/concentrated ammonium hydroxide) to give 10 as a yellow solid (9.3 mg, 4% based on starting 5). $^1$H NMR (300 MHz, DMSO-$d_6$) δ 1.59 (br s, 4H), 2.58 (m, 2H), 3.28 (m, 2H), 7.08 (s, 41H), 7.1-7.9 (m, 6H). ESI MS m/z=456 $[C_{16}H_{20}ClN_7O_5S-H]^-$.

Example 3

4-[4(2,3-Dihydroxypropyloxyl)phenyl]butylamidino-3,5-diamino-6-chloropyrazinecarboxamide hydrochloride (33)

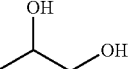

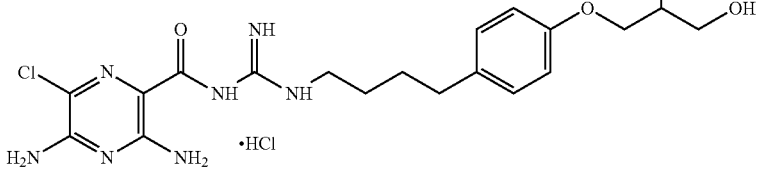

N-Cbz-4-(4-hydroxyphenyl)butylamine (29)

To vigorously stirred suspension of 4 (10.5 g, 0.043 mol) in THF (approx. 150 mL) was added sodium hydrogencarbonate (11 g, 0.13 mol) and then water until a clear solution was obtained (approx. 50 mL). The reaction mixture was cooled to 0° C. then benzyl chloroformate (10 mL, 0.07 mol) was added and the reaction was stirred overnight. The solvent was removed at reduced pressure then ethyl acetate (approx. 100 mL) was added to the residue. The organics were washed with HCl (2 M solution, 2×30 mL), water (2×50 mL), and dried over sodium sulfate. The solvent was removed and the residue was purified by column chromatography (silica gel, 1:1 ethyl acetate/hexanes) to provide 29 (10 g, 85%) as a white solid. $^1$H NMR (300 MHz, CDCl$_3$) δ 1.55 (br s, 4H), 2.53 (m, 2H), 3.19 (m, 2H), 5.05 (s, 2H), 5.83 (s, 1H), 6.73 (d, 2H), 7.00 (d, 2H), 7.38 (m, 5H).

N-Cbz-4-(4-allyloxyphenyl)butylamine (30)

Potassium tert-butoxide (1.7 g, 15.2 mmol) and 18-crown-6 (0.1 g, 0.3 mmol) were added to a solution of 29 (4.3 g, 14.3 mmol) in dry MeCN (80 mL) and the mixture was stirred for 20 min at room temperature. After this time, allyl bromide (1.2 mL, 14.3 mmol) in MeCN (10 mL) was added. The reaction mixture was stirred overnight at room temperature, then the precipitate was filtered off and washed with ethyl acetate. The organic fractions were combined, the solvent was removed at reduced pressure and the residue was purified twice by flash chromatography (silica gel, 1:1 ethyl acetate/hexanes) to provide compound 30 (3.4 g, 71%) as a white solid. $^1$H NMR (300 MHz, CDCl$_3$) δ 1.55 (m, 4H), 2.54 (t, 2H), 3.20 (m, 2H), 4.50 (d, 2H), 5.08 (s, 2H), 5.28 (d, 1H), 5.40 (d, 1H), 6.06 (m, 1H), 6.82 (d, 2H), 7.05 (d, 2H), 7.33 (s, 5H)

N-Cbz-4-[(2,3-dihydroxypropyloxy)phenyl]butylamine (31)

A solution of osmium tetroxide (50 mg, 0.2 mmol) in tert-butanol (8 mL) was added to a solution of 4-methylmorpholine N-oxide monohydrate (1.2 g, 9.1 mmol) in 100 mL (1:1) acetone/water solution and the mixture was stirred for 10 min at room temperature. After this time, 30 (3.1 g, 9.0 mmol) was added in 50 mL (1:1) acetone/water solution. The reaction mixture was stirred at room temperature overnight, then NaHSO$_3$ (0.5 g) was added and the stirring was continued for 15 min. The acetone was evaporated and the pH was adjusted to 5.5 by the addition of 2N HCl then the mixture was extracted with ethyl acetate. The organic fraction was isolated, dried with sodium sulfate, and filtered through silica gel. Compound 31 (2.1 g, 62%) was isolated as a white solid after removing the solvent and drying under vacuum. $^1$H NMR (300 MHz, DMSO-$d_6$) δ 1.48 (m, 2H), 1.50 (m, 2H), 2.46 (m, 2H), 3.00 (m, 2H), 3.43 (m, 2H), 3.80 (m, 2H), 3.93 (t, 1H), 4.66 (d, 1H), 4.99 (s, 2H), 6.82 (d, 2H), 7.07 (d, 2H), 7.26 (s, 1H), 7.33 (s, 5H).

4-[(2,3-Dihydroxypropyloxy)phenyl]butylamine (32)

Cbz-protected amine 31 (2.1 g, 5.6 mmol) was dissolved in methanol (50 mL) and Pd/C (0.46 g, 5% wet) was added in methanol (20 mL). The reaction mixture was stirred for 3 h at 1 atmosphere of hydrogen, then the solution was filtered through a pad of silica gel. The solvent was then evaporated to give free amine 32 (0.9 g, 66%). $^1$H NMR (300 MHz, DMSO-$d_6$) δ 1.37 (m, 2H), 1.50 (m, 2H), 2.92 (m, 1H), 3.22-4.05 (br s, 4H), 3.43 (m, 2H), 3.93 (m, 1H), 6.82 (d, 2H), 7.07 (d, 2H).

4-[4-(2,3-Dihydroxypropyloxyl)phenyl]butylamidino-3,5-diamino-6-chloropyrazinecarboxamide hydrochloride (33). (General Procedure Z)

1-(3,5-Diamino-6-chloropyrazinoyl-2-methyl-pseudothiourea hydroiodide (1.5 g, 3.8 mmol) was added to a solution of 32 (0.9 g, 3.7 mmol) in a mixture of THF (50 mL) and diisopropylethylamine (2 mL). The reaction mixture was stirred at reflux (66° C.) for 4 h. After this time, the reaction mixture was cooled to room temperature and the formed precipitate was isolated as a yellow solid. The obtained solid was washed with 5% HCl, water, and dried under vacuum to give 33 (0.88 g) as a yellow solid. The mother liquor was evaporated and the residue was purified by flash chromatography (silica gel, 5:1:05 chloroform/methanol/concentrated ammonium hydroxide). The isolated free amino compound was treated with 5% HCl to give an additional portion of 33 (0.12 g). The total yield of 33 was 53%. $^1$H NMR (300 MHz, DMSO-$d_6$) δ 1.56 (m, 4H), 2.56 (br s, 2H), 3.31 (m, 2H), 3.42 (m, 2H), 3.82 (m, 2H), 3.93 (m, 2H), 4.32 (br s, 4H), 6.84 (d, 2H), 7.10 (d, 2H), 7.45 (br s, 2H), 8.81 (br s, 1H), 8.94 (br s, 1H), 9.25 (br s, 1H), 10.52 (s, 1H). APCI MS m/z=452 $[C_{19}H_{26}ClN_7O_4+H]^+$.

Example 4

Substituted 3,5-diamino-6-chloropyrazinecarboxamide amidines (cont) Alternate preparation of amine 32

4-(4-Methoxyphenyl)butyramide (117)

4-(4-Methoxyphenyl) butyric acid (1) (450 g, 2.32 mole) was combined with dry THF (4 L) and 4-methylmorpholine (268 mL, 2.43 mole) in a 12 L three neck flask with mechanical stirring, an ice-methanol cooling bath and nitrogen atmosphere. Small pieces of dry ice were used to bring the bath temperature below −20° C. Isobutyl chloroformate was added at a rate so as not to exceed an internal temperature of −10° C. After stirring for 30 min. at −10 to −20° C., a 4.7 M solution of ammonia in methanol (990 mL, 4.64 mole) was added in one portion. During the addition, the reaction temperature rose to 0° C. The reaction was allowed to stir for 30 min. and then allowed to stand overnight. The product mixture was transferred to a 22 L separatory funnel with ethyl acetate (6 L), and 10% sodium chloride solution (1.5 L). The layers were separated and the organic solution was washed with 10% sodium chloride solution (4×1 L) and then brine (3×500 mL). The organic layer was dried over sodium sulfate, filtered, evaporated and placed under high vacuum overnight. This afforded 432 g (97%) of the pure amide (117) as an off white solid.

$^1$H NMR (300 MHz, CD$_3$OD) δ 1.81-1.93 (m, 2H), 2.20 (t, J=7.7 Hz, 2H), 2.57 (t, J=7.7 Hz, 2H), 3.74 (s, 3H), 6.82 (d, J=8.7 Hz), 7.09 (d, J=8.7 Hz, 1H). CI MS m/z=194 [C$_{11}$H$_{15}$NO$_2$+H]$^+$.

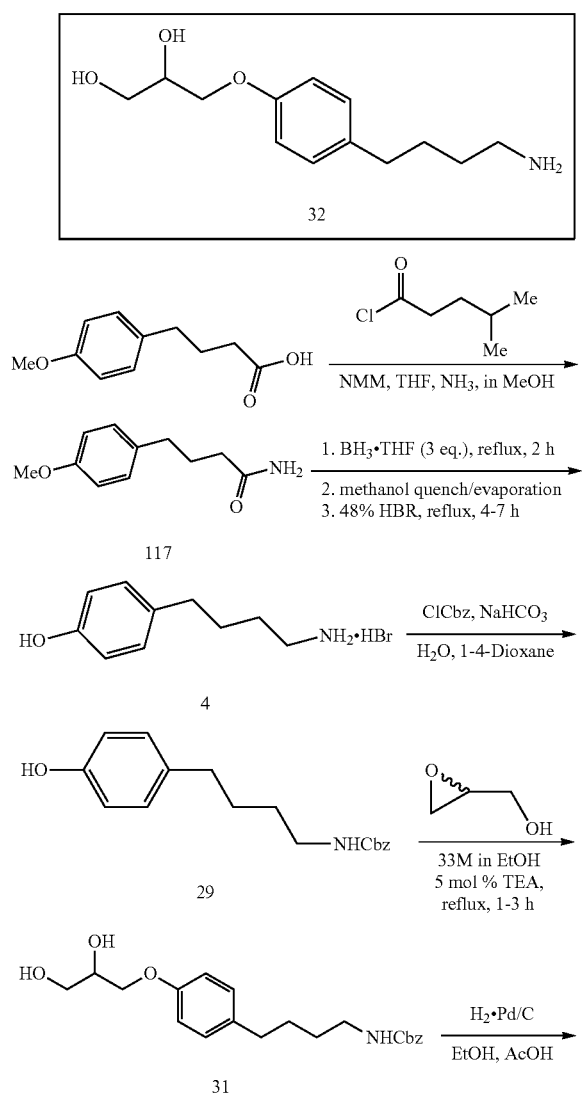

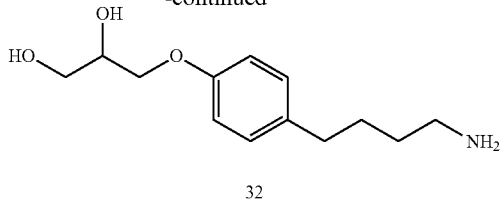

4-(4-Hydroxyphenyl)butylamine hydrobromide (4)

4-(4-Methoxyphenyl)butyramide (117) (200 g, 1.0 mole) and THF (300 mL) were combined in a 12 L three neck flask which was equipped with a heating mantle, an internal thermometer and a reflux condenser. The suspension was slowly mechanically stirred while a 1 M borane-THF complex (1 L, 1 mole) was dripped in via a pressure equalizing addition funnel over 20 min. Another 2.2 L (2.2 mole) of 1 M borane-THF complex was dripped in over 20 min. The reaction temperature rose to 45° C. during the addition. The reaction was stirred and heated to reflux over 1 h, at reflux for 2 h and then allowed to cool for 2 h. Methanol (500 mL) was slowly and cautiously dripped into the reaction. Copious H$_2$ evolution was observed. The reaction was heated at reflux for 2 h and allowed to cool overnight. The reaction was evaporated and then co-evaporated with toluene (500 mL) to a thick oil. 48% HBr (3 L) was slowly and cautiously added to the reaction. Bubbling and foaming was observed during this addition which was exothermic. After the addition, the reaction became stirrable, and was stirred at reflux for 7 h. The reaction was allowed to cool with stirring overnight. The reaction was stirred with ice bath cooling and then suction filtered to collect an off white solid. The solid was co-evaporated with toluene/methanol (1:1) and then dried under vacuum at 60° C. overnight. This afforded 197 g (77%) of (4) as an off white crystalline solid.

$^1$H NMR (300 MHz, CD$_3$OD) δ 1.66 (m, 4H), 2.57 (m, 2H), 2.92 (m, 2H), 6.70 (d, J=8.5 Hz, 2H), 7.01 (d, J=8.5, Hz, 2H). CI MS m/z=166 [C$_{10}$H$_{15}$NO+H]$^+$.

N-Cbz-4-(4-hydroxyphenyl)butylamine (29)

4-(4-Hydroxyphenyl)butylamine hydrobromide (4) (197 g, 0.80 mole), water (1 L), 1,4-dioxane (1 L) and sodium bicarbonate (336 g, 4 mole) were combined and stirred while cooled in an ice-methanol cooling bath. Benzyl chloroformate (141 mL, 0.96 mole) was dripped in over 5 min. at −2° C. with no appreciable exotherm observed. This was stirred and allowed to warm to room temperature as the cooling bath thawed overnight. An additional quantity of benzyl chloroformate (8 mL, 0.54 mol) was dripped in and this was allowed to stir for 2 h. The product mixture was then evaporated to approximately 500 mL and transferred to a 2 L separatory funnel with ethyl acetate while decanting away from the solids. The aqueous layer was extracted with ethyl acetate (3×1 L). The extracts were combined, washed with brine, dried over sodium sulfate, filtered and evaporated to afford 265 g of the crude product. A portion of the crude product (130 g) was chromatographed (silica gel, 5:1 hexanes/ethyl acetate) using toluene to load the column. The remaining crude material was crystallized from 1:1 toluene/heptane. This material was suction filtered to collect the solid and washed with 1:1 toluene/heptane.

This material was vacuum desiccated at 45° C. for 2 h. The combined yield of compound (29) was 150 g (62%) of a white crystalline solid. $^1$H NMR (300 MHz, CDCl$_3$) δ 1.43-1.65 (m, 4H), 2.52 (t, J=7.4 Hz, 2H), 3.19 (q, J=6.4 Hz, 2H), 4.78 (br s, 1H), 5.09 (s, 2H), 5.77 (s, 1H), 6.74 (d, J=8.5 Hz, 2H), 6.98 (d, J=8.5 Hz, 2H), 7.34 (s, 5). CI MS m/z=300 [C$_{18}$H$_{21}$NO$_3$+H]$^+$.

N-Cbz-4-[4-(2,3-dihydroxypropyloxy)phenyl]butylamine (31)

N-Cbz-4-(4-hydroxyphenyl)butylamine (31) (30 g, 0.10 mole), glycidol (8.0 mL, 0.12 mole) ethanol (30 mL) and triethylamine (0.7 mL, 0.005 mole) were stirred at reflux under argon for 2 h. The product mixture was evaporated, taken up in hot ethyl acetate and suction filtered through a plug of silica gel, eluting with ethyl acetate. After evaporating to a white solid, this solid was re-crystallized from toluene to afford 21.8 g (58%) of compound (31). $^1$H NMR (300 MHz, CD$_3$OD) δ 1.42-1.65 (m, 4H), 2.54 (t, J=7.5 Hz, 2H), 3.11 (t, J=6.4 Hz, 2H), 3.58-3.71 (m, 2H), 3.88-4.04 (m, 3H), 5.05 (s, 2H), 6.84 (d, J=8.7 Hz, 2H), 7.06 (d, J=8.5 Hz, 2H), 7.32 (s, 511H).

4-[4-(2,3-propanediol-1-oxy)phenyl]butylamine (32)

N-Cbz-4-[4-(2,3-dihydroxypropyloxy)phenyl]butylamine (31) (67 g, 0.179 mole), ethanol (900 mL), acetic acid (50 mL) and 50% wet 10% palladium on carbon (10 g) were stirred at atmospheric pressure under H$_2$. After stirring overnight, the reaction was purged with nitrogen and suction filtered through a pad of celite. This was evaporated and then co-evaporated 3 times with ethanol (500 mL). The residue was chromatographed (silica gel, 100:10:1 methylene chloride/methanol/concentrated ammonium hydroxide) to afford 38 g (89%) of pure compound (32).
$^1$H NMR (300 MHz, CD$_3$OD) δ 1.42-1.55 (m, 2H), 1.55-1.68 (m, 2H), 2.56 (t, J=7.5 Hz, 2H), 2.65 (t, J=7.2 Hz, 2H), 3.58-3.72 (m, 2H), 3.89-4.05 (m, 3H), 6.85 (d, J=8.7 Hz, 2H), 7.08 (d, J=8.7 Hz, 2H).

Example 5

4-[4-(2,3-Diacetoxypropyloxy)phenyl]butylamidino-3,5-diamino-6-chloropyrazinecarboxamide (36)

N-Cbz-4-[(2,3-diacetoxypropyloxy)phenyl]butylamine (34)

Acetic anhydride (0.6 ml, 6 mmol) was added to solution of 31 (0.55 g, 1.5 mmol) in dry pyridine (50 mL) under stirring. The reaction mixture was stirred 3 h at 25° C. and 3 h at 40° C. (oil bath). After this time, the reaction was quenched with 2N HCl (100 mL) and extracted with ethyl acetate. The organic fraction was washed with water and dried over sodium sulfate. The solvent was removed under reduced pressure to provide 34 (0.6 g 86%) as a white powder. $^1$H NMR (300 MHz, CDCl$_3$) δ 1.55 (m, 4H), 1.98 (s, 3H), 2.02 (s, 3H), 2.55 (m, 2H), 4.08 (m, 2H), 4.30 (m, 2H), 4.45 (m, 1H), 4.80 (br s, 1H), 5.08 (s, 2H), 5.38 (m, tH), 6.82 (d, 2H), 7.08 (d, 2H), 7.35 (s, 5H).

4-[(2,3-diacetoxypropyloxy)phenyl]butylamine (35)

Cbz-protected amine 34 (0.6 g, 1.3 mmol) was dissolved in methanol (25 mL) containing 1% acetic acid then Pd/C (022 g, 5% wet.) was added. The reaction mixture was stirred for 3 h under hydrogen (1 atm), then the solution was filtered through a pad of silica gel and the solvent was evaporated to give amine 35 (0.37 g, 86%) as a clear oil.

4-[4-(2,3-Diacetoxypropyloxy)phenyl]butylamidino-3,5-diamino-6-chloropyrazinecarboxamide (36)

1-(3,5-Diamino-6-chloropyrazinoyl-2-methyl-pseudothiourea hydroiodide (0.37 g, 0.95 mmol) was added to a solution of 35 (0.27 g, 0.7 mmol) in a mixture of THF (40 mL) and diisopropylethylamine (1 mL). The reaction mixture was stirred at reflux (66° C.) for 6 h. After this time, the solvent was evaporated and the residue was dissolved in MeOH. Silica gel (25 mL) was added and the solvent was removed under reduced pressure to adsorb the compound onto the silica gel. This silica gel was added to the top of a silica gel column and flash chromatography (silica gel, 10:1:0.1 chloroform/methanol/concentrated ammonium hydroxide) was performed to obtain crude 36 (128 mg). A second chromatography gave pure 36 (14 mg, 3.7%) as a yellow powder. $^1$H NMR (300 MHz, DMSO-d$_6$) δ 1.56 (m, 4H), 2.05 (s, 6H), 2.58 (m, 2H), 3.14 (m, 2H), 4.10 (m, 2H), 4.28 (m, 2H), 5.28 (br s, 1H), 6.58 (br s, 2H), 6.82 (m, 2H), 7.10 (m, 2H). APCI MS m/z=536[C$_{23}$H$_{30}$ClN$_7$O$_6$+H]$^+$.

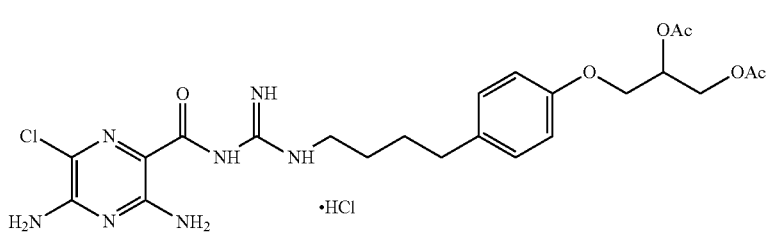

36

Example 6

4-[4-(2,2 Dimethyl-[1,3]dioxolan-4 yl)methyloxyphenyl]butylamidino-3,5-diamino-6-chloropyrazinecarboxamide (37)

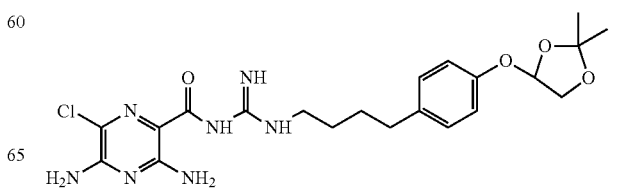

37

4-[4-(2,2 Dimethyl-[1,3]dioxolan-4 yl)methyloxyphenyl]butylamidino-3,5-diamino-6-chloropyrazinecarboxamide (37)

Compound 33 (150 mg, 0.3 mmol) was suspended in dry acetone (50 mL) then methanol was added until a clear solution was formed (approx. 15 mL). p-Toluenesulfonic acid monohydrate (25 mg) was added along with molecular sieves (5 A) and the reaction mixture was stirred for 48 h at room temperature. After this time, the reaction mixture was filtered, silica gel (20 mL) was added and the solvent was removed under reduced pressure. This silica gel with the reaction mixture adsorbed was added to the top of a silica gel flash chromatography column. Compound 37 (120 mg, 81%) was isolated by flash chromatography (silica gel, 10:1:0.1 chloroform/methanol/concentrated ammonium hydroxide) as a yellow solid. $^1$H NMR (300 MHz, DMSO-$d_6$) δ 1.30 (s, 3H), 1.34 (s, 3H), 1.52 (br s, 4H), 2.56 (br s, 2H), 3.13 (br s, 2H), 3.71 (m, 1H), 3.92 (m, 2H), 4.08 (m, 1H), 4.45 (m, 1H), 6.64 (br s, 2H), 6.82 (m, 2H), 7.12 (m, 2H). APCI MS m/z=492 $[C_{22}H_{30}ClN_7O_4+H]^+$.

Example 7

4-[4-(Methyl-2,3,4-tri-O-acetyl-glucopyranonuronate-1-O-yl)phenyl]butylamidino-3,5-diamino-6-chloropyrazinecarboxamide (40)

2,3,4-Tri-O-acetyl-1-O-[4-(4-benzyloxycarbonylaminobutyl)phenyl]glucopyranuronic acid methyl ester (38)

2,3,4-Tri-O-acetyl-α-D-glucuronic acid methyl ester trichloroimidate (1.6 g, 3.3 mmol) was added under argon to protected aminophenol 29 in dry methylene chloride (40 mL) then the solution was cooled to −25° C. After stirring for 10 min, BF$_3$.OEt$_2$ (0.045 mL, 0.33 mmol) was added in methylene chloride (5 mL). The reaction mixture was stirred 1.5 h at −25° C., then allowed to warm up to −10° C. and stirring was continued 1 h at that temperature. After this time, the temperature was increased to 25° C. and the reaction mixture was stirred for 1 h then quenched with saturated ammonium chloride (25 mL). The mixture was extracted with methylene chloride then the organic fraction was washed with water and dried over sodium sulfate. The solvent was evaporated and the residue was purified by flash chromatography (silica gel, 1:2 ethyl acetate/hexanes) to provide 38 (1.5 g, 72%) as a white solid. $^1$H NMR (300 MHz, DMSO-$d_6$) δ 1.41 (m, 2H), 1.51 (m, 2H), 1.99-2.02 (m, 9H), 2.54 (m, 21H), 3.00 (m,2H), 3.63 (s, 3H), 4.69 (m, 1H), 4.99 (s, 2H), 5.04-5.10 (m, 2H), 5.46 (m, 1H), 5.60 (m, 1H), 6.88 (d, 2H), 7.12 (d, 2H), 7.27 (m, 1H), 7.33 (s, 5H). APCI MS m/z=616 $[C_{31}H_{37}NO_{12}+H]^+$.

2,3,4-Tri-O-acetyl-1-O-[4-(4-aminobutyl)phenyl]glucopyranuronic acid methyl ester (39)

Glucuronide 38 (1.5 g, 2.4 mmol) was dissolved in dry methanol (100 mL) and Pd/C (0.62 g, 5%) was added. The reaction mixture was stirred under hydrogen (1 atm) for 2.5 h at room temperature. After this time, the solution was passed through a pad of silica gel and the solvent was evaporated under reduced pressure to give amine 39 (0.94 g, 84%). $^1$H NMR (300 MHz, CDCl$_3$) δ 1.46 (m, 2H), 1.60 (m, 2H), 2.08 (m, 9H), 2.58 (m, 2H), 2.72 (m, 2H), 3.63 (s, 3H), 4.14 (m, 1H), 5.10 (m, 1H), 5.34 (m, 3H), 6.90 (d, 2H), 7.12 (d, 2H).

4-[4-(Methyl 2,3,4-tri-O-acetyl-glucopyranonuronate-1-O-yl)phenyl]butylamidino-3,5-diamino-6-chloropyrazinecarboxamide (40)

1-(3,5-Diamino-6-chloropyrazinoyl-2-methyl-pseudothiourea hydroiodide (0.30 g, 0.8 mmol) was added to a

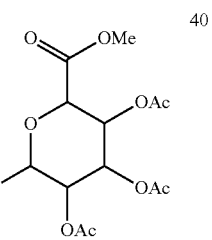

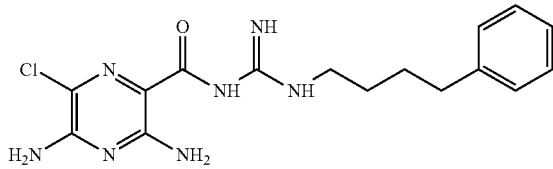

solution of 39 (0.4 g, 0.8 mmol) in a mixture of THF (40 mL) and diisopropylethylamine (3 mL). The reaction mixture was stirred at reflux (66° C.) for 2 h. After this time, the solvent was evaporated and the residue was suspended in THF. Silica gel (15 mL) was added and the solvent was removed under reduced pressure. This silica gel was transferred onto the top of a silica gel chromatography column. The target compound 40 (0.32 g, 48%) was purified by flash chromatography (silica gel, 12:1:0.1 chloroform/ethanol/concentrated ammonium hydroxide) and isolated as a yellow powder. $^1$H NMR (300 MHz, CDCl$_3$) δ 1.61 (br s, 4H), 2.05 (s, 9H), 2.55 (m, 2H), 3.49 (br s, 2H), 3.71 (m, 3H), 4.22 (m, 1H), 5.12 (m, 1H), 5.34 (m, 3H), 6.88 (m, 2H), 7.04 (d, 2H). APCI MS m/z=694 $[C_{29}H_{36}ClN_7O_{11}+H]^+$.

Example 8

4-[4-(5-Carboxy-glucopyranonuronate-1-O-yl)-phenyl]butylamidino-3,5-diamino-6-chloropyrazinecarboxamide (41)

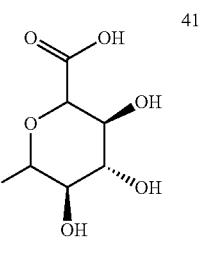

4-[4-(5-Carboxy-2,3,4-tri-O-acetyl-glucopyranonuronate-1-O-yl)phenyl]butylamidino-3,5-diamino-6-chloropyrazinecarboxamide (41)

Compound 40 (0.31 g, 0.44 mmol) was added to mixture of THF/water (1:1, 40 mL) and the resulting cloudy solution was cooled to −10° C. A solution of NaOH in water (4 mL of 1.24 N solution) was added and stirring was continued at 10° C. for 1.5 h. After this time, the reaction mixture was allowed to warm up to room temperature and the THF was removed under reduced pressure. The pH of the remaining solution was adjusted to 6 by drop wise addition of 1N HCl. The formed precipitate was collected by centrifugation and washed with cold water (3×20 mL). Compound 41 (0.18 g, 75%) was isolated as a yellow powder after drying under vacuum for 48 h. $^1$H NMR (300 MHz, DMSO-$d_6$) δ 1.56 (br s, 4H), 2.56 (m, 2H), 3.19 (m, 2H), 3.15-3.40 (br s., 1H), 3.25 (m, 2H), 3.57 (m, 1H), 4.87 (m, 1H), 5.10-5.40 (br d, 1H), 6.89 (m, 2H), 7.06 (m, 2H). APCI MS m/z=554 $[C_{29}H_{36}ClN_7O_{11}+H]^+$.

Example 9

4-[4-(5-Carboxy-glucopyranonuronate-1-O-yl) phenyl]butylamidino-3,5-diamino-6-chloropyrazinecarboxamide trifluoroacetate (42)

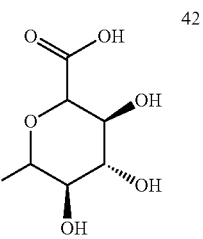

4-Methylphenylsulfonic acid 4-(4-methoxyphenyl)butyl ester (1)

Pyridine (15 mL) was added drop wise to a cooled (0° C.) solution of 4-(4-methoxyphenyl)butanol (10.0 g, 0.055 mol) and p-toluenesulfonyl chloride (13.6 g, 0.072 mol) in dry chloroform (100 mL) under stirring. The reaction mixture was stirred overnight at room temperature. After this time, the reaction was quenched with 10% HCl (300 mL) and extracted with chloroform. The organic fraction was washed with saturated NaHCO$_3$, water and dried over magnesium sulfate. The solvent was removed under reduced pressure and the residue purified by flash chromatography (eluent: hexane/ethyl acetate 15:1) to provide 12.9 g (66%) of 1 as clear oil. $^1$H NMR (360 MHz, CDCl$_3$) δ 1.61 (m, 4H), 2.44 (s, 3H), 2.52 (m, 2H), 3.78 (s, 3H), 4.05 (m, 2H), 6.77 (d, 2H), 7.05 (d, 2H), 7.34 (d, 2H), 7.78 (d, 2H).

4-(4-Methoxyphenyl)butylazide (2)

Sodium azide (3.07 g, 0.047 mol) was added to a solution of 1 (12.9 g, 0.04 mol) in anhydrous DMF (70 mL) and the reaction mixture was stirred 12 h at 80° C. (oil bath). Then solvent was removed at reduced pressure and the residual oil was treated with a mixture of CH$_2$Cl$_2$/ether 3:1 (100 mL). The resulting solution was washed with water (2×100 mL), brine and dried over magnesium sulfate. The solvent was removed under reduced pressure and 7.6 g (95%) of 2 was obtained. The purity of 2 (99%) was determined by GC and TLC (eluent: hexane/ethyl acetate 1:1), R$_f$=0.84.

4-(4-Methoxyphenyl)butylamine (3). Typical procedure A

Lithium aluminum hydride (LAH) (55 mL of a 1.0 M solution in THF, 0.055 mol) was added drop wise to a solution of 2 (7.6 g, 0.037 mol) in dry THF (70 mL) at 0° C. The mixture was stirred overnight at room temperature in an argon atmosphere then the mixture was treated with water (1.5 mL), then 15% NaOH (1.5 mL), then with more water (3 mL) and filtered. The solid precipitate was washed with THF. The combined organic fractions were dried over magnesium sulfate and the solvent was removed under reduced pressure to give 6.2 g (94%) of 3. The purity of 3 (99%) was determined by GC. $^1$H NMR (360 MHz, DMSO-$d_6$) δ 1.34 (m, 2H), 1.54 (m, 2H), 2.51 (m, 4H), 3.70 (s, 3H), 6.83 (d, 2H), 7.08 (d, 2H). $^{13}$C (90 MHz, DMSO-$d_6$) δ 28.6, 330, 34.1, 41.5, 54.8, 113.1, 129.1, 132.2, 157.3

4-(4-Hydroxyphenyl)butylamine hydrobromide (4). Typical procedure B

Amine 3 (2.32 g, 0.012 mol) was stirred in boiling 48% HBr (50 mL) for 3 h. After the reaction was completed, argon was bubbled through the solution and the solvent was evaporated under reduced pressure. The solid residue was dried above KOH to provide 3.1 g (90%) of 4. APCI MS m/z=166[$C_{10}H_{15}NO+H$]$^+$ 4-(4-Hydroxyphenyl)butylamidino-3,5-diamino-6-chloropyrazinecarboxamide hydrochloride (5)

1-(3,5-Diamino-6-chloropyrazinoyl-2-methyl-pseudothiourea hydroiodide (0.4 g, 1.03 mmol) was added to a suspension of 4-(4-hydroxyphenyl)butylamine hydrobromide (4) (0.8 g, 32 mmol) in a mixture of THF (35 mL) and triethylamine (3 mL). The reaction mixture was stirred in the boiling solvent for 3 h, then the supernatant was separated and the solvent was removed under reduced pressure. The oily residue was washed with water (2×30 mL), ether (3×30 mL) and then 10% HCl (40 mL) was added. The mixture was vigorously stirred for 10 min then the yellow solid was filtered off, dried and recrystallized twice from ethanol to give 5 (0.18 g, 41%) as yellow solid. Purity is 98% by HPLC, retention time is 9.77 min. $^1$H NMR (300 MHz, DMSO-$d_6$) δ 1.56 (br s, 4H), 2.48 (br s, 2H), 3.35 (m, 2H), 6.65 (d, 2H), 6.95 (d, 2H), 7.50 (br s, 2H), 8.75 (br s, 1H), 9.05 (br s, 1H), 9.33 (br s, 2H), 10.55 (s, 1H). $^{13}$C NMR (75 MHz, CD$_3$OD) 28.7, 29.8, 35.4, 42.4, 111.2, 116.1, 122.0, 130.0, 134.0, 155.0, 156.1, 156.8, 157.5, 167.0. APCI MS m/z=378 [$C_{16}H_{20}ClN_7O_2+H$]$^+$.

4-[4-(5-Carboxy-glucopyranonuronate-1-O-yl)phenyl]butylamidino-3,5-diamino-6-chloropyrazinecarboxamide trifluoroacetate (42)

Compound 5 (29 mg, 0.07 mmol) was dissolved in DMF (2 mL). A 100 mM TRIS buffer solution, pH 7.5, containing 10 mM MgCl$_2$, 1.0 mM dithiothreitol, 10 mM saccharolactone, and 2 mM CMP (cytidine-mono-phosphate) was made. 176 mg of UDP-GA (uridine-di-phospho-glucuronic acid) was dissolved in the buffer solution (30 mL) and added to 600 mg of bovine liver microsomes (produced at AMRI Biocatalysis Division) in a 50 mL widemouth jar. The DMF solution of 5 was added to initiate the reaction. The reaction was run at room temperature with periodic shaking by hand and was stopped by the addition of an equal volume of MeCN after 42 h. The reaction solution was divided into two (50 mL) centrifuge tubes and centrifuged to remove the enzyme. The precipitated enzyme was re-suspended in MeCN (40 mL) and centrifuged again. This enzyme wash was repeated 3 times until the LC/MS analysis showed only trace amounts of remaining product. The supernatants were combined and the aqueous MeCN was removed under vacuum at 30° C. The resulting syrup was thinned by the addition of MeCN and further dried under vacuum overnight. After drying, the syrup was purified by RP-HPLC (Luna C18 (2) 250×21.2 mm, 5 μm) with a water/acetonitrile (both containing 0.1% TFA) gradient. The appropriate fractions were combined and dried under vacuum to yield 42 (14.8 mg, 28.2%) with 98.4% purity (by HPLC analysis) as a white solid. APCI MS m/z=554 [$C_{29}H_{36}ClN_7O_{11}+H$]$^+$, m/z=552[$C_{29}H_{36}ClNO_{11}-H$]$^-$.

Example 10

4-[4-(1,4-Dioxapent-1-yl) phenyl]butylamidino-3,5-diamino-6-chloropyrazinecarboxamide hydrochloride (66)

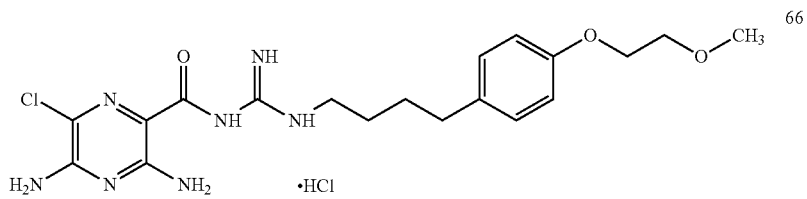 [SMILES: COCCOc1ccc(CCCCNC(=N)NC(=O)c2nc(Cl)c(N)nc2N)cc1 ; Cl]

N-Cbz-4-[4-(1,4-dioxapent-1-yl)phenyl]butylamine (64)

To a vigorously stirred solution of 29 (4 g, 0.013 mol) in anhydrous THF (150 mL) under nitrogen at 0° C. was added sodium hydride (60% dispersion in mineral oil, 0.64 g, 0.016 mol). The mixture was stirred for 15 min then tetrabutylammonium iodide (0.5 g, 0.0013 mol) and 2-bromoethyl methyl ether (2.04 g, 0.015 mol) were added and the mixture was stirred at room temperature overnight. The solvent was removed under reduced pressure and the material was purified by column chromatography (silica gel, 10:1 methylene chloride/ethyl acetate) to provide 64 (3.1 g, 64%). $^1$H NMR (300 MHz, CDCl$_3$) δ 1.60 (m, 4H), 2.59 (m, 2H), 3.23 (m, 2H), 3.45 (s, 3H), 3.77 (m, 2H), 4.10 (m, 2H), 5.13 (s, 2H), 6.88 (d, 2H), 7.08 (d, 2H), 7.47 (s, 5H).

4-(1,4-Dioxapent-1-yl)phenylbutylamine (65)

To a solution of 64 (2.27 g, 6.4 mmol) in ethanol (60 mL) with acetic acid (1 wt. %) was added Pd/C catalyst (300 mg, 10% wet) then the mixture was shaken for 18 h at 30 psi of hydrogen in a Parr hydrogenator. The pressure was released and the catalyst was filtered off through a pad of silica gel. The solvent was removed at reduced pressure to provide 65 (1.3 g, 92%). $^1$H NMR (300 MHz, CDCl$_3$) δ 1.60 (br s, 4H), 2.00 (s, 2H) 2.55 (br s, 2H), 2.85 (br s, 2H), 3.47 (s, 3H), 3.73 (m, 2H), 4.10 (m, 2H), 6.82 (d, 2H), 7.08 (d, 2H).

4-[4-(1,4-Dioxapent-1-yl) phenyl]butylamidino-3,5-diamino-6-chloropyrazinecarboxamide hydrochloride (66)

1-(3,5-Diamino-6-chloropyrazinoyl-2-methyl-pseudothiourea hydroiodide (0.3 g, 0.77 mmol) was added to an anhydrous THF solution (20 mL) of 65 (0.48 g, 2.3 mmol). The reaction mixture was stirred at reflux for 11 h then the solvent was evaporated. The residue was purified on a Biotage system (silica gel, 10:1:0.1 chloroform/methanol/concentrated ammonium hydroxide). The appropriate fractions were collected, the solvent was evaporated and the residue was treated with 3% HCl. The yellow precipitate that formed was separated and washed with ethyl acetate, water and dried to provide 66 (160 mg, 34%) as a yellow solid. $^1$H NMR (300 MHz, DMSO-d$_6$) δ 1.57 (br s, 4H), 2.52 (m, 4H), 3.30 (s, 3H), 3.63 (m, 2H), 4.03 (m, 2H) 6.85 (d, 2H), 7.12 (d, 2H), 7.46 (br s, 2H), 8.00 (br s, 1H), 8.85 (br s, 1H), 8.99 (br s, 1H), 9.32 (br s, 1H), 10.03 (s, 1H). APCI MS m/z 436 [C$_{19}$H$_{26}$ClN$_7$O$_3$+H]$^+$.

Example 11

4-(4-Hydroxymethylphenyl)butylamidino-3,5-diamino-6-chloropyrazinecarboxamide hydrochloride (68)

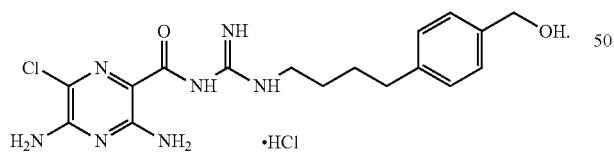

4-(4-Hydroxymethylphenyl)butyl amine (67)

Lithium aluminum hydride (35 mL of a 1.0 M solution in THF, 0.035 mol) was added drop wise to a vigorously stirred solution of 4-(4-carboxymethylphenyl)butylazide 8 (2.4 g, 0.010 mol) in dry THF (120 mL) at 0° C. and stirred overnight at room temperature under a nitrogen atmosphere. To break up the complex water (1.5 mL), 15% NaOH (1:5 mL) and water (4.5 mL) were added drop wise to the cold reaction mixture. The white solid precipitate was filtered off and washed with THF. All organics phases were combined and evaporated. The material was purified by column chromatography (silica gel, 2:1:0.05 chloroform/ethanol/concentrated ammonium hydroxide) to provide 67 (1.17 g, 64%) as a white solid. $^1$H NMR (300 MHz, CDCl$_3$) δ 1.15 (br s, 2H), 1.54 (br s, 2H) 1.70 (br s, 2H), 2.60 (m, 4H), 3.77 (s, 1H), 4.67 (s, 2H), 7.47 (s, 2H), 7.60 (s, 2H).

4-(4-Hydroxymethylphenyl)butylamidino-3,5-diamino-6-chloropyrazinecarboxamide hydrochloride (68)

1-(3,5-Diamino-6-chloropyrazinoyl-2-methyl-pseudothiourea hydroiodide (0.2 g, 0.52 mmol) was added to an anhydrous THF suspension (20 mL) of 67 (0.37 g, 2.06 mmol). The reaction mixture was stirred at reflux for 3 h then the solvent was evaporated. The residue was washed with ethyl acetate (3×15 mL), dried and treated with 3% HCl (15 mL). The yellow solid that formed was filtered, washed with water (2×10 mL) and dried to provide 68 (216 mg, 98%). $^1$H NMR (300 MHz, DMSO-d$_6$) δ 1.57 (br s, 4H), 2.62 (m, 2H), 3.35 (m, 2H), 3.73 (br s, 4H), 4.45 (s, 2H), 7.12 (d, 2H), 7.24 (d, 2H), 8.85 (br s, 1H), 9.98 (br s, 1H), 9.32 (br s, 1H), 10.55 (s, 1H). APCI MS m/z 392 [C$_{17}$H$_{22}$ClN$_7$O$_3$+H]$^+$.

Example 12

4-{4-[(2R)-2,3-Dihydroxypropyloxylphenyl]}butylamidino-3,5-diamino-6-chloropyrazinecarboxamide hydrochloride (71)

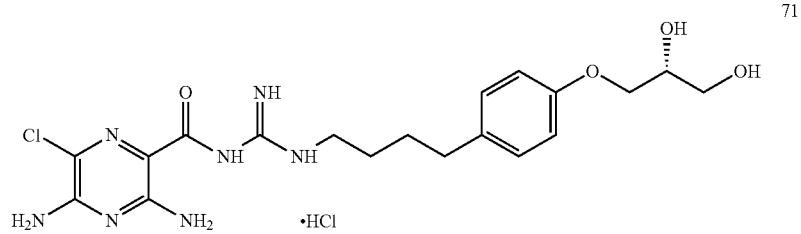 [SMILES: N=C(NCCCCc1ccc(OC[C@H](O)CO)cc1)NC(=O)c1nc(Cl)c(N)nc1N ; Cl]

N-Cbz-4-{[(2R)-2,3-dihydroxypropyloxy]phenyl}butylamine (69)

To cold (0° C.)N-Cbz-4-(4-allyloxyphenyl)butylamine 30 (1.94 g, 5.7 mmol) under a nitrogen atmosphere was added cold (0° C.) AD-Mix-α (12 g) in tert-butanol (100 mL) and water (100 mL). The mixture was allowed to warm to room temperature overnight. The mixture was then quenched with saturated sodium sulfite (200 mL), extracted with ethyl acetate (3×100 mL), dried (Na$_2$SO$_4$) and concentrated to give 69 (2 g, 95%) as a beige solid. $^1$H NMR (300 MHz, DMSO) δ 1.40 (m, 2H), 1.54 (m, 2H) 2.55 (br s, 2H), 3.00 (m, 2H), 3.44 (s, 2H), 3.78 (m, 2H), 3.94 (m, 1H), 4.68 (br s, 1H), 4.93 (s, 1H), 5.00 (s, 2H), 6.83 (d, 2H), 7.08 (d, 2H), 7.30 (br s, 1H), 7.35 (s, 5H).

4-{[(2R)-2,3-dihydroxypropyloxy]phenyl}butylamine (70)

To a vigorously stirred solution of 69 (2 g, 5.4 mmol) in methanol (60 mL) under nitrogen was added Pd/C (10% wet, 0.5 g). The mixture was stirred 2 h at room temperature under an atmosphere of hydrogen then the pressure was released and the mixture was filtered through a pad of silica gel. The solvent was removed and the residue was purified by column chromatography (silica gel, 2:1:0.2 chloroform/ethanol/concentrated ammonium hydroxide) to provide 70 (1.18 g, 92%) as a white solid. $^1$H NMR (300 MHz, DMSO-d$_6$) δ 1.32 (m, 2H), 1.54 (m, 2H), 2.55 (m, 2H), 3.45 (m, 2H), 3.82 (m, 3H), 3.94 (m, 2H), 6.83 (d, 2H), 7.08 (d, 2H).

4-{4-[(2R)-2,3-Dihydroxypropyloxy]phenyl]}butyl-amidino-3,5-diamino-6-chloropyrazinecarboxamide hydrochloride (71)

1-(3,5-Diamino-6-chloropyrazinoyl-2-methyl-pseudothiourea hydroiodide (0.4 g, 1.03 mmol) was added to an anhydrous THF suspension (50 mL) of 70 (0.49 g, 2.00 mmol). The reaction mixture was stirred at reflux for 5 h then the mixture was cooled and the precipitate that formed was collected and washed with 3% HCl (2×5 mL) then dried to provide 71 (290 mg, 58%) as a yellow solid. $^1$H NMR (300 MHz, DMSO-d$_6$) δ 1.57 (s, 4H), 2.55 (d, 2H), 3.35 (d, 2H), 3.90 (m, 5H), 6.82 (d, 2H), 7.10 (d, 2H), 7.47 (br s, 2H), 8.75 (br s, 1H), 8.90 (br s, 1H), 10.5 (s, 1H). APCI MS m/z 452 [C$_{19}$H$_{26}$ClN$_7$O$_4$+H]$^+$.

Example 13

4-{4-[(2S)-2,3-Dihydroxypropyloxyl]phenyl]}butyl-amidino-3,5-diamino-6-chloropyrazinecarboxamide hydrochloride (74)

N-Cbz-4-{[(2S)-2,3-dihydroxypropyloxy]phenyl}butylamine (72)

To cold (0° C.)N-Cbz-4-(4-allyloxyphenyl)butylamine 30 (1.53 g, 4.5 mmol) under a nitrogen atmosphere was added cold (0° C.) AD-Mix-β (9.2 g) in tert-butanol (100 mL) and water (100 mL). The mixture was allowed to warm to room temperature overnight. The mixture was quenched with saturated sodium sulfite (200 mL), extracted with ethyl acetate (3×100 mL), dried (Na$_2$SO$_4$) and concentrated to provide 72 (1.67 g, 99%) as a beige solid. $^1$H NMR (300 MHz, CDCl$_3$) δ 1.54 (m, 4H) 2.55 (br s, 2H), 3.18 (m, 2H), 3.70 (s, 3H), 4.02 (d, 2H), 4.10 (m, 1H), 4.73 (br s, 1H), 5.08 (s, 2H), 6.83 (d, 2H), 7.08 (d, 2H), 7.38 (s, 1H), 7.35 (s, 5H).

4-{[(2S)-2,3-dihydroxypropyloxy]phenyl}butylamine (73)

Compound 73 was prepared in a similar fashion to the synthesis of compound 70 starting from compound 72 (1.67 g, 4.5 mmol). Amine 73 (1.06 g, 99%) was isolated as a white solid. $^1$H NMR (300 MHz, DMSO-d$_6$) δ 1.32 (m, 2H), 1.54 (m, 2H), 2.55 (m, 2H), 3.45 (m, 2H), 3.75 (m, 3H), 3.94 (m, 2H), 6.83 (d, 2H), 7.08 (d, 2H).

4-{4-[(2S)-2,3-Dihydroxypropyloxy]phenyl]}butyl-amidino-3,5-diamino-6-chloropyrazinecarboxamide hydrochloride (74)

Compound 74 was prepared in a similar fashion to the synthesis of compound 71 starting from compound 73 (0.74 g, 3.09 mmol). Compound 74 (0.38 g, 76%) was isolated as a yellow solid. $^1$H NMR (300 MHz, DMSO-d$_6$) δ 1.57 (s, 4H), 2.55 (d, 2H), 3.35 (d, 2H), 3.85 (m, 5H), 6.82 (d, 2H), 7.10 (d, 2H), 7.47 (br s, 2H), 8.75 (br s, 1H), 8.90 (br s, 1H), 10.5 (s, 1H). APCI MS m/z 452 [C$_{19}$H$_{26}$ClN$_7$O$_4$+H]$^+$.

Example 14

4-(4-Aminophenyl)ethylamidino-3,5-diamino-6-chloropyrazinecarboxamide hydrochloride (83)

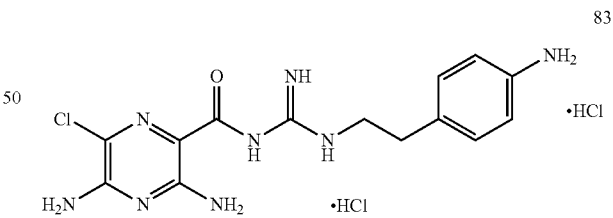

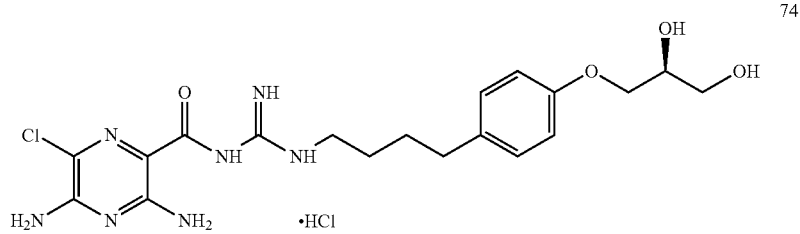 [SMILES: N=C(NCCCCc1ccc(OC[C@@H](O)CO)cc1)NC(=O)c1nc(Cl)c(N)nc1N ; Cl]

4-(4-Aminophenyl)ethylamidino-3,5-diamino-6-chloropyrazinecarboxamide hydrochloride (83)

A mixture of 1-H-pyrazolecarboxamidine hydrochloride (2.8 g, 19 mmol), 4-aminoethylamiline (1.3 mL, 9 mmol) and diisopropylethylamine (1.3 ml) were stirred in dry DMF (5 mL) under argon for 18 h. After this time, ether (30 ml) was added to produce a clear oil. The obtained oil (82) was washed with ether and dried under vacuum (40 mTorr) overnight. After drying 70 mg of oil was taken into dry methanol (3 mL) and 25% NaOH (0.14 mL) was added. The reaction volume was decreased to 1.0 mL and 3,5-diamino-6-chloropyrazine-2 carboxylic acid methyl ester (0.1 g, 0.5 mmol) was added. The mixture was stirred at room temperature overnight. Another portion of 82 (0.1 g) was dissolved in methanol (1 mL), treated with 25% NaOH (0.15 mL) and the resulting solution was added to the reaction mixture. The reaction mixture was stirred 3 h at reflux, then cooled to room temperature and the solvent was removed under reduced pressure. The residue was dissolved in a minimal volume of DMF and separated by preparative HPLC. The obtained fractions were analyzed by LC/MS. The fractions containing product with M+H=349 were collected and the solvent was removed under reduced pressure. The residue was dissolved in 10% HCl and evaporated to dryness to produce 83 (23.5 mg, 11%) as a yellow solid. $^1$H NMR (360 MHz, DMSO-$d_6$) δ 2.91 (m, 2H), 3.59 (m, 2H), 7.31 (d, 2H), 7.42 (m, 4H), 9.02 (br s., 2H), 9.41 (br s., 1H), 10.56 (s, 1H). $^{13}$C NMR (90 MHz, DMSO-$d_6$) 33.1, 42.0, 108.9, 119.6, 120.7, 129.9 (2C), 131.0 (2C), 153.1, 154.1, 155.8, 165.2. API MS m/z=349 $[C_{14}H_{17}ClN_8O+H]^+$.

Preparative HPLC was performed on a Gilson Combichem using a Luna C18(2) column, 5µ, 250×21.2 mm; Flow rate=20 mL/min; Mobile phase consists of MeCN/water containing 0.1% TFA; Gradient: 10% MeCN from the 0-2 min interval, concentration of MeCN increased from 10 to 40% from 2-10 min, 40 to 100% MeCN from 10-19 min, 100% MeCN from 19-23 min, MeCN decreased from 100 to 10% from 23-25 min.

Example 15

4-[4-(1,4,7-Trioxaoct-1-yl)phenyl]-butyl amidino-3,5-diamino-6-chloropyrazinecarboxamide hydrochloride (108)

4-[4-(1,4,7-Trioxaoct-1-yl)phenyl]-N-benzyloxycarbonylbutylamine (106)

4-(4-Hydroxyphenyl)-N-benzyloxycarbonylbutylamine (29) (1.0 g, 3.3 mmol), 1-bromo-2-(2-methoxyethoxy)ethane (0.67 g, 3.7 mmol), and potassium carbonate (0.60 g, 4.3 mmol) were combined in acetone (20 mL), and stirred at reflux overnight. The reaction was allowed to cool, and then filtered and evaporated. The residue was re-subjected in methyl ethyl ketone (10 mL), 1-bromo-2-(2-methoxyethoxy)ethane (0.91 g, 5.0 mmol), potassium carbonate (0.74 g, 5.3 mmol), and sodium iodide (0.5 g, 3.3 mmol) with stirring at reflux for 2.5 h. The reaction was allowed to cool, and was filtered and evaporated. The residue was re-subjected in DMF (10 mL), with 1-bromo-2-(2-methoxyethoxy)ethane (1.8 g, 9.8 mmol), potassium carbonate (1.60 g, 11.6 mmol), and sodium iodide (0.4 g, 2.7 mmol), overnight with stirring at 70° C. The reaction was evaporated to remove the solvent and then was dissolved in ethyl acetate (70 mL). The organic extract was washed with water (3×20 mL), dried over potassium carbonate and filtered. Evaporation afforded 1.1 g of an oil which was purified by column chromatography (silica gel, 2:1 hexanes/ethyl acetate) to afford 800 mg (70%) of pure product 106. $^1$H NMR (300 MHz, CDCl$_3$) δ 1.42-1.68 (m, 4H), 2.55 (t, J=7.5 Hz, 2H), 3.20 (q, J=6.2 Hz, 2H), 3.39 (s, 3H), 3.55-3.60 (m, 2H), 3.69-3.74 (m, 2H), 3.82-3.87 (m, 2H), 4.11 (t, 5.3 Hz, 2H), 4.71 (br s, 1H), 5.09 (s, 2H), 6.82 (d, J=8.5 Hz, 2H), 7.05 (d, J=8.5 Hz, 2H), 7.34 (s, 511H). CI MS m/z=402 $[C_{23}H_{31}NO_5+H]^+$.

4-[4-(1,4,7-Trioxaoct-1-yl)phenyl]butylamine (107)

Compound 106 (800 mg, 2.0 mmol) in ethanol (20 mL), was subjected to 1 atmosphere of H$_2$ in the presence of 10% palladium on carbon (100 mg, cat.) with stirring for 5 h. After standing overnight, the reaction was purged with N$_2$ then suction filtered through celite and washed off the celite with methylene chloride. The solvents were evaporated and chromatographed (silica gel, 200:10:1 methylene chloride/methanol/concentrated ammonium hydroxide) to afford 530 mg (>99%) of amine 107. $^1$H NMR (300 MHz, CDCl$_3$) δ 1.31 (br s, 2H), 1.41-1.52 (m, 2H), 1.55-1.67 (m, 2H), 2.56 (t, J=7.7 Hz, 2H), 2.70 (t, J=7.0 Hz, 2H), 3.39 (s, 3H), 3.58 (m, 2H), 3.72 (m, 2H), 3.84 (t, J=4.9 Hz, 2H), 4.12 (t, J=5.3 Hz, 2H), 6.83 (d, J=8.7 Hz, 2H), 7.07 (d, J=8.7 Hz, 2H). CI MS m/z=268 $[C_{15}H_{25}NO_3+H]^+$.

4-[4-(1,4,7-Trioxaoct-1-yl)phenyl]-butylamidino-3,5-diamino-6-chloropyrazinecarboxamide hydrochloride (108)

Amine 107 (200 mg, 0.75 mmol), 1-(3,5-Diamino-6-chloropyrazinoyl-2-methyl-pseudothiourea hydroiodide (296 mg, 0.76 mmol) and triethylamine (0.52 mL, 3.73 mmol) were combined in THF (5 mL) and stirred at reflux

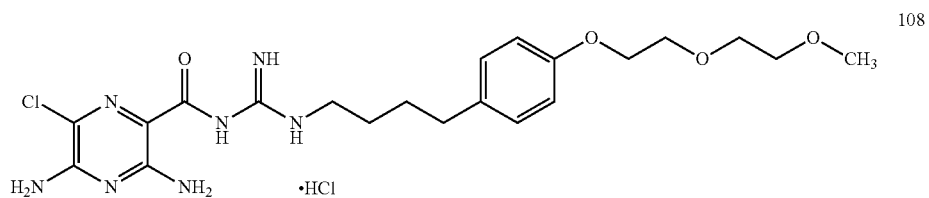 [SMILES: COCCOCCOc1ccc(CCCCNC(=N)NC(=O)c2nc(Cl)c(N)nc2N)cc1 ; Cl]

under N$_2$ for 1.5 h. After stirring at room temperature for two days, the reaction was evaporated. The residue was chromatographed (silica gel, 400:10:1 to 200:10:1 gradient elution, methylene chloride/methanol/concentrated ammonium hydroxide) to afford the free base of the product (290 mg). This material was stirred in methanol (20 mL) at 0° C. then 1M HCl (3 mL) was added. The solution was evaporated with no heating and then co-evaporated with methanol. The residue was dissolved in methanol and then precipitated by the addition of ethyl acetate. This precipitate was centrifuged and the supernatant was decanted. The gel like pellet was evaporated, co-evaporated with water (2 mL) and then placed on high vacuum overnight. This afforded 129 mg (42%) of compound 108 as a yellow solid. $^1$H NMR (300 MHz, DMSO-$d_6$) δ 1.58 (m, 4H), 2.58 (br s, 2H), 3.25 (s, 3H), 3.33 (m, 2H), 3.45 (m, 2H), 3.58 (m, 2H), 3.72 (m, 2H), 3.04 (m, 2H), 4.92 (br s, 4H), 6.85 (d, J=8.5 Hz, 2H), 7.12 (d, J=8.4 Hz, 2H), 8.10 to 7.26 (br m, 3H), 8.94 (br d, 2H), 9.32 (br s, 1H), M.P.=110-125° C. APCI MS m/z=480 $[C_{21}H_{30}ClN_7O_4+H]^+$.

Example 16

4-[4-(1,4,7,10,13-pentoxatetradec-1-yl)phenyl]-butylamidino-3,5-diamino-6-chloropyrazinecarboxamide hydrochloride (112)

evaporated. Chromatography (silica gel, 3:1 methylene chloride/ethyl acetate) afforded 400 mg (81%) of compound 110. $^1$H NMR (300 MHz, CDCl$_3$) δ 1.44-1.67 (m, 4H), 2.55 (t, J=7.7 Hz, 2H), 3.20 (q, J=6.0 Hz, 2H), 3.37 (s, 3H), 3.54 (m, 2H), 3.61-3.75 (m, 10H), 3.84 (t, J=4.9 Hz, 2H), 4.10 (t, 5.5 Hz, 2H), 4.71 (br. s, 1H), 5.09 (s, 2H), 6.82 (d, J=8.5 Hz, 2H), 7.05 (d, J=8.6 Hz, 2H), 7.34 (s, 5H).

4-[4-(1,4,7,10,13-pentoxatetradec-1-yl)phenyl]butylamine (111)

This compound was prepared in a similar fashion to the synthesis of amine 107 from compound 110 (385 mg, 0.78 mmol) to give 266 mg (95%) of compound 111. $^1$H NMR (300 MHz, CDCl$_3$) δ 1.41-1.54 (m, 2H), 1.60 (br. s, 2H), 2.56 (t, J=7.5 Hz, 2H), 2.70 (t, J=7.0 Hz, 2H), 3.37 (s, 3H),

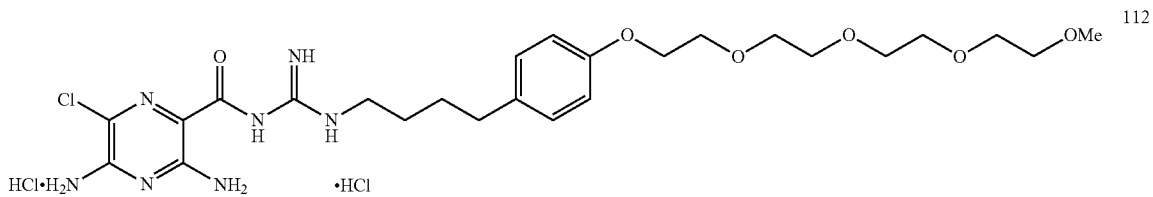

O-Tosyltetraethyleneglycol methyl ether (109)

Tetraethyleneglycol monomethyl ether (2.0 g, 9.6 mmol) was combined with pyridine (0.93 mL, 11.5 mmol) in methylene chloride (20 mL) at 0° C. p-Toluenesulfonyl chloride (2.2 g, 11.5 mmol) dissolved in methylene chloride (10 mL) was added dropwise and the reaction was allowed to warm to room temperature as the ice bath thawed. After stirring nine days, the product mixture was transferred to a separatory funnel with water (70 mL). The layers were separated and the aqueous layer was extracted with methylene chloride (3×20 mL). The extracts were combined and evaporated. The residue (3.3 g) was chromatographed (silica gel, 4:1 to 3:1 gradient elution, methylene chloride/ethyl acetate) to afford 2.5 g (70%) of compound 109 as an oil. $^1$H NMR (300 MHz, DMSO-$d_6$) δ 1.56 (br s, 4H), 2.42 (br s, 2H), 3.34 (br s, 4H), 6.05 (s, 3H), 7.09 (s, 0.5H), 7.26 (s, 0.5H), 7.42 (br s, 2H), 7.70 (br s, 2H), 8.87 (br d, 2H), 9.07 (s, 2H), 9.22 (br s, 1H), 10.51 (s, 11H). CI MS m/z=363 $[C_{16}H_{26}O_7S+H]^+$.

4-[4-(1,4,7,10,13-pentoxatetradec-1-yl)phenyl]-N-benzyloxycarbonylbutylamine (110)

4-(4-Hydroxyphenyl)-N-benzyloxycarbonylbutylamine (29) (0.30 g, 1.0 mmol), 0-tosyltetraethyleneglycol methyl ether (109) (1.45 g, 4.0 mmol), potassium carbonate (0.69 g, 5 mmol) and sodium iodide (0.6 g, 4.0 mmol) were combined in DMF (5 mL) and stirred at 55° C. overnight. Cesium carbonate (0.33 g, 1.0 mmol) was added and the reaction was stirred at 70° C. overnight. The mixture was allowed to cool and was then partitioned between 1:1 toluene/ethyl acetate (70 mL) and water (20 mL). The layers were separated and the organic layer was washed with water (4×10 mL), brine (2×30 mL), dried over sodium sulfate and 3.51-3.58 (m, 2H), 3.60-3.77 (m, 10H), 3.84 (m, 2H), 4.10 (t, 5.5 Hz, 2H), 6.83 (d, J=8.3 Hz, 2H), 7.07 (d, J=8.7 Hz, 2H).

4-[4-(1,4,7,10,13-pentoxatetradec-1-yl)phenyl]butylamidino-3,5-diamino-6-chloropyrazinecarboxamide hydrochloride (112)

This compound was prepared in a similar fashion to the synthesis of compound 108 from compound 111 (250 mg, 0.70 mmol) and 1-(3,5-diamino-6-chloropyrazinoyl-2-methyl-pseudothiourea hydroiodide (200 mg, 0.51 mmol) to give 130 mg (46%) of compound 112. $^1$H NMR (300 MHz, DMSO-$d_6$) δ 1.57 (br s, 4H), 2.55 (br s, 2H), 3.05 to 3.90 (m, 2H), 6.85 (d, J=7.6 Hz, 2H), 7.12 (d, J=7.4 Hz, 2H), 7.44 (br s, 1H), 8.10-7.40 (m, 2H), 8.93 (br d, 2H), 9.32 (s, 1H), 10.55 (s, 1H). APCI MS m/z=568 $[C_{25}H_{38}ClN_7O_6S+H]^+$.

Example 17

4-[4-(2-Hydroxyethyloxy)phenyl)]butylamidino-3,5-diamino-6-chloropyrazinecarboxamide hydrochloride (116)

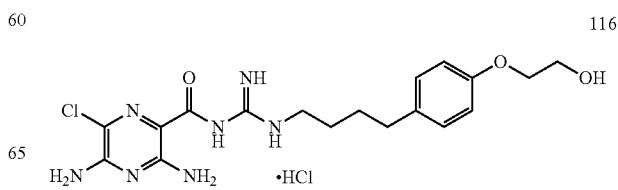

N-{4-[4-(2-hydroxyethyloxy)phenyl]but-3-yn-1-yl}phthalimide (113)

2-(4-Bromophenoxy)ethanol (3 g, 14.5 mmol), palladium (f) chloride (0.2 g, 1.1 mmol) and triphenylphosphine (0.6 g, 2.2 mmol) were dissolved in triethylamine (70 mL) then copper(I) iodide (0.45 g, 2.1 mmol) and N-(but-3-yn)phthalimide (3.2 g, 16 mmol) were added. The reaction mixture was stirred for 72 h at room temperature and 5 h at 50° C. (oil bath), then the solvent was removed under reduced pressure. Ethyl acetate (150 mL) was added to the residue and the mixture was washed with 2N HCl, brine and water. The organic fraction was isolated, dried with sodium sulfate and the solvent was removed under reduced pressure. The product 113 (1.7 g, 43%) was isolated by flash chromatography (silica gel, 10:1:2 methylene chloride/ethyl acetate/hexanes) as a brown oil. $^1$H NMR (300 MHz, CDCl$_3$) δ 2.80 (m, 2H), 3.95 (m, 4H), 4.08 (m, 2H), 6.83 (d, 2H), 7.35 (m, 2H), 7.72 (m, 2H), 7.88 (m, 2H).

N-{4-[4-(2-hydroxyethyloxy)phenyl]butyl}phthalimide (114)

A solution of 113 (1.7 g, 5.1 mmol) in a mixture of methanol/ethyl acetate (80 and 10 mL correspondingly) was placed in a 0.5 L Parr flask and palladium on carbon (1.1 g, 5% wet. Pd/C) was added. The reaction mixture was shaken at 50 psi of hydrogen pressure at room temperature overnight. After this time, the mixture was filtered through a silica gel pad and the solvent was removed at reduced pressure to give crude 114 (1.2 g) as a brown oil. The crude 114 was used in the next step without further purification.

4-[4-(2-hydroxyethyloxy)phenyl]butyl amine (115)

The crude protected amine 114 (1.2 g, 35 mmol) was dissolved in 40 mL of a 2 N solution of methyl amine in dry methanol and the reaction mixture was stirred overnight at room temperature. After this time the solvent was removed under reduced pressure and the residue was purified by flash chromatography (silica gel, 5:1:0.1 chloroform/methanol/concentrated ammonium hydroxide) to give free amine 115 (0.25 g, 35%) as a clear oil. $^1$H NMR (300 MHz, DMSO-d$_6$) δ 1.58 (m, 4H), 2.55 (m, 2H), 2.73 (m, 2H), 3.83 (m, 2H), 3.97 (m, 2H), 6.83 (d, 2H), 7.07 (d, 2H), 7.82 (s, 1H).

4-[4-(2-hydroxyethyloxy)phenyl]]butylamidino-3,5-diamino-6-chloropyrazinecarboxamide hydrochloride (116)

1-(3,5-Diamino-6-chloropyrazinoyl-2-methyl-pseudothiourea hydroiodide (0.32 g, 0.8 mmol) was added to a solution of amine 115 (0.25 g, 1.2 mmol) in a mixture of THF (15 mL), methanol (5 mL) and diisopropylethylamine (1 mL). The reaction mixture was stirred at reflux for 3.5 h and then cooled to room temperature. The formed precipitate was isolated, washed with ethyl acetate (2×5 mL) and treated with 5% HCl (10 mL). The resulting solid was isolated by filtration, washed with water and dried under vacuum to give compound 116 (0.25 g, 73%) as a yellow solid. $^1$H NMR (300 MHz, DMSO-d$_6$) δ 1.56 (m, 4H), 2.57 (m, 2H), 3.32 (m, 2H), 3.70 (m, 2H), 3.93 (m, 2H), 4.90 (t, 1H), 6.84 (d, 2H), 7.12 (d, 2H), 7.45 (s, 2H), 8.70 (br s, 1H), 8.88 (br s, 11H), 9.12 (br s, 1H) 10.45 (s, 1H). APCI MS m/z=422 [C$_{18}$H$_{24}$ClN$_7$O$_3$+H]$^+$.

Example 18

4-[4-(2-Hydroxypropyloxy)phenyl)]butylamidino-3,5-diamino-6-chloropyrazinecarboxamide hydrochloride

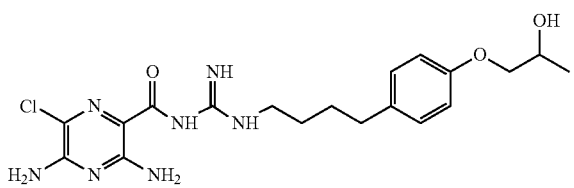 [SMILES: CC(O)COc1ccc(CCCCNC(=N)NC(=O)c2nc(Cl)c(N)nc2N)cc1]

Using general procedure Z, 4-[4-(2-hydroxypropyloxy)phenyl]butyl amine was converted into 4-[4-(2-hydroxypropyloxy)phenyl)]butylamidino-3, 5-diamino-6-chloropyrazinecarboxamide hydrochloride, m.p. 212-214° C., APCI MS, M/Z=436 [C$_{19}$H$_{26}$ClN$_7$O$_3$+H]$^+$.

Example 19

4-[4-(3-Hydroxypropyloxy)phenyl)]butylamidino-3,5-diamino-6-chloropyrazinecarboxamide hydrochloride

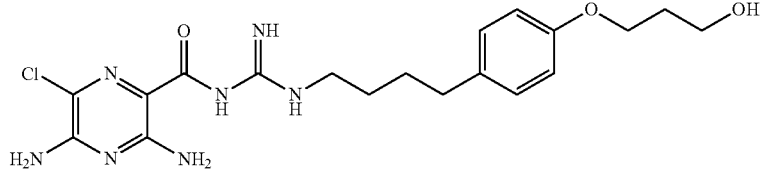 [SMILES: N=C(NCCCCc1ccc(OCCCO)cc1)NC(=O)c1nc(Cl)c(N)nc1N]

Using general procedure Z, 4-[4-(3-hydroxypropyloxy)phenyl]butyl amine was converted into 4-[4-(3-hydroxypropyloxy)phenyl)]butylamidino-3,5-diamino-6-chloropyrazinecarboxamide hydrochloride, m.p. 211-213'C, APCI MS, M/Z=436 [C$_{19}$H$_{26}$ClN$_7$O$_3$+H]$^+$.

Example 20

4-[4-(2-{-Tetrahydropyan-2-yl}oxyethyloxy)phenyl)]butylamidino-3,5-diamino-6-chloropyrazinecarboxamide

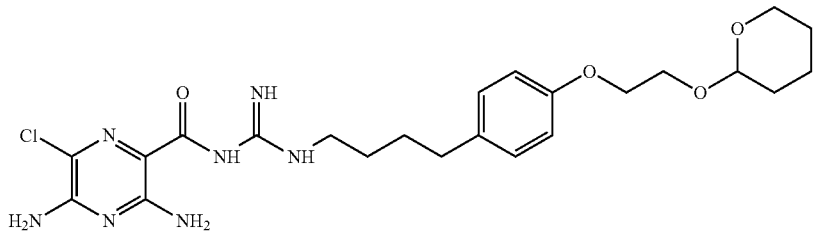 [SMILES: N=C(NCCCCc1ccc(OCCOC2CCCCO2)cc1)NC(=O)c1nc(Cl)c(N)nc1N]

Using general procedure Z, 4-[4-(2-{tetrahydropyan-2-yl}oxyethyloxy)phenyl]butyl amine was converted into 4-[4-(2-{tetrahydropyan-2-yl}oxyethyloxy)phenyl)]butylamidino-3,5-diamino-6-chloropyrazinecarboxamide, m.p. 161° C., APCI Mass Spectrum, M/Z=506 [$C_{23}H_{32}ClN_7O_4$+H].+

Example 21

4-[3-(2-,3-Dihydroxypropyloxyl)phenyl)]butylamidino-3,5-diamino-6-chloropyrazinecarboxamide hydrochloride

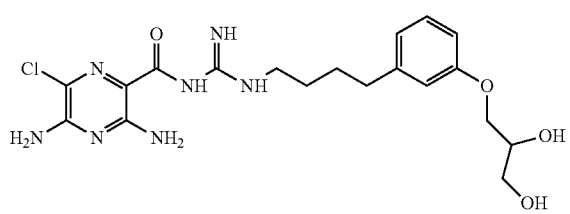 [SMILES: N=C(NCCCCc1cccc(OCC(O)CO)c1)NC(=O)c1nc(Cl)c(N)nc1N]

Using general procedure Z, 4-[3-(2,3-dihydroxypropyloxy)phenyl]butylamine was converted into 4-[3-(2,3-dihydroxypropyloxy)phenyl]butylamidino-3,5-diamino-6-chloropyrazinecarboxamide hydrochloride, m.p. 91-93° C., APCI Mass Spectrum, M/Z=452 [$C_{19}H_{26}ClN_7O_4$+H]+.

Example 22

4-[2-(2-,3-Dihydroxypropyloxy)phenyl)]butylamidino-3,5-diamino-6-chloropyrazinecarboxamide hydrochloride

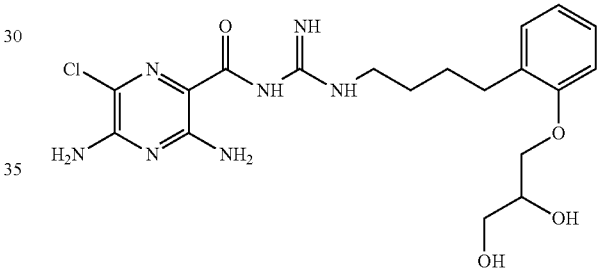

Using general procedure Z, 4-[2-(2,3-dihydroxypropyloxy)phenyl]butylamine was converted into 4-[2-(2,3-dihydroxypropyloxy)phenyl]butylamidino-3,5-diamino-6-chloropyrazinecarboxamide hydrochloride, m.p. 200-205° C., APCI Mass Spectrum, M/Z=452 [$C_{19}H_{26}ClN_7O_4$+H]+.

Example 23

4 [4-(2,3,4-Trihydroxybutyloxy)phenyl)]butylamidino-3,5-diamino-6-chloropyrazinecarboxamide hydrochloride

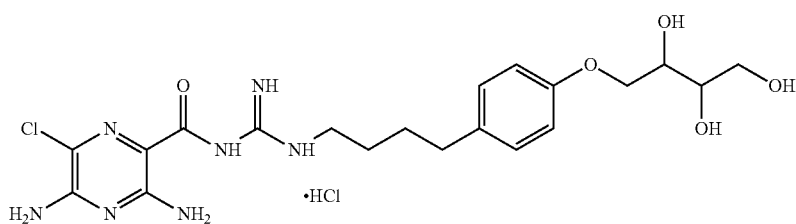 [SMILES: N=C(NCCCCc1ccc(OCC(O)C(O)CO)cc1)NC(=O)c1nc(Cl)c(N)nc1N ; Cl]

Using general procedure Z, 4-[4(2,3,4-trihydroxybutyloxy)phenyl]butylamine was converted into 4-[4-(2,3,4-trihydroxybutyloxy)phenyl]butylamidino-3, 5-diamino-6-chloropyrazinecarboxamide hydrochloride. m.p. 148° C. (dec), APCI Mass Spectrum, M/Z=482 [$C_{20}H_{29}ClN_7O+H$].+

Example 24

4-[4-(4-Amino)phenyl)]butylamidino-3,5-diamino-6-chloropyrazinecarboxamide hydrochloride

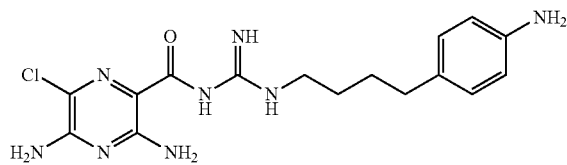 [SMILES: N=C(NCCCCc1ccc(N)cc1)NC(=O)c1nc(Cl)c(N)nc1N]

Using general procedure Z, 4-[(4-amino)phenyl]butylamine was converted into 4-[4-(4-amino)phenyl]butylamidino-3,5-diamino-6-chloropyrazinecarboxamide hydrochloride. m.p. 195-200'(dec), APCI Mass Spectrum, M/Z=377 [$C_{16}H_{21}ClN_8O_4$+H+].+

Example 25

4-[4-(2-aminoethyloxy) phenyl)butylamidino-3,5-diamino-6-chloropyrazinecarboxamide hydrochloride

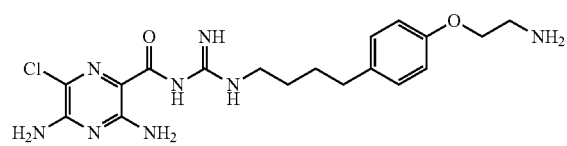 [SMILES: N=C(NCCCCc1ccc(OCCN)cc1)NC(=O)c1nc(Cl)c(N)nc1N]

Using general procedure Z, 4-[4-(2{t-butoxycarbonylamino}ethyloxy)phenyl]butyl amine was converted into 4-[4-(2-{t-butoxycarbonylamino}ethyloxy)phenyl)]butylamidino-3,5-diamino-6-chloropyrazinecarboxamide, m.p. 118° C., APCI MS M/Z=521 [$C_{23}H_{33}ClN_8O_4$+H]+, which was hydrolyzed and acidified with HCL to give 4-[4-(2-aminoethyloxy) phenyl)butylamidino-3,5-diamino-6-chloropyrazinecarboxamide hydrochloride, m. p.>178° C. (dec), M/Z=421 [$C_{18}H_{25}ClN_8O_2$].

Example 26

4-(4-(2-Hydroxyethyl)phenyl)butylamidino-3,5-diamino-6-chloropyrazinecarboxamide hydrochloride

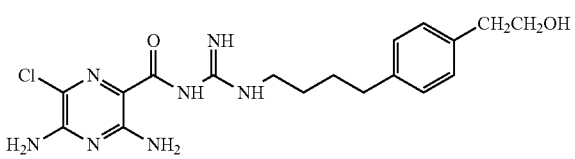

Using general procedure Z, 4-[4-(2-hydroxyethyl)phenyl)]butyl amine was converted into 4-[4-(2-hydroxyethyl)phenyl)]butylamidino-3,5-diamino-6-chloropyrazinecarboxamide hydrochloride, m.p. 218-219° C., API M/Z=406 [$C_{18}H_{24}ClN_7O_2H$]+.

Example 27

4-[3-(2-Hydroxyethyloxy)phenyl)butylamidino-3,5-diamino-6-chloropyrazinecarboxamide hydrochloride

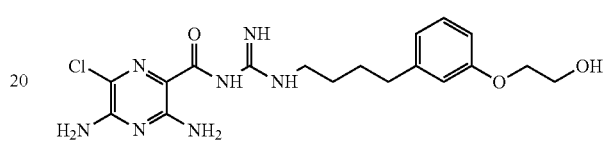

Using general procedure Z, 4-[3-(2-hydroxyethyloxy)phenyl)butyl amine was converted to 4-[(3-(2-hydroxyethyloxy)phenyl)]butylamidino-3,5-diamino-6-chloropyrazinecarboxamide hydrochloride, m.p. 161-163° C. (dec), AMPI MS M/Z=422[$C_{18}H_{24}ClN_7O_3$+H].+

References:

1. Taylor, E. C.; Harrington, P. M.; Schin, C. *Heterocycles,* 1989, 28, 1169, incorporated herein by reference 2. Widsheis et al, *Synthesis,* 1994, 87-92, incorporated herein by reference.

Sodium Channel Blocking Activity

The compounds shown in the Tables below were tested for potency in canine bronchial epithelia using the in vitro assay described above. Amiloride was also tested in this assay as a positive control. The results for the compounds of the present invention are reported as fold-enhancement values relative to amiloride.

Example 28

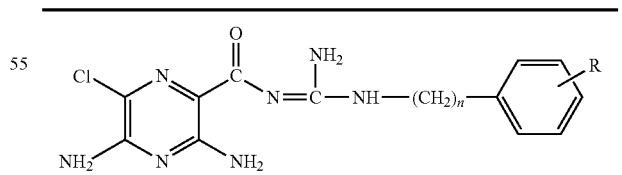

| n | Position of R | R | Fold Enhancement Over Amiloride |
|---|---|---|---|
| 2 | 4 | $NH_2$ | 12.7 |

Example 29

[Structure: chloropyrazine carboxamide with —N=C(NH₂)—NH—(CH₂)₄—C₆H₄—O—CH₂CH(OR)CH₂—OR]

| R | Fold Enhancement Over Amiloride |
|---|---|
| H | 124 |
| —C(=O)CH₃ | 36 |
| H₃CxCH₃* | 91 |

*= the R groups are bonded together via —C(CH₃)₂—

Example 30

[Structure: chloropyrazine carboxamide with —N=C(NH₂)—NH—(CH₂)₄—C₆H₄—O—(CH₂CH₂—O)$_n$—CH₃]

| n | Fold Enhancement Over Amiloride |
|---|---|
| 1 | 87 |
| 2 | 42 |
| 4 | 28.7 |

Example 31

[Structure: chloropyrazine carboxamide with —N=C(NH₂)—NH—(CH₂)₄—C₆H₄—R⁵]

| R⁵ | Fold Enhancement Over Amiloride |
|---|---|
| 40 | 65 |
| —O—SO₃H | 27.7 |
| —O-Glucuronide Na⁺ Salt | 11.2 |
| —CH₂OH | 57 |
| —CO₂CH₃ | 26.5 |

Example 32

Effect of Compound (33) from Example 3 on MCC

These experiments were conducted with compound (33) from Example 3, and the vehicle as a control. The results are shown in FIGS. 1 (t=0 hours) and 2 (t=4 hours).

Methods

Animal Preparation: Adult ewes (ranging in weight from 25 to 35 kg) were restrained in an upright position in a specialized body harness adapted to a modified shopping cart. The animals' heads were immobilized and local anesthesia of the nasal passage was induced with 2% lidocaine. The animals were then nasally intubated with a 7.5 mm internal diameter endotracheal tube (ETT). The cuff of the ETT was placed just below the vocal cords and its position was verified with a flexible bronchoscope. After intubation the animals were allowed to equilibrate for approximately 20 minutes prior to initiating measurements of mucociliary clearance.

Administration of Radio-aerosol: Aerosols of $^{99m}$Tc-Human serum albumin (3.1 mg/ml; containing approximately 20 mCi) were generated using a Raindrop Nebulizer which produces a droplet with a median aerodynamic diameter of 3.6 μm. The nebulizer was connected to a dosimetry system consisting of a solenoid valve and a source of compressed air (20 psi). The output of the nebulizer was directed into a plastic T connector; one end of which was connected to the endotracheal tube, the other was connected to a piston respirator. The system was activated for one second at the onset of the respirator's inspiratory cycle. The respirator was set at a tidal volume of 500 mL, an inspiratory to expiratory ratio of 1:1, and at a rate of 20 breaths per minute to maximize the central airway deposition. The sheep breathed the radio-labeled aerosol for 5 minutes. A gamma camera was used to measure the clearance of $^{99m}$Tc-Human serum albumin from the airways. The camera was positioned above the animal's back with the sheep in a natural upright position supported in a cart so that the field of image was perpendicular to the animal's spinal cord. External radio-labeled markers were placed on the sheep to ensure proper alignment under the gamma camera. All images were stored in a computer integrated with the gamma camera. A region of interest was traced over the image corresponding to the right lung of the sheep and the counts were recorded. The counts were corrected for decay and expressed as percentage of radioactivity present in the initial baseline image. The left lung was excluded from the analysis because its outlines are superimposed over the stomach and counts can be swallowed and enter the stomach as radio-labeled mucus.

Treatment Protocol (Assessment of activity at t-zero): A baseline deposition image was obtained immediately after radio-aerosol administration. At time zero, after acquisition of the baseline image, vehicle control (distilled water), positive control (amiloride), or experimental compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were extubated immediately following delivery of the total dose in order to prevent false elevations in counts caused by aspiration of excess radio-tracer from the ETT. Serial images of the lung were obtained at 15-minute intervals during the first 2 hours after dosing and hourly for the next 6 hours after dosing for a total observation period of 8 hours. A washout period of at least 7 days separated dosing sessions with different experimental agents.

Treatment Protocol (Assessment of Activity at t-4 Hours): The following variation of the standard protocol was used to assess the durability of response following a single exposure to vehicle control (distilled water), positive control compounds (amiloride or benzamil), or investigational agents. At time zero, vehicle control (distilled water), positive control (amiloride), or investigational compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were restrained in an upright position in a specialized body harness for 4 hours. At the end of the 4-hour period animals received a single dose of aerosolized $^{99m}$Tc-Human serum albumin (3.1 mg/ml; containing approximately 20 mCi) from a Raindrop Nebulizer. Animals were extubated immediately following delivery of the total dose of radio-tracer. A baseline deposition image was obtained immediately after radio-aerosol administration. Serial images of the lung were obtained at 15-minute intervals during the first 2 hours after administration of the radio-tracer (representing hours 4 through 6 after drug administration) and hourly for the next 2 hours after dosing for a total observation period of 4 hours.

A washout period of at least 7 days separated dosing sessions with different experimental agents.

Statistics: Data were analyzed using SYSTAT for Windows, version 5. Data were analyzed using a two-way repeated ANOVA (to assess overall effects), followed by a paried t-test to identify differences between specific pairs. Significance was accepted when P was less than or equal to 0.05. Slope values (calculated from data collected during the initial 45 minutes after dosing in the t-zero assessment) for mean MCC curves were calculated using linear least square regression to assess differences in the initial rates during the rapid clearance phase.

Example 33

Synthesis of N-(3,5-diamino-6-chloropyrazine-2-carbonyl)-N'-{4-[4-(2-guanidinoethoxy)-phenyl]butyl}guanidine dihydrochloride (9518)

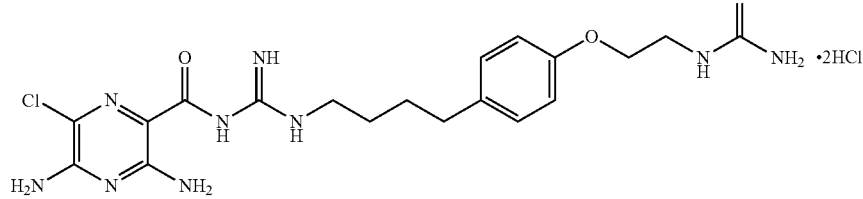

9518

{4-[4-(2-tert-Butoxycarbonylaminoethoxy)phenyl]butyl}carbamic acid benzyl ester (1)

Diisopropylazodicarboxylate (132 mL) was added dropwise over 45 minutes to a stirring mixture of [4-(4-hydroxyphenyl)butyl]carbamic acid benzyl ester (50 g, 0.167 mol), (2-hydroxyethyl)carbamic acid tert-butyl ester (103.4 mL, 0.668 mol), and THF (150 mL) with ice-methanol bath cooling from 15 to 35° C. When the exothermic reaction ceased, the cooling bath was removed, and the reaction was allowed to stir at room temperature overnight. The solvent was evaporated at reduced pressure, and the residue was applied to a 1 kg column of silica gel and eluted with methylene chloride. The chromatography was repeated twice. The residue after evaporation was washed with hexanes (1.5 L), and the resulting solid was re-crystallized from a mixture of hexanes and methylene chloride (4:1, 1 L) to afford 54 g (73%) of the pure product as a white solid. A second crop yielded an additional 10 g (13%) of the product. $^1$H NMR (300 MHz, CDCl$_3$) δ 1.45 (s, 9H), 1.56 (m, 4H), 2.56 (t, 2H), 3.20 (m, 2H), 3.50 (m, 2H), 3.98 (t, 2H), 4.75 (br s, 1H), 5.00 (br s, 1H), 5.09 (s, 2H), 6.80 (d, 2H), 7.06 (d, 2H), 7.34 (m, 5H).

{2-[4-(4-Aminobutyl)phenoxy]ethyl}carbamic acid ter-butyl ester (2)

{4-[4-(2-tert-Butoxycarbonylaminoethoxy)phenyl]butyl}carbamic acid benzyl ester 1 (2.5 g, 5.60 mmol), ethanol (20 mL), and 10% palladium on carbon (1 g), were subject to one atmosphere of hydrogen for 4 h, and then allowed to stand overnight. After stirring under nitrogen purge, the catalyst was removed by filtering the reaction mixture through Celite and rinsing with methylene chloride. Evaporation followed by 2 h under high vacuum afforded the product (1.7 g, 98%) as an oil. $^1$H NMR (300 MHz, CDCl$_3$) δ 1.45 (s, 9H), 1.47 (m, 2H), 1.61 (m, 2H), 1.75 (br s, 2H), 2.56 (t, 2H), 2.71 (t, 2H), 3.51 (m, 2H), 3.99 (t, 2H), 5.07 (br s, 1H), 6.80 (d, 2H), 7.08 (d, 2H).

[2-(4-{N'-(3,5-Diamino-6-chloropyrazine-2-carbonyl)guanidino]butyl}phenoxy)ethyl]-carbamic acid tert-butyl ester (3)

{2-[4-(4-Aminobutyl)phenoxy]ethyl}carbamic acid tert-butyl ester 2 (1.7 g, 5.5 mmol), 1-(3,5-diamino-6-chloropyrazine-2-carbonyl)-2-methylisothiourea hydroiodide (2.6 g, 6.6 mmol), and triethylamine (3.1 mL) were combined in THF (18 mL). The reaction was stirred at reflux under argon for 1.5 h. The product mixture was allowed to cool, and the solvent was evaporated. Chromatography (silica gel, methylene chloride/methanol/concentrated ammonium hydroxide, 100:10:1) afforded 2.65 g (92%) of the pure product as a yellow foamy solid. $^1$H NMR (300 MHz, CDCl$_3$) δ 1.44 (s, 9H), 1.62 (m, 2H), 1.61 (m, 2H), 1.75 (br s, 2H), 2.56 (t, 2H), 2.71 (t, 2H), 3.51 (m, 2H), 3.99 (t, 2H), 5.07 (br s, 1H), 6.80 (d, 2H), 7.08 (d, 2H).

N-{4-[4-(2-Aminoethoxy)phenyl]butyl}-N'-(3,5-diamino-6-chloropyrazine-2-carbonyl)-guanidine (4, 9308)

[2-(4-{(4-[N'-(3,5-Diamino-6-chloropyrazine-2-carbonyl)guanidino]butyl}phenoxy)ethyl]-carbamic acid tert-butyl ester 3 (2.63 g, 5.0 mmol) was dissolved in methanol (25 mL). 12N HCl (30 mL) was added in 10 ml portions. After stirring for 1 h, the reaction was complete by TLC (silica gel, methylene chloride/methanol/concentrated ammonium hydroxide, 100:10:1). The solvent was evaporated and methanol (300 mL) was added and, this process was repeated. The residue was placed under high vacuum overnight to afford the product (2.65 g, 99%) as a yellow solid, which was used without further manipulation. $^1$H NMR (300 MHz, DMSO-d$_6$) δ 1.58 (m, 4H), 2.57 (m, 2H), 3.16 (m, 2H), 3.37 (m, 2H), 4.18 (t, 2H), 6.91 (d, 2H), 7.15 (d, 2H), 7.45 (m, 4H), 8.45 (br s, 3H), 9.03 (br s, 2H), 9.46 (t, 1H), 10.63 (s, 1H).

N-(4-{4-[2-(N',N"-Di-tert-butoxycarbonylguanidino)ethoxy]phenyl}butyl)-N'-(3,5-diamino-6-chloropyrazine-2-carbonyl)guanidine (5)

Triethylamine (1.4 mL, 10 mmole) was dripped, via a syringe, into a stirring solution of N-{4-[4-(2-aminoethoxy)phenyl]butyl}-N'-(3,5-diamino-6-chloro-pyrazine-2-carbonyl)guanidine 4 (500 mg, 0.943 mmole) in methanol (3 mL). To this stirring solution was added 1,3-diBoc-2-(trifluoromethanesulfonyl)guanidine (Goodman's Reagent) (406 mg, 1.04 mmole), and this was allowed to stir at room temperature. After 2 h, TLC indicated the absence of Goodman's reagent. An additional 40 mg of the Goodman's reagent was added, and the reaction was stirred for additional 1 h. After evaporating at below 35° C., the crude product was chromatographed (silica gel, methylene chloride/methanol/concentrated ammonium hydroxide, 100:10:1) to obtain the pure product as a yellow solid. $^1$H NMR (300 MHz, CDCl$_3$) δ 1.49 (s, 9H), 1.51 (s, 9H), 1.67 (m, 4H), 2.58 (m, 2H), 3.22 (m, 2H), 3.82 (q, 2H), 4.05 (t, 2H), 5.22 (br s, 1H), 6.84 (d, 2H), 7.06 (d, 2H), 8.73 (t, 1H), 11.47 (br s, 1H).

N-(3,5-Diamino-6-chloropyrazine-2-carbonyl)-N'-{4-[4-(2-guanidinoethoxy)phenyl]butyl}-guanidine dihydrochloride (6)

12N HCl (15 mL) was added dropwise to an ice cooled solution of N-(4-{4-[2-(N',N"-di-tert-butoxycarbonylguanidino)ethoxy]phenyl}butyl)-N'-(3,5-diamino-6-chloropyrazine-2-carbonyl)-guanidine 5 (370 mg, 0.56 mmole) in methanol (15 mL) over 1 min. After the addition, the cooling bath was removed, and the reaction was allowed to stir for 30 min. TLC (silica gel, methylene chloride/methanol/concentrated ammonium hydroxide, 3:3:1) indicated slow reaction progression. An additional 15 mL of 12N HCl was added dropwise at room temperature, and after 2 h, TLC indicated reaction completion. The solvent was evaporated and methanol (100 mL) was added and then evaporated below 30° C., this process was repeated a further three times and then the residue was placed under vacuum at 40° C. for 2 days to afford 300 mg (96%) of the pure product as a yellow solid. $^1$H NMR (300 MHz, DMSO-d$_6$) δ 1.57 (m, 4H), 2.56 (m, 2H), 3.52 (m, 2H), 4.02 (t, 2H), 4.60 (br s, 2H), 6.88 (d, 2H), 7.14 (d, 2H), 7.41 (m, 8H), 7.91 (t, 1H), 8.93 (m, 2H), 9.33 (t, 1H), 10.55 (s, 1H). mp 223-230. m/z (ESI)=463 [C$_{19}$H$_{27}$ClN$_{10}$O$_2$+H]$^+$.

Example 34

N-[4-(4-{2-[bis-((2S,3R)-2,3,4-trihydroxybutyl)amino]ethoxy}phenyl)butyl]-N'-(3,5-diamino-6-chloropyrazine-2-carbonyl)guanidine dihydrochloride (10833)

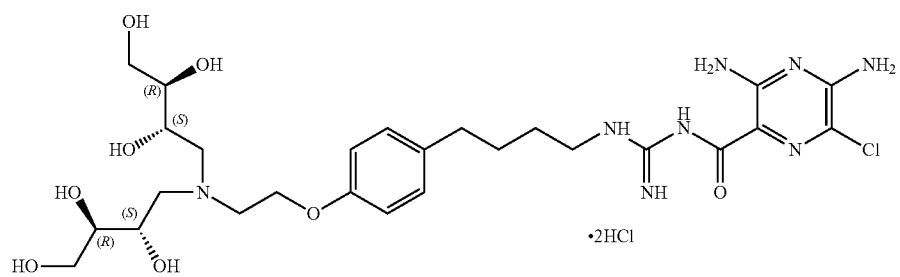

10833

Method A: via the reaction of {4-[4-(2-aminoethoxy)phenyl]butyl}carbamic acid benzyl ester 7 with D-(−)-erythrose.

{4-[4-(2-Aminoethoxy)phenyl]butyl}carbamic acid benzyl ester hydrochloride (7)

{4-[4-(2-tert-Butoxycarbonylaminoethoxy)phenyl] butyl}carbamic acid benzyl ester 1 (11.0 g, 24.9 mmol) was dissolved in methanol (110 mL) and THF (20 mL). 12N Hydrochloric acid (40 mL) was added dropwise, and the reaction was allowed to stir. After 1.5 h, ether (200 mL) was added, and the reaction was suction filtered to collect a white solid. The solid was washed with ether, air dried, and dried under vacuum. This afforded 7.6 g, (82%) of 7 as a white solid. $^1$H NMR (300 MHz, CD$_3$OD) δ 1.39 (br s, 11H), 1.52 (m, 2H),

4-[N,N-bis-((2S,3R)-2,3,4-trihydroxybutyl)-2-aminoethoxy]phenylbutylamine (9)

Acetic acid (0.18 mL, 3.08 mmol) and D-(−)-erythrose (0.74 g, 6.16 mmol) were sequentially added into a suspension of {4-[4-(2-aminoethoxy)phenyl]-butyl}carbamic acid benzyl ester hydrochloride 7 (0.58 g, 1.54 mmol) in methanol (20 mL). The reaction mixture was stirred for 20 minutes at room temperature and under nitrogen atmosphere; then sodium cyanoborohydride (0.39 g, 6.16 mmol) was added at −78° C. The reaction was allowed to warm up to room temperature. After overnight stirring, the solvent was evaporated and the residue was purified by Flash™ (BIOTAGE, Inc) (90 g silica gel cartridge 40M, 5:1:0.1 chloroform/methanol/concentrated ammonium hydroxide) to provide 8 (0.61 g, 72%) as a white solid. m/z (APCI)=551 [C$_{28}$H$_{42}$N$_2$O$_9$+H]$^+$.

The compound 8 (0.30 g, 0.55 mmol) was dissolved in methanol (30 mL) and stirred with 10% palladium on carbon (0.24 g. wet) for 4 h at room temperature and atmospheric pressure of hydrogen. The mixture was then filtered through a silica gel pad; the solvent was evaporated to provide 9 (0.21 g, 92%) as a white solid. $^1$H NMR (300 MHz, CD$_3$OD) δ 1.55 (m, 2H), 1.66 (m, 2H) 2.58 (m, 2H), 2.70 (m, 4H), 2.92 (m, 2H), 2.96 (m, 2H), 3.05 (m, 2H), 3.42 (m, 2H), 3.55 (m, 2H), 3.62 (m, 2H), 3.70 (m, 2H), 4.10 (m, 2H), 6.86 (d, 2H), 7.08 (d, 2H).

N-[4-(4-{2-[bis-((2S,3R)-2,3,4-trihydroxybutyl) amino]ethoxy}phenyl)butyl]-N'-(3,5-diamino-6-chloropyrazine-2-carbonyl)guanidine dihydrochloride (10)

1-(3,5-Diamino-6-chloropyrazinoyl)-2-methylisothiourea hydriodide (0.196 g, 0.5 mmol) and triethylamine (0.077 mL, 0.55 mmol) were sequentially added into a suspension of 9 (0.21 g, 0.5 mmol) in 10 mL of ethanol. The reaction mixture was stirred at 65° C. for 3 h; the solvent was then evaporated. The free base of the target compound 10 (0.166 g. 52%) was purified by Flash™ (BIOTAGE, Inc) (90 g silica gel cartridge 40M, 3:1:0.3 chloroform/ethanol/concentrated ammonium hydroxide) as a yellow solid. It was then treated with 3% HCl (2 mL). The precipitate was collected by filtration, washed with methylene chloride (4×5 mL), then taken into water (2 mL) and freeze-dried overnight to provide 152 mg (44%) of 10 as a yellow powder. $^1$H NMR (300 MHz, CD$_3$OD) δ 1.70 (br.s, 4H), 2.64 (m, 2H), 3.28 (m, 2H), 3.32 (br.s, 2H), 3.49 (m, 2H), 3.55-3.80 (m, 8H), 3.87 (m, 2H), 4.05 (m, 2H), 4.35 (m, 2H), 6.95 (d, 2H), 7.15 (d, 2H). m/z (APCI)=629 [C$_{26}$H$_{41}$ClN$_8$O$_8$+H]$^+$, [α]$_D^{25}$=−12.6° (c=1.03, MeOH).

Method B: via the reaction of N-{4-[4-(2-aminoethoxy) phenyl]butyl}-N'-(3,5-diamino-6-chloropyrazine-2-carbonyl)guanidine 4 with D-(−)-erythrose.

The compound 4 (0.2 g, 0.48 mmol) was suspended in 7 mL of methanol and D-(−)-erythrose (0.17 g, 1.4 mmol) dissolved in 0.9 mL of methanol was added. The reaction mixture was stirred at room temperature for 30 min. After this time 25 µL of acetic acid was added to give a clear solution. The reaction mixture was cooled to −78° C. and sodium cyanoborohydride (0.084 g, 1.4 mmol) was added. The reaction was stirred at −78° C. for 2 h and at room temperature for 3 d. After this time the solvent was removed under reduced pressure and 15 mL of water was added to the oily residue. The oil transformed into a yellow solid after 18 h in refrigerator. The solid was isolated by centrifugation, washed with water and dissolved in MeOH containing 0.05 mL of TFA. Silica gel (approx. 20 mL) was added and the solvent was removed under reduced pressure. The impregnated silica gel was submitted for purification using Flash™ (Biotage Inc., 90 g silica gel cartridge, eluent: chloroform/methanol/ammonium hydroxide=4:1:0.2). The resulting yellow solid was dissolved in 10 mL of 5% HCl and the solvent was removed under reduced pressure to give compound 10 (100 mg, 30%) as a yellow solid. $^1$H NMR (300 MHz, CD$_3$OD) δ 1.70 (br s, 4H), 2.64 (m, 2H), 3.29-3.70 (m, 20H), 4.07 (m, 2H) 4.37 (br s, 2H), 6.95 (d, 2H), 7.15 (d, 2H). m/z (APCI)=629 [C$_{26}$H$_{41}$ClN$_8$O$_8$+H]$^+$.

Methods C: via 2,4-ethylidene-D-erythrose
Method C. 1—precursor (11) constructed directly from pre-assembled amine (4)

N-[4-(4-{2-[Bis-((2R,4S,5R)-5-hydroxy-2-methyl[1,3]dioxan-4-ylmethyl)amino]-ethoxy}phenyl)butyl]-N'-(3,5-diamino-6-chloropyrazine-2-carbonyl)-guanidine (11)

The free base 4 (0.15 g, 0.35 mmol) was suspended in 6 mL of methanol. 2,4-Ethylidene-D-erythrose[1] (0.15 g, 1.05 mmol) in 2 mL of methanol was added, followed by the addition of 20 µL (0.35 mmol) of acetic acid. The mixture was stirred at room temperature until a clear solution was formed (approx. 10 min). The reaction solution was cooled to −78° C. and sodium cyanoborohydride (0.07 g, 1.05 mmol) was added. The reaction mixture was stirred at −78° C. for 2 h and at room temperature for 2d. After this time, the solvent was removed under reduced pressure and the residue purified by Flash™ (Biotage Inc., 90 g silica gel cartridge eluent: chloroform/methanol/ammonium hydroxide=10:1:0.1) to give 0.17 g (70%) of 11 as a yellow solid. $^1$H NMR (300 MHz, CD$_3$OD) δ 1.21 (m, 6H), 1.65 (br s., 4H), 2.59 (m, 2H), 2.84 (m, 2H), 2.92-3.60 (m, 12H), 4.03 (m, 4H), 6.84 (d, 2H), 7.10 (d, 2H). m/z (APCI)=681 [C$_{30}$H$_{45}$ClN$_8$O$_8$+H]$^+$.

Method C.2—precursor (11) constructed after side chain assembly

4-(4-{2-[Bis-((2R,4S,5R)-5-hydroxy-2-methyl[1,3] dioxan-4-ylmethyl)amino]ethoxy}phenyl)-butylcarbamic acid benzyl ester (12)

The compound 7 (0.5 g, 1.32 mmol) was suspended in 8 mL of methanol. 2,4-Ethylidene-D-erythrose (0.6 g, 4.1 mmol) in 2 mL of methanol was added, followed by the addition of 80 µL (1.32 mmol) of acetic acid. The mixture was stirred at room temperature until a clear solution was formed (approx. 10 min). The reaction solution was cooled to −78° C. and sodium cyanoborohydride (0.260 g, 1.05 mmol) was added. The reaction mixture was stirred at −78° C. for 2 h and at room temperature for 18 h. After this time, the solvent was removed under reduced pressure and the target compound 12 (0.6 g, 80%) was isolated by Flash™ (Biotage Inc., 90 g silica gel cartridge, eluent: dichlormethane/methanol/ammonium hydroxide=17:1:0.1) as a clear oil. $^1$H NMR (300 MHz, CD$_3$OD) δ 1.24 (m, 2H), 1.50 (m, 2H), 2.56 (m, 2H), 2.72 (m, 2H), 3.1 (m, 4H), 3.31-3.48 (m, 6H), 4.02 (m, 2H), 4.08 (m, 2H), 4.65 (m, 2H), 5.05 (s, 2H), 6.74 (d, 2H), 7.0.5 (d, 2H), 7.23 (m, 5H). m/z (APCI)=603 [C$_{32}$H$_{46}$ClN$_2$O$_9$+H]$^+$.

4-(4-{2-[Bis-((2R,4S,5R)-5-hydroxy-2-methyl[1,3] dioxan-4-ylmethyl)amino]ethoxy}phenyl)-butylamine (13)

The protected amine 12 was stirred at room temperature overnight in 25 mL of methanol with Pd/C (186 mg, 10% wet) under hydrogen (1 atm). After this time, the catalyst was filtered off and solvent removed under reduced pressure to give amine 13 (0.49 g, 93%) as a clear oil. The purity of 13 was confirmed by TLC on silica gel (eluent: chloroform/methanol/ammonium hydroxide=2.5:1:0.1).

N-[4-(4-{2-[Bis-((2R,4S,5R)-5-hydroxy-2-methyl[1,3]dioxan-4-ylmethyl)amino]ethoxy}-phenyl)butyl]-N'-(3,5-diamino-6-chloropyrazine-2-carbonyl)-guanidine (11)

1-(3,5-Diamino-6-chloropyrazinoyl-2-methylisothiourea hydriodide (0.39 g, 1.0 mmol) was added to a solution of 13 (0.49 g, 1.07 mmol) in THF (8 mL) containing diisopropylethylamine (0.18 mL, 2 mmol). The reaction mixture was stirred at reflux for 2.5 h and at room temperature overnight. After this time, the solvent was removed under reduced pressure. The brown residue was washed with ether (2×30 mL) and methylene chloride (2×10 mL). The residue was dissolved in a minimal volume of methanol (approx. 2 mL) and poured into water. The precipitate was collected, washed with water and dried overnight to give crude 11 (0.5 g) as a yellow solid. The compound 11 (0.4 g, 54%) was purified by flash chromatography on silica gel (eluent: chloroform/methanol/ammonium hydroxide=10:1:0.1) as a yellow solid. $[α]_D^{25}$=−20.4° (c=1.0, MeOH).

N-[4-(4-{2-[bis-((2S,3R)-2,3,4-trihydroxybutyl)amino]ethoxy}phenyl)butyl]-N'-(3,5-diamino-6-chloropyrazine-2-carbonyl)guanidine dihydrochloride (10)

The compound 11 (0.18 g, 0.26 mmol) was dissolved in 15 mL of 10% HCl and the reaction mixture was stirred at room temperature for 18 h. After this time the solvent was removed under reduced pressure. The resulting residue was dried overnight and purified by flash chromatography on silica gel (eluent: chloroform/methanol/ammonium hydroxide=3:1:0.3) to give 66 mg of a yellow solid. The solid was dissolved in 2.5 mL of 5% HCl and the solvent removed under reduced pressure. The residue was dissolved in 1.5 mL of methanol and the methanol solution was poured into 2-propyl alcohol. The formed precipitate was collected, washed with methylene chloride and dried in vacuum. 34 mg (18%) of dihydrochloride 10 was obtained. $^1$H NMR (300 MHz, CD$_3$OD) δ 1.71 (br s., 4H), 2.64 (m, 2H), 3.29-3.70 (m, 20H), 4.07 (m, 2H), 4.36 (br s., 2H), 6.96 (d, 2H), 7.16 (d, 2H). m/z (APCI)=629 [C$_{26}$H$_{41}$ClN$_8$O$_8$+H]$^+$; $[α]_D^{25}$=−12.6° (c=1.0, MeOH).

Method D: via (2R,3S)-3,4-epoxybutan-1,2-diol 4-(4-{2-[Bis-((2S,3R)-2,3,4-trihydroxybutyl)amino]ethoxyphenyl}butylamine (69)

A solution composed of {4-[4-(2-aminoethoxy)phenyl]butyl}carbamic acid tert-butyl ester 16$^1$ (0.21 g, 0.681 mmol) and (2R,3S)-3,4-epoxybutan-1,2-diol$^2$ (68) (0.177 g, 1.702 mmol) in ethanol (5 mL) was heated at 70° C. overnight. It was then slowly cooled to room temperature and treated with concentrated hydrochloric acid (12N, 6 mL) at room temperature for 3 hours. The reaction mixture was concentrated under vacuum. The residue was taken into ethanol (3 mL) and the resulting solution was concentrated again under vacuum. The procedure was repeated two more times to ensure no aqueous solvent remained. The residue was chromatographed over silica gel, eluting with a mixture of concentrated ammonium hydroxide (0-10%), methanol (0-30%), and methylene chloride (100-60%), to afford 0.273 g (89%) of the product 69 as a colorless viscous oil. $[α]_D^{25}$=−33.1° (c 1.0, MeOH). $^1$H NMR (300 MHz, CD$_3$OD) δ 1.49-1.61 (m, 4H), 2.53-2.73 (m, 5H), 2.90-3.04 (m, 4H), 3.52-3.73 (m, 17H), 4.07 (t, J=5.7 Hz, 2H), 6.84 (d, J=8.4 Hz, 2H), 7.07 (d, J=8.4 Hz, 2H). m/z (APCI)=417 [C$_{20}$H$_{36}$N$_2$O$_7$+H]$^+$.

N-[4-(4-{2-[Bis-((2S,3R)-2,3,4-trihydroxybutyl)amino]ethoxy}phenyl)butyl]-N'-(3,5-diamino-6-chloropyrazine-2-carbonyl)guanidine dihydrochloride (70, ALB 10833)

Compound 69 (0.112 g, 0.269 mmol) was mixed with ethanol (5 mL). The mixture was heated at 65° C. for 15 min to achieve complete dissolution. To the clear solution were sequentially added triethylamine (23 µL, 0.161 mmol) and 1-(3,5-diamino-6-chloropyrazinoyl)-2-methylisothiourea hydriodide (0.105 g, 0.269 mmol). The mixture was heated at 65° C. for an additional 2 hours. It was, while still warm, slowly added into methyl tert-butyl ether (MTBE, 25 mL) cooled by an ice bath. A light yellow precipitation immediately formed upon the addition of the reaction mixture. The suspension was allowed to warm up to room temperature by removing the ice bath, and the stirring was continued for one more hour. The solid was vacuum filtered, washed with MTBE (3×5 mL), and tried under vacuum for 4 hours. The dry material (0.155 g) was then suspended in ethanol (3 mL), and treated with concentrated HCl (1 mL). Water (3 mL) was added to completely dissolve the solid. The resulting solution was concentrated to dryness under vacuum. The residue was taken into methanol (2 mL). The resultant methanolic solution was added into 2-propyl alcohol (15 mL) at room temperature. The resulting light yellow suspension was stirred at room temperature overnight. The solid was then vacuum filtered, washed with 2-propyl alcohol (3×3 mL), and dried under vacuum. 0.093 g (49%) of the compound 70 was obtained as a light yellow solid. $[α]_D^{25}$=−13.9° (c 1.0, MeOH). $^1$H NMR (300 MHz, DMSO-d$_6$) δ 1.46-1.68 (m, 4H), 2.50-2.57 (m, 2H), 3.26-3.70 (m, 15H), 3.88-4.98 (m, 2H), 4.35-4.72 (m, 2H), 4.98-5.10 (br s, 2H), 5.50-6.70 (br s, 2H), 6.93 (d, J=8.3 Hz, 2H), 7.16 (d, J=8.3 Hz, 2H), 7.45 (br s, 2H), 7.84-8.06 (br s, 1H), 8.61 (br s, 1H), 8.81 (br s, 1H), 8.94 (br s, 1H), 9.25 (br s, 1H), 10.51 (br s, 1H). m/z (APCI)=629 [C$_{26}$H$_{41}$ClN$_8$O$_8$+H]$^+$.

Example 35

N-[4-(4-{2-[bis-((2R,3S)-2,3,4-trihydroxybutyl)amino]ethoxy}phenyl)-butyl]-N'-(3,5-diamino-6-chloropyrazine-2-carbonyl)guanidine dihydrochloride (14143, the enantiomer of 10833

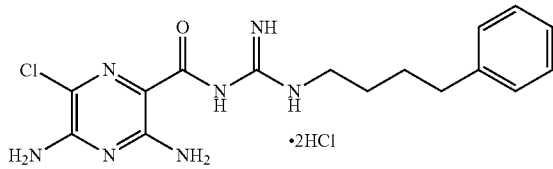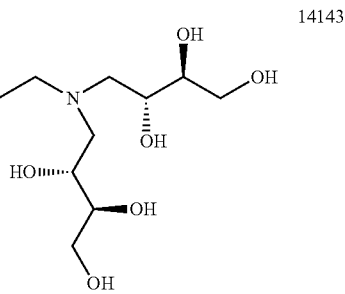

(2-Bromoethyl)carbamic acid benzyl ester (14)

Benzyl chloroformate (26 mL, 0.176 mole) was added in one portion to a stirring mixture of bromoethylamine hydrobromide (44 g, 0.21 mole), triethylamine (64 mL, 0.46 mole), and methylene chloride (1 L) at below −40° C. After the addition, the cooling bath was removed, and the reaction was allowed to stir for 3 h. The mixture was transferred to a 2 L separatory funnel, and sequentially washed with water (2×500 mL), 2N HCl (250 mL), and water (500 mL). The resulting solution was suction filtered through a 100 g pad of silica gel and washed with methylene chloride. Evaporation of the solvents afforded the product 14 (40 g, 89%) as an oil. $^1$H NMR (300 MHz, CDCl$_3$) δ 3.46 (t, 2H), 3.60 (q, 2H), 5.11 (s, 2H), 5.20 (br s, 1H), 7.35 (m, 5H).

{4-[4-(2-Benzyloxycarbonylaminoethoxy)phenyl]butyl}carbamic acid tert-butyl ester (15)

[4-(4-Hydroxyphenyl)butyl]carbamic acid tert-butyl ester (38 g, 0.143 mole), cesium carbonate (84 g, 0.257 mole), and (2-bromoethyl)carbamic acid benzyl ester 14 (59 g, 0.23 mole) were combined in DMF (200 ml). The mixture was mechanically stirred under nitrogen at 63° C. for 5.5 h, and allowed to stand at room temperature overnight. An additional amount of (2-bromoethyl)carbamic acid benzyl ester 14 (5 g, 0.019 mole) and cesium carbonate (7.1 g, 0.21 mole) were added, and the reaction was further stirred at 65° C. for 1 h. Toluene was then added, and the stirring mixture was allowed to cool to room temperature. The mixture was suction filtered through a medium sintered glass buchner funnel and washed with toluene. The solvents were removed under vacuum at 75° C. The remaining oil was washed with hexanes (2×400 mL), then dissolved in ether (500 ml) and washed with a mixture of water and brine (10:1, 4×100 mL). The remaining solution was suction filtered through a 30 g pad of silica gel and the solvent evaporated. The residue was washed with hexanes (3×400 ml), and then placed under vacuum for 2 h to afford 61.8 g of the product 15 which was used without further purification. $^1$H NMR (300 MHz, CDCl$_3$) δ 1.45 (s, 91H), 1.54 (m, 4H), 2.56 (t, 2H), 3.20 (m, 2H), 3.50 (m, 2H), 3.98 (t, 2H), 4.75 (br s, 1H), 5.00 (br s, 1H), 5.09 (s, 2H), 6.80 (d, 2H), 7.06 (d, 2H), 7.34 (m, 5H).

{4-[4-(2-Aminoethoxy)phenyl]butyl}carbamic acid tert-butyl ester (16)

{4-[4-(2-Benzyloxycarbonylaminoethoxy)phenyl]butyl}carbamic acid tert-butyl ester 15 (61.8 g) was stirred in ethanol (500 ml) with 10% palladium on carbon (6 g, wet), under one atmosphere of hydrogen. After stirring for more than 6 h, TLC (silica gel, methylene chloride/THF, 20:1) indicated reaction completion. The complete reaction was flushed with nitrogen, and suction filtered through a pad of Celite, and the pad washed with methylene chloride. The residue (41 g) after evaporation of the methylene chloride was applied to an 800 g pad of silica gel, and sequentially eluted with a mixture of THF and methylene chloride (1.4 L, 2:1), and a mixture of methylene chloride, methanol, and concentrated ammonium hydroxide (30:10:1, 2 L). The fraction containing the product was collected. Evaporation afforded the pure product 16 (32.8 g, 74% over 2 steps). $^1$H NMR (300 MHz, CDCl$_3$) δ 1.44 (s, 9H), 1.50 (br s, 2H), 1.55 (m, 4H), 2.56 (t, 2H), 3.12 (m, 2H), 3.50 (m, 2H), 3.98 (t, 2H), 4.75 (br s, 1H), 5.00 (br s, 1H), 5.09 (s, 2H), 6.80 (d, 2H), 7.06 (d, 2H), 7.34 (m, 5H).

[4-(4-{2-[Bis-((2R,3S)-2,3,4-trihydroxybutyl)amino]ethoxy}phenyl)butyl]carbamic acid tert-butyl ester (18)

A solution composed of the compound 16 (0.4 g, 1.297 mmol) and (2S,3R)-3,4-epoxybutan-1,2-diol$^2$ (17) (0.405 g, 3.891 mmol) in ethanol (6 mL) was heated at 60° C. overnight. It was then concentrated under vacuum. The residue was loaded onto silica gel, and eluted by a mixture of concentrated ammonium hydroxide (0-3%), methanol (0-30%), and methylene chloride (100-67%) to afford 0.592 g (88%) of the product 18 as a colorless viscous oil. $[α]_D^{25}$=+19.9° (c 0.84, MeOH). $^1$H NMR (300 MHz, CD$_3$OD): δ 1.32-1.67 (m, 13H), 2.54 (t, J=7.1 Hz, 2H), 2.72-2.79 (m, 2H), 2.94 (dd, J=13.2 Hz, 3.3 Hz, 2H), 3.02-3.09 (m, 2H), 3.51-3.55 (m, 4H), 3.59 (d, J=3.0 Hz, 2H), 3.67-3.74 (m, 4H), 4.08 (t, J=5.6 Hz, 2H), 4.63 (br, 1H), 6.86 (d, J=8.4 Hz, 2H), 7.07 (d, J=8.4 Hz, 2H). m/z (APCI)= 517 [C$_{25}$H$_{44}$N$_2$O$_9$+H]$^+$.

4-(4-{2-[Bis-((2R,3S)-2,3,4-trihydroxybutyl)amino]ethoxy}phenyl)butylamine (19)

To a solution containing the compound 18 (0.502 g, 0.972 mmol) in ethanol (10 mL) was slowly added concentrated hydrochloric acid (12N, 2 mL). The clear solution was stirred at room temperature for 4 hours. The reaction mixture was concentrated under vacuum. The residue was taken into ethanol (3 mL) and the resulting solution was concentrated again under vacuum. The procedure was repeated two more times to ensure no aqueous solvent remained. The residue was chromatographed over silica gel, eluting with a mixture of concentrated ammonium hydroxide (0-10%), methane (0-30%), and methylene chloride (100-60%), to afford 0.396 g (98%) of the product 19 as a low melting white solid.

$[α]_D^{25}$=+24.2° (c 0.265, MeOH). $^1$H NMR (300 MHz, DMSO-$d_6$): δ 1.32-1.52 (m, 4H), 2.46-2.55 (m, 4H), 2.74-2.79 (m, 2H), 2.84-2.96 (m, 2H), 3.31-3.99 (m, 16H), 4.01 (t, J=5.9 Hz, 2H), 6.40 (br s, 2H), 6.82 (d, J=8.5 Hz, 2H), 7.09 (d, J=8.5 Hz, 2H). m/z (APCI)=417 $[C_{20}H_{36}N_2O_7+H]^+$.

N-[4-(4-{2-[Bis-((2R,3S)-2,3,4-trihydroxybutyl)amino]ethoxy}phenyl)butyl]-N'-(3,5-diamino-6-chloropyrazine-2-carbonyl)guanidine (20, ALB 14143)

The compound 19 (0.15 g, 0.331 mmol) was mixed with ethanol (5 mL). The mixture was heated at 65° C. for 15 min to achieve complete dissolution. To the clear solution were sequentially added di-isopropylethylamine (0.26 mL, 1.505 mmol) and 1-(3,5-diamino-6-chloropyrazinoyl)-2-methyl-isothiourea hydriodide (0.117 g, 0.301 mmol). The mixture was heated at 65° C. for an additional 2 hours, and subsequently concentrated under vacuum. The residue was chromatographed over silica gel, eluting with a mixture of concentrated ammonium hydroxide (1-7%), methanol (10-30%), and methylene chloride (89-63%), to afford 0.152 g (80%) of the free base of 20 as a yellow solid. mp 78-80° C. (decomposed), $[α]_D^{25}$=+19.3° (c 1.075, MeOH). $^1$H NMR (300 MHz, DMSO-$d_6$): δ 1.46-1.68 (m, 4H), 2.48-2.62 (m, 2H), 2.74-2.95 (m, 4H), 3.08-3.19 (m, 2H), 3.26-3.70 (m, 12H), 4.03 (t, J=5.9 Hz, 2H), 4.35-4.72 (m, 6H), 6.60-6.74 (br s, 3H), 6.83 (d, J=8.3 Hz, 2H), 7.11 (d, J=8.3 Hz, 2H), 9.05 (br s, 2H). m/z (APCI)=629 $[C_{26}H_{41cl}N_8O_8+H]^+$.

A sample of the free base of the compound 20 (0.2 g) was treated with 2N HCl (8 mL). The solution was concentrated to dryness under vacuum. The residue was taken into methanol (2 mL). The resultant methanolic solution was added into 2-propyl alcohol (15 mL) at room temperature, resulting in a light yellow suspension. The solid was vacuum filtered, washed with 2-propyl alcohol (3×3 mL), and dried under vacuum. 0.21 g (94%) of the compound 20 was obtained as a light yellow solid. mp 93-96° C. (decomposed); $[α]_D^{25}$=+9.06° (c 1.17, MeOH). $^1$H NMR (300 MHz, DMSO-$d_6$): δ 1.46-1.68 (m, 4H), 2.48-2.62 (m, 2H), 3.26-3.70 (m, 17H), 4.03 (t, J=5.9 Hz, 2H), 4.35-4.72 (m, 2H), 4.98-5.10 (m 2H), 5.50-6.70 (br s, 2H), 6.94 (d, J=8.3 Hz, 2H), 7.14 (d, J=8.3 Hz, 2H), 7.40 (br s, 1H), 7.42-7.67 (br s, 1H), 8.68-8.89 (br s, 2H), 9.31 (br s, 1H), 10.53 (br s, 1H). m/z (APCI)=629 $[C_{26}H_{41}ClN_8O_8+H]^+$.

Example 36

N-[4-(4-{2-[(2S,3R)-2,3,4-trihydroxybutylamino]ethoxy}phenyl)butyl]-N'-(3,5-diamino-6-chloropyrazine-2-carbonyl)guanidine dihydrochloride (10733)

N-[4-(4-{2-[(2S,3R)-2,3,4-trihydroxybutylamino]ethoxy}phenyl)butyl]-N'-(3,5-diamino-6-chloropyrazine-2-carbonyl)guanidine dihydrochloride (22)

The free base 4 (0.3 g, 0.71 mmol) was suspended in 12 mL of methanol and 0.09 mL (1.4 mmol) of AcOH was added. The mixture was stirred at room temperature until a clear solution was formed. 2,4-Ethylidene-D-erythrose (0.13 g, 0.92 mmol) was then added. The reaction solution was cooled to −78° C. and sodium cyanoborohydride (0.06 g, 0.92 mmol) was added. The reaction mixture was stirred at −78° C. for 2 h and then at room temperature for 18 h. After this time the solvent was removed under reduced pressure and the residue purified by Flash™ (Biotage Inc., 90 g silica gel cartridge eluent: chloroform/methanol/ammonium hydroxide=15:1:0.1) to give 0.26 g (66%) of 21 as a yellow solid. A sample of the compound 21 (0.2 g, 0.36 mmol) was then dissolved in methanol (15 mL) and 300 mg of acidic resin (Dowex 50 WX8-200) was added. The mixture was stirred at room temperature for 2 d. After this time, the resin was filtered off and washed with methanol. Then the resin was washed with a 1:1 mixture of MeOH/NH$_4$OH, (2×20 mL) and filtered off. The supernatants were combined and the solvent was removed under reduced pressure. The residue was purified by flash chromatography on silica gel (eluent: chloroform/methanol/ammonium hydroxide=3:1:0.3). The obtained compound was dried overnight. After this time, the dry residue was dissolved in 5% HCl. Solvent was removed under reduced pressure and the formed yellow solid was dried overnight to give compound 22 (0.12 g, 55%). $^1$H NMR (300 MHz, CD$_3$OD) δ 1.68 (br s., 4H), 2.64 (m, 2H), 3.15-3.75 (m, 11H), 3.95 (m, 1H), 6.94 (d, 2H), 7.18 (d, 2H), 9.23 (m, 1H). m/z (APCI)=525 $[C_{22}H_{33}ClN_8O_8+H]^+$.

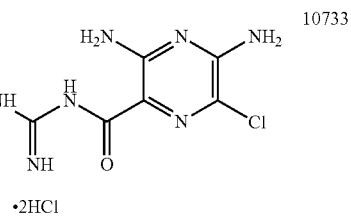

10733

·2HCl

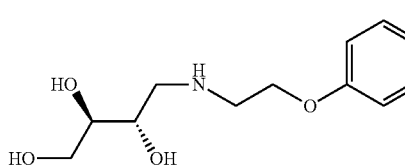

Example 37

N-[4-(4-{2-[bis-((2R,3S,4R)-2,3,4,5-tetrahydroxy-pentyl)amino]ethoxy}-phenyl)butyl]-N'-(3,5-di-amino-6-chloropyrazine-2-carbonyl)guanidine dihydrochloride (4330)

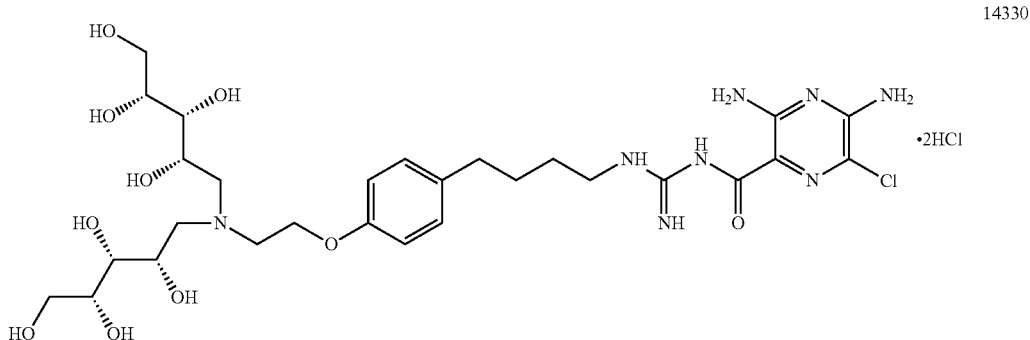 [SMILES: N=C(NCCCCc1ccc(OCCN(C[C@H](O)[C@@H](O)[C@H](O)CO)C[C@H](O)[C@@H](O)[C@H](O)CO)cc1)NC(=O)c1nc(Cl)c(N)nc1N]

N-[4-(4-{2-[bis-((2R,3S,4R)-2,3,4,5-tetrahydroxy-pentyl)amino]ethoxy}-phenyl)butyl]-N'-(3,5-di-amino-6-chloropyrazine-2-carbonyl)guanidine dihydrochloride (23)

D-(+)-xylose (0.35 g, 2.6 mmol) was added to a solution of hydrochloride 4 (0.3 g, 0.65 mmol) in methanol (20 mL) and the mixture was stirred for 20 min at room temperature. Then the solution was cooled to −78° C. and sodium cyanoborohydride (0.17 g, 2.6 mmol) was added. The reaction mixture was stirred at −78° C. for 2 h and at room temperature for 4 d. After this time, the solvent was removed under reduced pressure and the residue was washed with water. The formed yellow solid was isolated and dried under vacuum. Then the residue was re-dissolved in 5% HCl and the solvent was removed at reduced pressure. The obtained compound was dissolved in water containing 0.1% TFA and purified by preparative HPLC (C 18 Luna column from Phenomenex 250×21.2 mm, 5μ, isocratic method, water/acetonitrile=80%:20%). The fractions containing the target compound were combined and the solvent was removed under reduced pressure. The residue was dissolved in 5% HCl and solvent was removed under reduced pressure (twice). The resulting yellow powder was dissolved in water and the solution was lyophilized to give 34 mg (7%) of compound 23 as a yellow solid. $^1$H NMR (300 MHz, CD$_3$OD) δ 1.64 (br s., 4H), 2.62 (m, 2H), 3.30 (m, 4H), 3.35-3.70 (m, 13H), 4.23 (m, 2H), 4.47 (m, 2H), 6.95 (d, 2H), 7.15 (d, 2H). m/z (APCI) 689 [C$_{28}$H$_{45}$ClN$_8$O$_{10}$+H]$^+$. [α]$_D^{25}$=−16.1° (c=0.5, MeOH).

Example 38

4-{4-[N-(3,5-diamino-6-chloropyrazine-2-carbonyl)guanidino]butyl}-N-(2-hydroxyethyl)benzamide hydrochloride (11180)

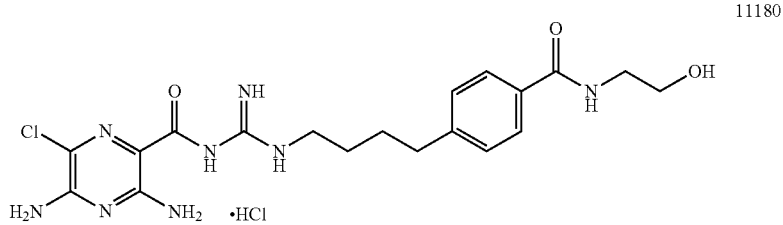 [SMILES: N=C(NCCCCc1ccc(C(=O)NCCO)cc1)NC(=O)c1nc(Cl)c(N)nc1N ; Cl]

The synthesis of 4-(4-Carboxymethylphenyl)butylamine (24) was described in the previous previously provided experimental details (as compound 8).

4-(4-tert-Butoxycarbonylaminobutyl)benzoic acid methyl ester (25)

Di-tert-butyl dicarbonate (1.64 g, 7.51 mmol) was added into the solution of 24 (1 g, 4.84 mmol) in anhydrous methylene chloride (50 mL). The reaction mixture was stirred overnight under an argon atmosphere at room temperature. Then the solvent was removed under reduced pressure. The residue was separated by Flash™ (BIOTAGE, Inc) (90 g silica gel cartridge 40M, 3:1 hexane/ethyl acetate) to provide 25 as a white solid (1.35 g, 91%). $^1$H NMR (300 MHz, CDCl$_3$) δ 1.42 (s, 9H), 1.52 (m, 2H), 1.64 (m, 2H), 2.69 (m, 2H), 3.13 (m, 2H), 3.90 (s, 3H), 4.57 (br s, 1N), 7.22 (d, 2H), 7.95 (d, 2H).

4-(4-tert-butoxycarbonylaminobutyl)benzoic acid (26)

An aqueous (10 mL) solution of sodium hydroxide (0.53 g, 13.18 mmol) was added into the solution of 25 (1.35 g, 4.39 mmol) in THF (60 mL) and the resulting solution was stirred at room temperature for 48 h and at 60° C. for 14 h. Then the solvent was removed under reduced pressure. Water (20 mL) was added and pH was adjusted to 7 with HCl. The white solid precipitate was filtered off, washed with water and dried under vacuum. 1.22 g (95%) of white solid 26 was obtained. $^1$H NMR (300 MHz, DMSO-d$_6$) δ 1.39 (br s, 11H), 1.52 (m, 2H), 1.64 (m, 2H), 2.92 (m, 2H), 6.84 (m, 1H), 7.28 (d, 2H), 7.85 (d, 2H).

{4-[4-(2-Hydroxyethylcarbamoyl)phenyl]butyl}carbamic acid tert-butyl ester (27)

1,1'-Carbonyldiimidazole (0.6 g, 3.71 mmol) was added into the solution of 26 (0.91 g, 3.09 mmol) in THF (50 mL). The reaction mixture was stirred at room temperature overnight under argon atmosphere, then ethanolamine (0.28 mL, 4.64 mmol) was added. The stirring was continued for 24 h at room temperature and argon atmosphere. The solvent was evaporated and the residue was purified by Flash™ (BIOTAGE, Inc) (90 g silica gel cartridge 40M, 18:1:0.1 chloroform/ethanol/concentrated ammonium hydroxide). 074 g (71%) of a white solid 27 was isolated. $^1$H NMR (300 MHz, CDCl$_3$) δ 1.40 (s, 9H), 1.48 (m, 2H), 1.60 (m, 2H), 2.62 (m, 2H), 3.10 (m, 2H), 3.79 (m, 2H), 4.55 (br s, 1H), 6.74 (m, 1H), 7.18 (d, 2H), 7.66 (d, 2H).

4-(4-Aminobutyl)-N-(2-hydroxyethyl)benzamide hydrochloride (28)

A solution of 27 (0.4 g, 1.19 mmol) was stirred at room temperature in a mixture of methanol/HCl (1:1, 40 mL). The reaction was finished in 2 h according to HPLC analysis. The solvent was removed under reduced pressure to provide 0.33 g (98%) 28 as a white solid. $^1$H NMR (300 MHz, DMSO-d$_6$) δ 1.60 (m, 4H), 2.63 (m, 2H), 2.78 (m, 2H), 3.31 (m, 2H), 3.50 (m, 2H), 7.28 (d, 2H), 7.80 (d, 2H), 7.97 (br s, 2H), 8.46 (m, 1H).

4-{4-[N-(3,5-Diamino-6-chloropyrazine-2-carbonyl)guanidino]butyl}-N-(2-hydroxy-ethyl)benzamide hydrochloride (29)

1-(3,5-Diamino-6-chloropyrazinoyl)-2-methylisothiourea hydriodide (0.48 g, 1.24 mmol) and triethylamine (0.7 mL, 4.74 mmol) were sequentially added into a solution of 28 (0.28 g, 1.19 mmol) in a mixture of THF/MeOH (4 mL, 1/1). The reaction mixture was stirred in the boiling solvent for 4 h, then at room temperature overnight. The solvent was evaporated. The free base of the target compound 29 (0.36 g, 62%) was purified by Flash™ (BIOTAGE, Inc) (90 g silica gel cartridge 40M, 12:1:0.1 chloroform/ethanol/concentrated ammonium hydroxide) as a yellow solid. 100 mg of the yellow solid was treated with 2 mL of 3% HCl. The precipitate was collected by filtration, washed with water (2×5 mL) and dried under vacuum to give 85 mg (79%) of 29 as a yellow powder. $^1$H NMR (300 MHz, DMSO-d$_6$) δ 1.60 (m, 4H), 2.68 (m, 2H), 3.28 (m, 4H), 3.49 (m, 2H), 4.80 (m, 1H), 7.28 (d, 2H), 7.44 (br s, 2H), 7.82 (d, 2H), 8.45 (m, 1H). m/z (APCI)=449 [C$_{19}$H$_{25}$ClN$_8$O$_3$+H]$^+$.

Example 39

2-{4-[N'-(3,5-diamino-6-chloropyrazine-2-carbonyl)guanidino]-4-butylphenoxy}acetamide hydrochloride (9714)

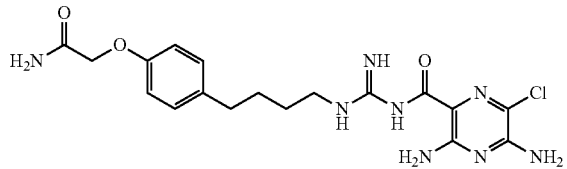

9714

[4-(4-Benzyloxycarbonylaminobutyl)phenoxy]acetic acid ethyl ester (47)

Sodium hydride (60% dispersion in mineral oil) (0.24 g, 10.05 mmol) was added to a cold (0° C.) solution of 4-(4-hydroxyphenyl)butylamine (2 g, 6.68 mmol) in THF (150 mL) under nitrogen atmosphere. The reaction mixture was allowed to warm up to room temperature over 0.5 h with stirring, then ethyl bromoacetate (0.96 mL, 8.02 mmol) and tetrabutylammonium iodide (0.25 g, 0.67 mmol) was sequentially added. The reaction was further stirred at room temperature overnight. Silica gel (25 mL) was added into the mixture and the solvent was evaporated. The impregnated silica gel was subjected to column chromatography purification (silica gel, 5:1 hexanes/ethyl acetate). 2.42 g (94%) of 47 was obtained as a white solid. $^1$H NMR (300 MHz, CDCl$_3$) δ 1.30 (t, 3H), 1.57 (m, 4H), 2.58 (m, 2H), 3.20 (m, 2H), 4.28 (m, 2H), 4.58 (s, 2H), 4.74 (br s, 1H), 5.10 (br s, 2H), 6.82 (m, 2H), 7.08 (m, 2H), 7.38 (br s, 5H).

[4-(4-Aminobutyl)phenoxy]acetic acid ethyl ester (48)

A suspension of 47 (1.11 g, 2.88 mmol) and 10% palladium on carbon (0.40 g, wet) in methanol (50 mL) was stirred at room temperature for 2 h under atmospheric pressure of hydrogen. The mixture was then filtered through a silica gel pad. The solvent was evaporated to provide 48 (0.64 g, 88%) as a white solid. $^1$H NMR (300 MHz, DMSO-d$_6$) δ 1.21 (m, 3H), 1.30-1.63 (m, 6H), 3.13 (m, 2H), 4.17 (m, 2H), 4.72 (br s, 2H), 6.84 (m, 21H), 7.10 (m, 2H).

(4-{4-[N'-(3,5-Diamino-6-chloropyrazine-2-carbonyl)guanidino]butyl}phenoxy)acetic acid ethyl ester (49)

1-(3,5-Diamino-6-chloropyrazinoyl)-2-methylisothiourea hydriodide (0.74 g, 1.9 mmol) and triethylamine (0.5 mL) were sequentially added into a solution of 48 (0.62 g, 2.47 mmol) in THF (10 mL). The reaction mixture was stirred in the boiling solvent for 4 h and at room temperature overnight. The solvent was evaporated and the residue was purified by column chromatography (silica gel, 6:1:0.1 chloroform/ethanol/concentrated ammonium hydroxide) to provide 49 (0.5 g, 57%) as a yellow solid. The purity of the product was confirmed by HPLC. m/z (APCI)=464 [C$_{20}$H$_{26}$ClN$_7$O$_4$+H]$^+$.

2-{4-[N'-(3,5-Diamino-6-chloropyrazine-2-carbonyl)guanidino]-4-butylphenoxy}acetamide hydrochloride (50, 9714)

A solution of 49 (0.5 g, 1.08 mmol) in ammonia-saturated ethanol (100 mL) was stirred at room temperature overnight. The solvent was evaporated and the residue was purified by column chromatography (silica gel, 4:1:0.1 chloroform/ethanol/concentrated ammonium hydroxide) to afford the free base of the product 50 as a yellow solid. It was then treated with 3% HCl. The solvent was evaporated. The resulting solid was washed with water (2×5 mL), and then dried in vacuum to provide 50 (0.25 g, 49%) as a yellow solid. $^1$H NMR (300 MHz, DMSO-$d_6$) δ 1.57 (br s, 4H), 2.51 (m, 2H), 3.33 (m, 2H), 4.48 (s, 2H), 6.87 (d, 2H), 7.13 (d, 2H), 7.37-7.60 (m, 4H), 8.88 (br s, 1H), 8.99 (br s, 1H), 9.32 (m, 1H), 10.56 (s, 1H). m/z (APCI)=435.3 [$C_{18}H_{23}ClN_8O_3$+H]$^+$.

Example 40

4-{4-[N'-(3,5-Diamino-6-chloropyrazine-2-carbonyl)guanidino]butyl}benzamidine (11157)

11157

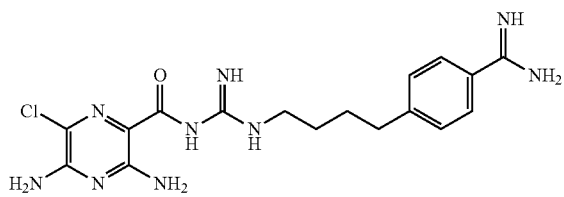

[4-(4-Cyanophenyl)but-3-ynyl]carbamic acid tert-butyl ester (56)

But-3-ynylcarbamic acid tert-butyl ester (3.66 g, 22 mmol) was added dropwise to an ice cooled, stirring, argon purged mixture of 4-iodobenzonitrile (4.5 g, 19.6 mmol), dichlorobis(triphenylphosphine)palladium(II) (0.69 g, 0.98 mmol), copper (1) iodide (0.19 g, 0.98 mmol), triethylamine (11 mL, 78.4 mmol), and THF (24 mL). After stirring for 10 min, the ice bath was removed, and the reaction was allowed to stir for an additional 2 h. The reaction mixture was passed through a pad of silica gel with methylene chloride/ethyl acetate (5:1) as eluant. After evaporating the solvent, the crude product was chromatographed with methylene chloride/ethyl acetate (20:1) as eluant. Evaporation of the solvent, followed by placement under vacuum for 1 h, afforded the pure product 56 (5.2 g, 99%) as an oil. $^1$H NMR (300 MHz, CDCl$_3$) δ 1.46 (s, 9H), 2.64 (t, 2H), 3.37 (m, 2H), 4.85 (br s, 1H), 7.47 (d, 2H), 7.58 (d, 2H).

[4-(4-Cyanophenyl)butyl]carbamic acid tert-butyl ester (57)

A suspension of [4-(4-cyanophenyl)but-3-ynyl]carbamic acid tert-butyl ester 56 (5.2 g, 19.2 mmol) and 10% palladium on carbon (2.5 g, wet) in ethanol/THF (30 mL, 1:1) was stirred overnight under 1 atmosphere of hydrogen. After purging with nitrogen, the reaction mixture was suction filtered through a pad of Celite. The solvent was removed from the filtrate by evaporation. The residue was chromatographed on silica gel, eluting with methylene chloride/ethyl acetate (30:1), to afford the pure product 57 (4.6 g, 87%) as an oil. $^1$H NMR (300 MHz, CDCl$_3$) δ 1.44 (s, 9H), 1.51 (m, 2H), 1.65 (m, 2H), 2.69 (t, 2H), 3.14 (m, 2H), 4.52 (br s, 1H), 7.27 (d, 2H), 7.56 (d, 2H).

[4-(4-Thiocarbamoylphenyl)butyl]carbamic acid tert-butyl ester (58)

Nitrogen was bubbled through a stirring solution of [4-(4-cyanophenyl)butyl]carbamic acid tert-butyl ester (57) (4.5 g, 16.4 mmol), pyridine (60 mL), and triethylamine (60 mL) for 10 min. Hydrogen sulfide was slowly bubbled through this stirring solution for 10 min. The reaction was sealed, and allowed to stir overnight. The reaction mixture was then purged with nitrogen, transferred to a separatory funnel with ethyl acetate (500 mL), and sequentially washed with water (3×100 mL), saturated aqueous solution of potassium hydrogen sulfate (3×100 mL), water (2×50 mL), and brine (2×50 mL). The solution was dried over sodium sulfate. The solid was filtered, and the filtrate was concentrated under reduced pressure. The resulting solid was re-crystallized from hexanes/ethyl acetate (10:1), and placed under vacuum for 2 h to afford the pure product 58 (4.8 g, 95%) as a yellow crystalline solid. $^1$H NMR (300 MHz, CDCl$_3$) δ 1.43 (s, 9H), 1.49 (m, 2H), 1.63 (m, 2H), 2.65 (t, 2H), 3.11 (m, 2H), 4.57 (br s, 1), 7.19 (d, 2H), 7.42 (br s, 1H), 7.81 (d, 2H).

[4-(4-Carbamimidoylphenyl)butyl]carbamic acid tert-butyl ester (59)

[4-(4-Thiocarbamoylphenyl)butyl]carbamic acid tert-butyl ester (58) (500 mg, 1.6 mmol) and iodomethane (4 mL, 64 mmol) were combined in methylene chloride (8 mL). The solution was stirred at reflux for 3 h, and allowed to stand overnight. The volatiles were removed by evaporation, and the residue was dried under vacuum for 3 h. The resulting crystalline solid was dissolved in ethanol (5 mL), and ammonium acetate (1.1 g, 14.4 mmol) was added. The resulting solution was stirred at reflux for 2 h, and the solvent was evaporated. The residue was taken up in a mixture of methanol and concentrated ammonium hydroxide (20 mL, 10:1), and the solvent was then evaporated. To this residue were added water (20 mL) and concentrated ammonium hydroxide (3 mL). The resulting mixture was stirred for 1 h, cooled in an ice bath, and suction filtered to collect a solid. The solid was dried under vacuum overnight to afford the product 59 (137 mg, 29%). $^1$H NMR (300 MHz, DMSO-$d_6$) δ 1.37 (s, 9H), 1.38 (m, 2H), 1.55 (m, 2H), 2.64 (t, 2H), 2.93 (m, 2H), 6.80 (br s, 1H), 7.35 (d, 2H), 7.70 (d, 2H), 9.62 (br s, 3H).

4-(4-Aminobutyl)benzamidine dihydrochloride (60)

12 N hydrochloric acid (0.71 mL, 8.6 mmol) was added dropwise into a stirring solution of [4-(4-carbamimidoylphenyl)butyl]carbamic acid tert-butyl ester (59) (124 mg, 0.43 mmol) in methanol (2 mL). After stirring for 2.5 h, TLC (methylene chloride/methanol/concentrated ammonium hydroxide, 6:3:1) indicated reaction completion. The reaction mixture was vacuum filtered. The solvent was removed from the filtrate by evaporation. Residual water was further removed as an azeotrope of toluene/methanol (1:1). Placement of the residue under vacuum for 2 h afforded the product 60 (106 mg, 94%) as a yellow foamy solid. $^1$H NMR (300 MHz, DMSO-$d_6$) δ 1.62 (m, 4H), 2.70 (t, 2H), 2.78 (m, 2H), 3.49 (br s, 1H), 7.47 (d, 2H), 7.82 (d, 2H), 8.13 (br s, 3H), 9.25 (s, 2H), 9.42 (s, 2H).

4-{4-[N'-(3,5-Diamino-6-chloropyrazine-2-carbonyl)guanidino]butyl}benzamidine (61, ALB 11157)

4-(4-Aminobutyl)benzamidine dihydrochloride (60) (92 mg, 0.35 mmol), triethylamine (0.24 mL, 1.74 mmol), 1-(3,5-diamino-6-chloropyrazinoyl)-2-methylisothiourea hydriodide (142 mg, 0.37 mmol) were sequentially added into ethanol (2 mL). After stirring at reflux for 2 h with argon protection, the solvent was evaporated. The residue was stirred in methylene chloride (5 mL), and suction filtered to obtain a solid. The solid was chromatographed on silica gel, eluting with methylene chloride/methanol/concentrated ammonium hydroxide (6:3:1), to afford the pure product 61 as a yellow solid. mp 140-170° C. (decomposed). $^1$H NMR (300 MHz, DMSO-$d_6$) δ 1.96 (m, 2H), 2.09 (m, 2H), 3.43 (m, 2H), 4.08 (br s, 2H), 8.00-10.00 (m, 14H). m/z (APCI)= 404 $(C_{17}H_{22}ClN_9O+H)^+$.

References.

1. Rappoport, D. A.; Hassid, Z.; J. Amer. Chem. Soc., 1951, 73, 5524-5525, incorporated herein by reference, Ruth, J. A. and Claffey, D. J., *Tetrahedron Lett.* 1996, 37 (44), 7929-7932, incorporated herein by reference.

Sodium Channel Blocking Activity

The compounds shown in the Table below were tested for potency in canine bronchial epithelia using the in vitro assay described above. Amiloride was also tested in this assay as a positive control. The results for the compounds of the present invention are reported as fold-enhancement values relative to amiloride.

Example 41

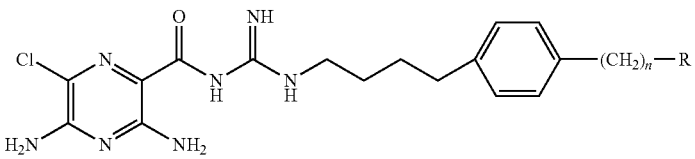

| R = | N = | Fold Amiloride* |
|---|---|---|
| OH | 1 | 50.9 ± 19.8 (3) |
| OH | 2 | 79.2 ± 30.6 (4) |
| OH | 4 | 45.3 ± 27.0 (6) |
| $NH_2$ | 0 | 32.6 ± 2.0 (3) |
| $NH_2$ | 1 | 26.2 ± 5.1 (3) |
| $NH_2$ | 3 | 59 ± 5.5 (4) |
| $NH_2$ | 4 | 132.6 ± 47.2 (5) |

Example 42

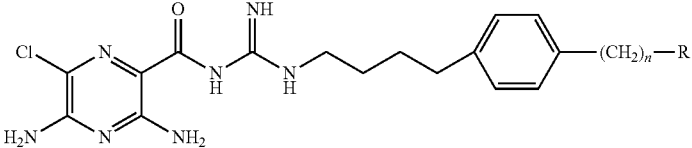

| R = | n = | Fold Amiloride* |
|---|---|---|
| OH | 2 | 84.9 ± 30.3 (6) |
| OH | 3 | 105.2 ± 26.6 (7) |
| OH | 4 | 21 (1) |
| $NH_2$ | 2 | 60.1 ± 1.3 (2) |
| $NH_2$ | 2 | 56.5 ± 0 (4) |
| $NH_2$ | 3 | 102.6 ± 49 (2) |

Example 43

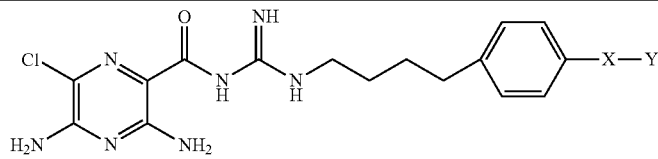

| X = | Y = | Fold Amiloride* |
|---|---|---|
| C=O | $NH_2$ | 73.1 ± 31.5 (3) |
| C=O | $NH(CH_2)_2$—OH | 28.5 (1) |

-continued
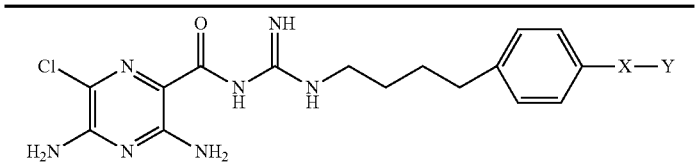
| X = | Y = | Fold Amiloride* |
|---|---|---|
| C=NH | $NH_2$ | 53.2 ± 19.3 (2) |
| NH | H | 32.6 ± 2 (3) |
| NH | $COCH_3$ | 52.3 ± 16.4 (3) |
| NH | $SO_2CH_3$ | 38.5 ± 4.2 (3) |
| NH | $CO_2C_2H_5$ | 29.0 ± 5.8 (2) |
| NH | $C(=NH)NH_2$ | 88.0 ± 18.0 (2) |
Example 44
| R = | R' = | Fold Amiloride* |
|---|---|---|
| OR' | H | 50.9 ± 19.8 (3) |
| NHR' | H | 28 (1) |
| NHR' | $COCH_3$ | 16 (1) |
| NHR' | $SO_2CH_3$ | 50.6 ± 11.9 (2) |
| NHR' | $CO_2C_2H_5$ | 24.1 ± 0.5 (3) |
| NHR' | $CO_2-(CH_3)_3$ | 29.0 ± 4.1 (2) |
| NHR | $C(=NH)NH_2$ | 66.2 ± 27.4 (4) |
Example 45
| X = | Fold Amiloride* |
|---|---|
| $NH_2$ | 56.5 ± 24 (4) |
| $NH-C(=NH)-NH_2$ | 120.6 ± 60.8 (11) |
| $NHSO_2CH_3$ | 64.0 (1) |
| $NHCO_2(CH_3)_3$ | 51.7 ± 10.1 (2) |
| $NHCOCH_3$ | 48.5 ± 26.5 (4) |

Example 46

[Chemical structure: chloro-diamino-pyrazine carboxamide guanidine with butyl-phenyl-OCH₂-C(O)-R]

| R = | Fold Amiloride* |
|---|---|
| —OH | 14.0 ± 4.6 (7) |
| —O(CH₃)₃ | 29.2 ± 10.9 (3) |
| —NH₂ | 48.2 ± 24.1 (7) |

Example 47

[Chemical structure: chloro-diamino-pyrazine carboxamide guanidine with butyl-phenyl-R]

| | | | | | Fold Amiloride* |
|---|---|---|---|---|---|
| CH₂ | CH₂ | OH | | | 79.2 ± 30.6 (4) |
| O | CH₂ | CH₂ | OH | | 84.9 ± 30.3 (6) |
| O | CH₂ | CH₂ | CH₂ | OH | 105.2 ± 26.6 (7) |
| CH₂ | CH₂ | CH₂ | CH₂ | OH | 37.4 (1) |
| O | CH₂ | CHOH | CH₂ | OH | 51.95 (50) |
| O | CH₂ | CHOH | CH₂ | NH₂ | 57.5 ± 24.5 (6) |
| O | CH₂ | CH₂ | CH₂ | CH₂ OH | 21 (1) |
| O | CH₂ | CH₂ | CHOH | CH₂ OH | 55.5 ± 19.3 (3) |
| O | CH₂ | CHOH | CHOH | CH₂ OH | 93.7 ± 42.1 (5) |
| O | CH₂ | CHOH | CHOH | CH₂ OH | 56.1 ± 15.6 (4) |
| N | CH₂ | CHOH | CHOH | CH₂ OH | 44.9 ± 14.7 (8) |

Example 48

[Chemical structure: chloro-diamino-pyrazine carboxamide guanidine with butyl-phenyl-X-R]

$R^2 = CH_2(CHOH)_3CH_2OH$
$R = CH_2CHOHCHOHCH_2OH$
$R^1 = CH_2CH_2OCH_3$

| | | | | | Fold Amiloride* |
|---|---|---|---|---|---|
| NH₂ | | | | | 32.6 ± 2 (3) |
| | R | | | | 44.9 ± 14.7 |
| NH | | | | | (8) |
| O | CH₂ | CH₂ | NH₂ | | 84.9 ± 30.3 (6) |
| O | CH₂ | CH₂ | NH | R[a] | 52.9 ± 14.3 (5) |
| O | CH₂ | CH₂ | NR | R[a,c] | 73.2 ± 49.3 (9) |
| O | CH₂ | CH₂ | O | R[1] | 76.1 (1) |
| O | CH₂ | CH₂ | O | CH₃ | 51.5 ± 14.9 (2) |
| O | R | | | | 93.7 ± 42.1 (5) |
| O | CH₂ | CHOH | CH₂ | OH | 51.95 (79) |
| O | CH₂ | CH₂ | NR | R[a,c] | 56.0 (1) |
| O | CH₂ | CH₂ | NR² | R[2,a] | |

[a] Chiral
[b] Racemic
[c] Enantiomers

Example 49

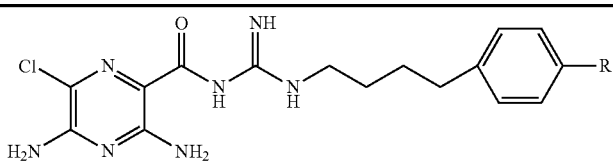

|  | Fold Amiloride* |
|---|---|
| O(CH$_2$)NHCO$_2$+ | 51.7 ± 10.1 (2) |
| OCH$_2$CO$_2$+ | 29.2 ± 10.9 (3) |
| OCH$_2$CO$_2$ET | 20 (1) |
| —NHCH$_2$CO$_2$+ | 29.0 ± 4.1 (2) |
| NHCO$_2$ET | 29.0 ± 5.38 (2) |
| CH$_2$NHCO$_2$ET | 24.1 ± 0.5 (3) |
| O(CH$_2$)$_2$NHCO$_2$ET | 17.7 ± 6.0 (2) |
| OCH$_2$CHOHCH$_2$NHCO$_2$+ | 77.9 ± 24.0 (3) |
| O(CH$_2$)$_3$NHCO$_2$+ | 37.5 ± 12.8 (4) |
| (CH$_2$)$_4$—NHCO$_2$+ | 16.9 ± 2.3 (2) |

+ = (CH$_3$)$_3$; Boc = —CO$_2$(CH$_3$)$_3$

Example 50

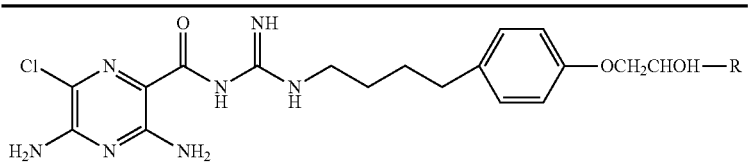

| R = | Position | Fold Amiloride* |
|---|---|---|
| H | Ortho | 21.7 ± 4.8 (2) |
| H | Meta | 41.1 ± 8.5 (2) |
| H | Para | 80.3 ± 25.5 (9) |
| CH$_2$OH | Ortho | 24.0 ± 1.0 (2) |
| CH$_2$OH | Meta | 40 (1) |
| CH$_2$OH | Para | 51.55 (79) |

Example 51

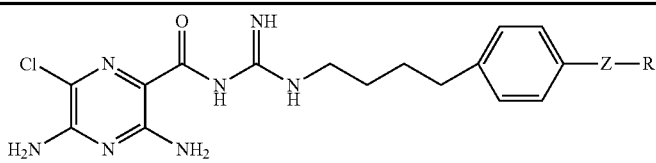

| R =\Z = | H | O(CH$_2$)$_2$—R | O(CH$_2$)$_3$—R | CH$_2$R | (CH$_2$)$_3$R |
|---|---|---|---|---|---|
| OH<br>Xamiloride |  | 84.9 ± 30.3 | 105.2 ± 26.6 | 50.9 ± 19.8 (3) |  |

| R =\Z = | H | O(CH$_2$)$_2$—R | O(CH$_2$)$_3$—R | CH$_2$R | —(CH$_2$)$_3$R |
|---|---|---|---|---|---|
| NH$_2$<br>Xamiloride | 32.6 ± 2 | 56.5 ± 0 | 102.6 ± 49 | 26.2 ± 5.1 (3) | 54.4 ± 43.5 (6) |

| R =\Z = | H | O(CH$_2$)$_2$—R | O(CH$_2$)$_3$—R | CH$_2$R | (CH$_2$)$_3$R |
|---|---|---|---|---|---|
| $\overset{NH}{\underset{\parallel}{—NHCNH_2}}$<br>Xamiloride | 88.0 ± 18.0 | 98.0 ± 58.5 (18) | 50.2 ± 17.4 (4) | 35 (1) | 47.6 (3) |

Example 52

Effect of Compound 9518 on MCC

Figure 3:
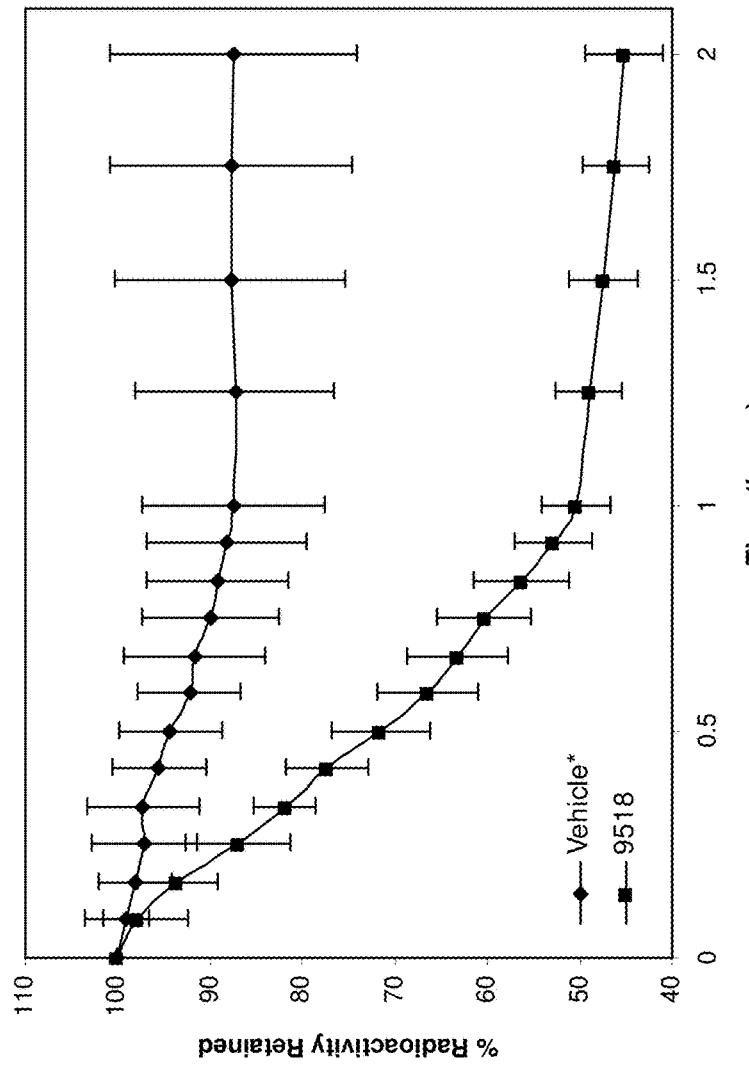
FIG. 3: Effect of a compound of the present invention on MCC at t=0 hrs as described in Example 32 herein.
Figure 4:
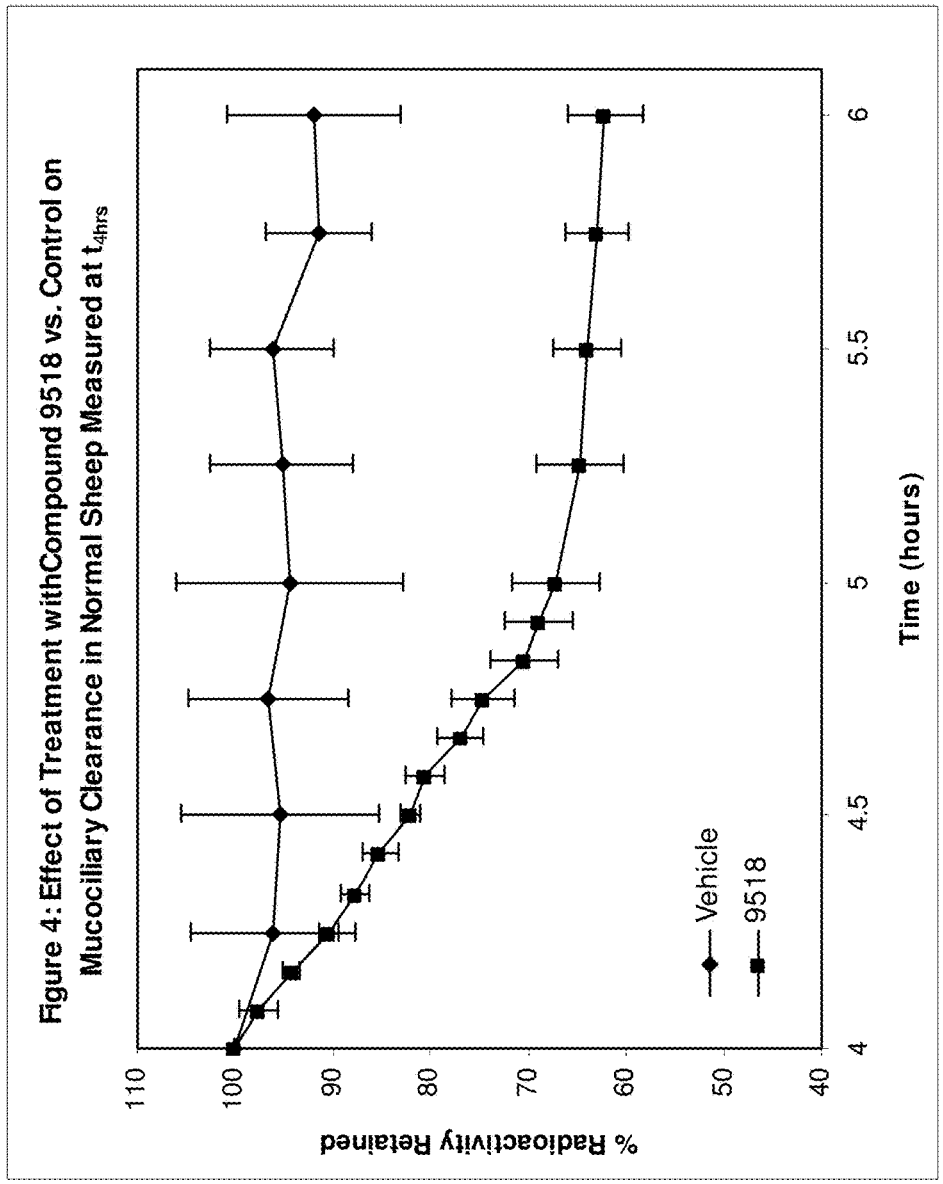
FIG. 4: Effect of a compound of the present invention on MCC at t=4 hrs as described in Example 32 herein.

These experiments were conducted according to methods of Example 32 with compound 9518 and the vehicle as a control The results are shown in FIGS. 3 (t=0 hours) and 4 (t=4 hours).

Example 53

Effect of Compound 9714 on MCC

Figure 5:
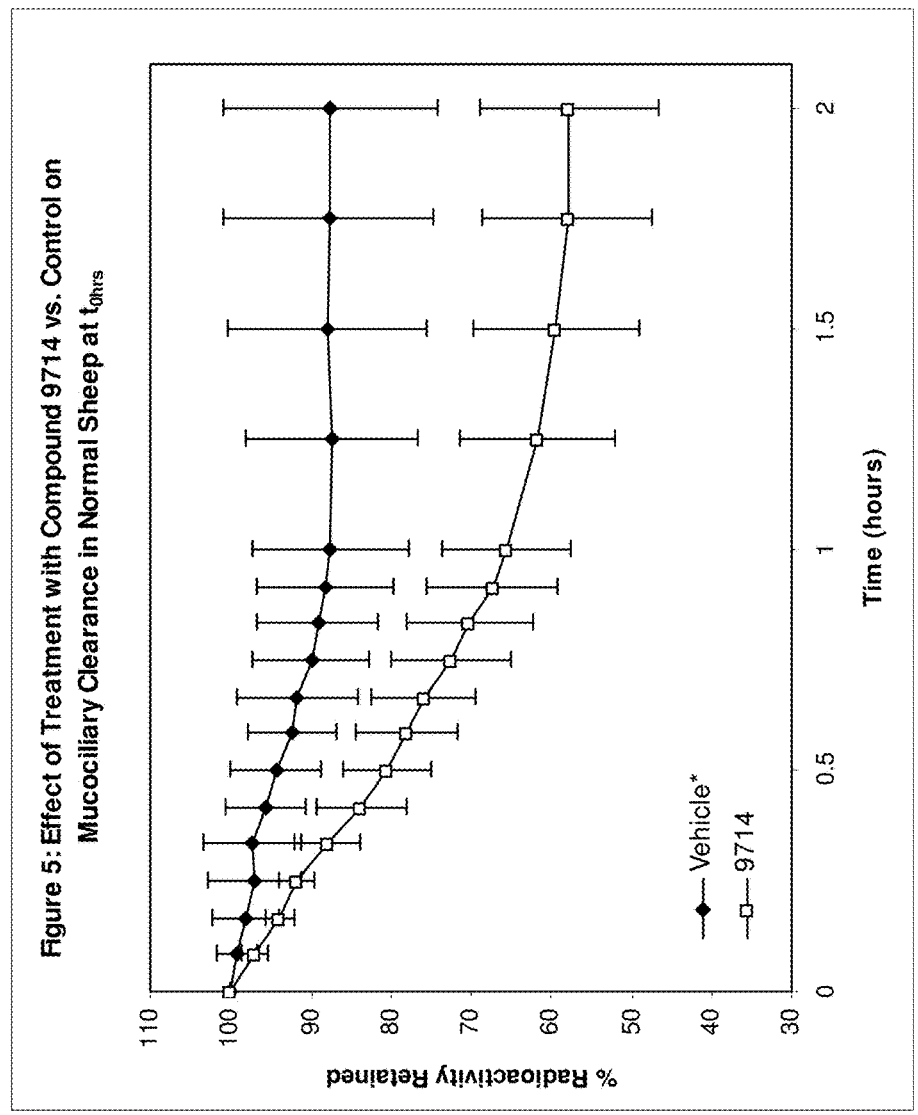
FIG. 5: Effect of a compound of the present invention on MCC at t=0 hrs as described in Example 32 herein.
Figure 6:
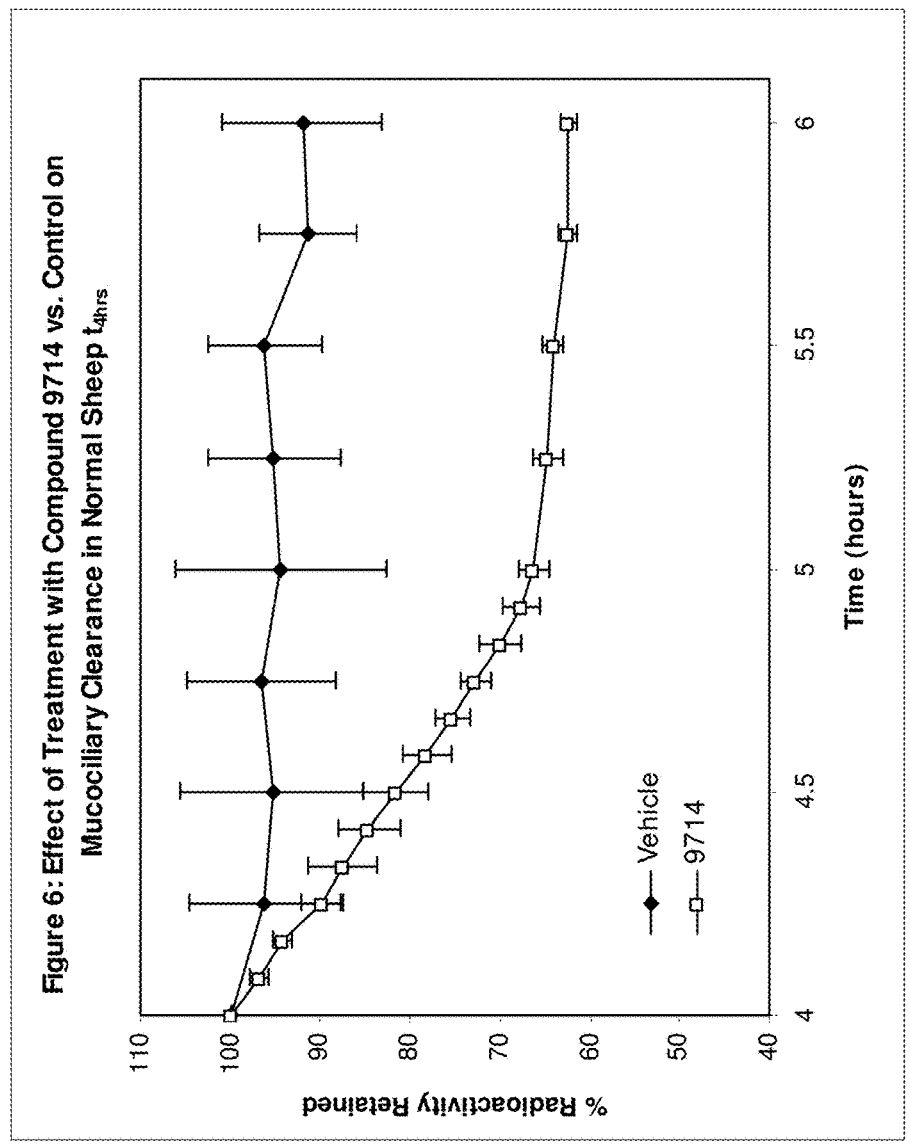
FIG. 6: Effect of a compound of the present invention on MCC at t=4 hrs as described in Example 32 herein.

These experiments were conducted according to methods of Example 32 with compound 9714 and the vehicle as a control. The results are shown in FIGS. 5 (t=0 hours) and 6 (t=4 hours).

Example 54

Effect of Compound 10833 on MCC

Figure 7:
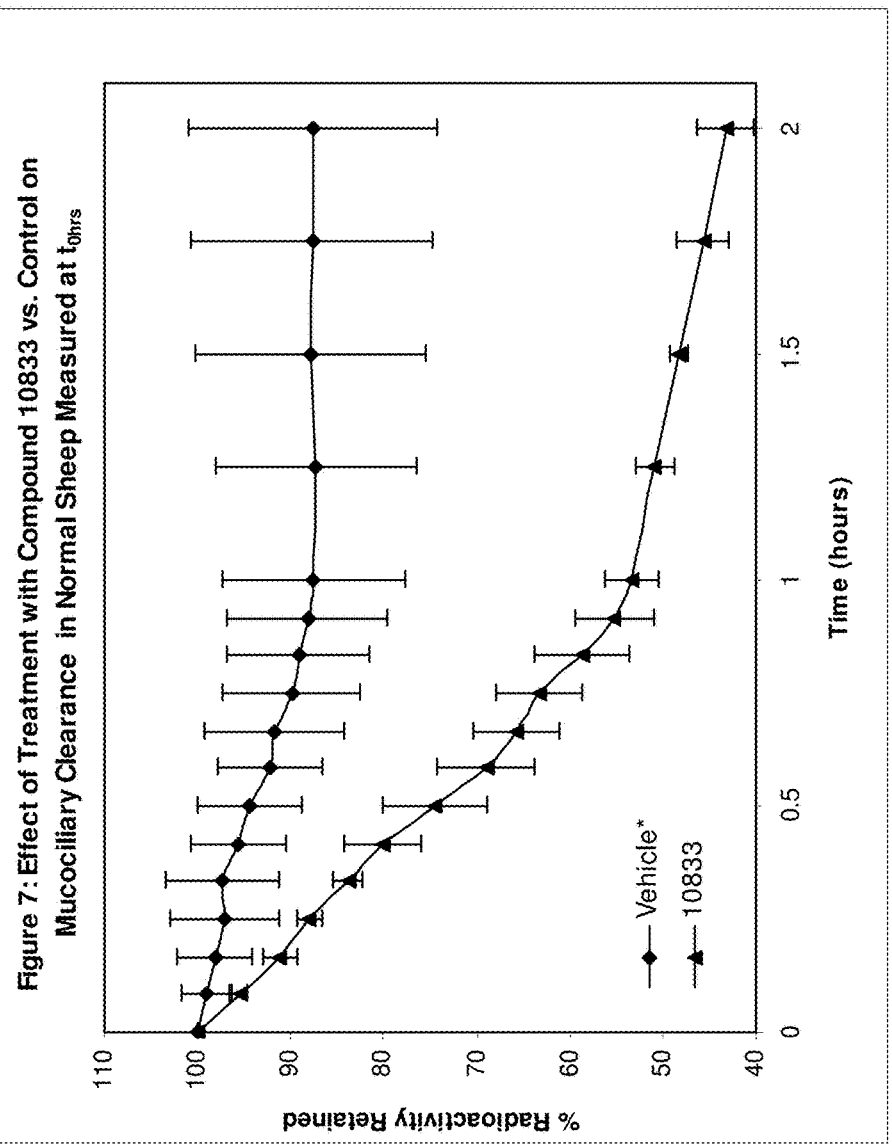
FIG. 7: Effect of a compound of the present invention on MCC at t=0 hrs as described in Example 32 herein.
Figure 8:
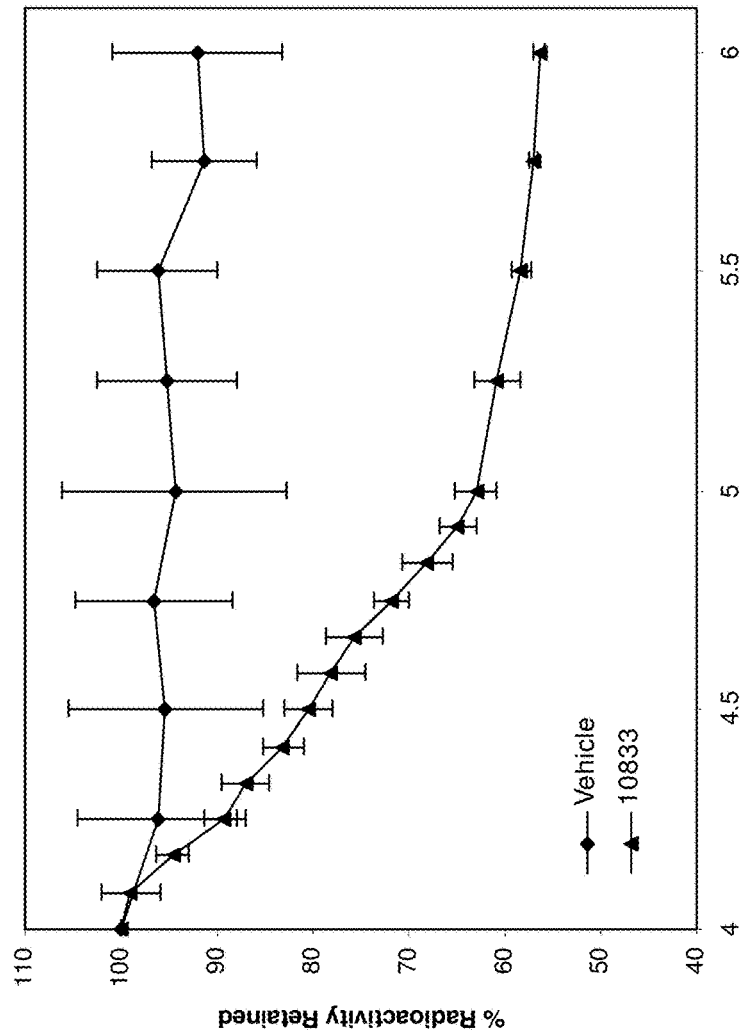
FIG. 8: Effect of a compound of the present invention on MCC at t=4 hrs as described in Example 32 herein.

These experiments were conducted according to methods of Example 32 with compound 10833 and the vehicle as a control The results are shown in FIGS. 7 (t=0 hours) and 8 (t=4 hours).

Obviously, numerous modifications and variations of the present invention are possible in light of the above teachings. It is therefore to be understood that within the scope of the appended claims, the invention may be practiced otherwise than as specifically described herein.

What is claimed:

1. A pharmaceutical composition comprising a compound of Formula (I), or a pharmaceutically acceptable salt thereof, and an osmotically active agent:

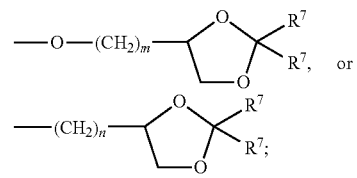

(I)

wherein:
X is halogen;
Y is $-N(R^2)_2$;
$R^1$ is hydrogen or lower alkyl;
each $R^2$ is independently $-R^7$;
$R^3$ is hydrogen or lower alkyl;
$R^4$ is a group represented by formula (A):

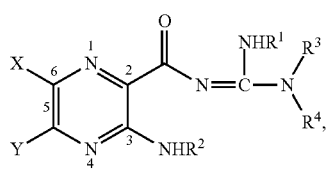

(A)

and wherein:
each $R^L$ is independently $-R^7$, $-(CH_2)_n-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

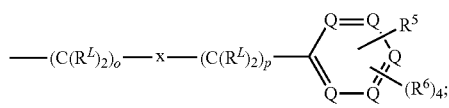

each o is independently an integer from 0 to 10;
each p is an integer from 0 to 10;
with the proviso that the sum of o and p in each contiguous chain is from 1 to 10;
each x is, independently, O, $NR^{10}$, $C(=O)$, CHOH, $C(=N-R^{10})$, $CHNR^7R^{10}$, or a single bond;
each $R^5$ is independently $-(CH_2)_m-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose, each $R^6$ is independently $-R^7$, $-OR^{11}$, $-N(R^7)_2$, $-(CH_2)_m-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-$ $NR^{10}$—$CH_2(CHOR^8)(CHOR^8)_n$—$CH_2OR^8$,
—$(CH_2)_n$—$CO_2R^7$, —$O$—$(CH_2)_m$—$CO_2R^7$,
—$OSO_3H$, —O-glucuronide, —O-glucose,
wherein when two $R^6$ are —$OR^{11}$ and are located adjacent to each other on a phenyl ring, the alkyl moieties of the two $R^6$ may be bonded together to form a methylenedioxy group,

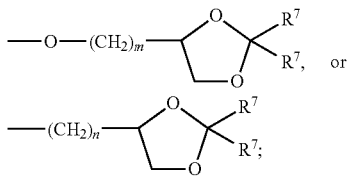  or

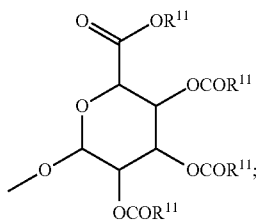

each $R^7$ is independently hydrogen or lower alkyl;
each $R^8$ is independently hydrogen, lower alkyl, —$C(=O)$—$R^{11}$, glucuronide, 2-tetrahydropyranyl, or

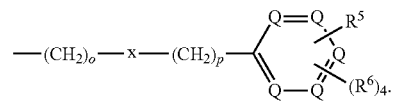

each $R^9$ is independently —$CO_2R^7$, —$CON(R^7)_2$, —$SO_2CH_3$, or —$C(=O)R^7$;
each $R^{10}$ is independently —H, —$SO_2CH_3$, —$CO_2R^7$, —$C(=O)NR^7R^9$, —$C(=O)R^7$, or —$CH_2$—$(CHOH)_n$—$CH_2OH$;
each Z is independently CHOH, $C(=O)$, $CHNR^7R^{10}$, $C=NR^{10}$, or $NR^{10}$;
each $R^{11}$ is independently lower alkyl;
each g is independently an integer from 1 to 6;
each m is independently an integer from 1 to 7;
each n is independently an integer from 0 to 7; and
each Q is independently C—$R^5$ or C—$R^6$, wherein one Q is C—$R^5$.

2. The pharmaceutical composition of claim 1, wherein the osmotically active agent is a saline solution.

3. The pharmaceutical composition of claim 1, wherein the pharmaceutical composition is suitable for inhalation.

4. The pharmaceutical composition of claim 1, wherein the pharmaceutical composition is suitable for administration by nebulizer.

5. The pharmaceutical composition of claim 1, wherein the compound is present as a free base.

6. The pharmaceutical composition of claim 1, wherein each instance of $R^1$, $R^2$, and $R^3$ is hydrogen.

7. The pharmaceutical composition of claim 1, wherein X is chlorine.

8. The pharmaceutical composition of claim 1, wherein Y is —$NH_2$.

9. The pharmaceutical composition of claim 1, wherein $R^4$ is of the formula:

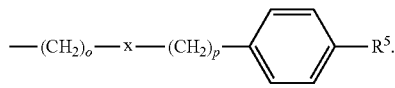

10. The pharmaceutical composition of claim 1, wherein $R^4$ is of the formula:

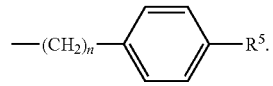

11. The pharmaceutical composition of claim 1, wherein $R^4$ is of the formula:

—$(CH_2)_n$—⌬—$R^5$.

12. The pharmaceutical composition of claim 1, wherein:
each instance of $R^1$, $R^2$, and $R^3$ is hydrogen;
$R^4$ is of the formula:

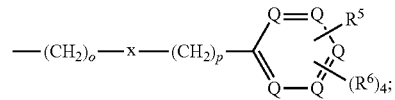

and
x is a single bond.

13. The pharmaceutical composition of claim 12, wherein X is chlorine.

14. The pharmaceutical composition of claim 12, wherein Y is —$NH_2$.

15. The pharmaceutical composition of claim 12, wherein $R^5$ is —O—$(CH_2)_m$—$(Z)_g$—$R^7$.

16. The pharmaceutical composition of claim 14, wherein g is 1; and Z is $NR^{10}$.

17. The pharmaceutical composition of claim 15, wherein $R^{10}$ is —$CH_2$—$(CHOH)_n$—$CH_2OH$.

* * * * *